United States Patent
Avkin-Nachum et al.

(10) Patent No.: US 9,889,200 B2
(45) Date of Patent: Feb. 13, 2018

(54) SPHINGOLIPID-POLYALKYLAMINE-OLIGONUCLEOTIDE COMPOUNDS

(71) Applicants: QBI ENTERPRISES LTD., Nes Ziona (IL); BIO-LAB LTD., Jerusalem (IL)

(72) Inventors: Sharon Avkin-Nachum, Nes Zionna (IL); Jean Hildesheim, Modiin-Macabim-Reut (IL); Tirtsa Kleinman, Jerusalem (IL); Jean-Christophe Truffert, Saint-Prest (FR); Gerald Mathis, Ouvrouer les Champs (FR)

(73) Assignees: QBI ENTERPRISES LTD., Nes Ziona (IL); BIO-LAB LTD., Jerusalem (IL)

( * ) Notice: Subject to any disclaimer, the term of this patent is extended or adjusted under 35 U.S.C. 154(b) by 0 days.

(21) Appl. No.: 14/908,125

(22) PCT Filed: Jul. 30, 2014

(86) PCT No.: PCT/IL2014/050691
§ 371 (c)(1),
(2) Date: Jan. 28, 2016

(87) PCT Pub. No.: WO2015/015496
PCT Pub. Date: Feb. 5, 2015

(65) Prior Publication Data
US 2016/0175452 A1    Jun. 23, 2016

Related U.S. Application Data

(60) Provisional application No. 61/860,274, filed on Jul. 31, 2013.

(51) Int. Cl.
*A61K 47/48* (2006.01)
*C12N 15/113* (2010.01)
*C12N 15/11* (2006.01)
*A61K 47/54* (2017.01)
*A61K 48/00* (2006.01)

(52) U.S. Cl.
CPC ...... *A61K 47/48046* (2013.01); *A61K 47/543* (2017.08); *C12N 15/111* (2013.01); *C12N 15/113* (2013.01); *C12N 15/1135* (2013.01); *C12N 15/1137* (2013.01); *C12Y 207/11021* (2013.01); *A61K 48/00* (2013.01); *C12N 2310/11* (2013.01); *C12N 2310/113* (2013.01); *C12N 2310/14* (2013.01); *C12N 2310/141* (2013.01); *C12N 2310/351* (2013.01); *C12N 2320/32* (2013.01)

(58) Field of Classification Search
None
See application file for complete search history.

(56) References Cited

U.S. PATENT DOCUMENTS

2011/0237648 A1    9/2011   Khvorova et al.

FOREIGN PATENT DOCUMENTS

WO   WO 2004/110980   12/2004
WO   WO 2010/150004   12/2010

OTHER PUBLICATIONS

Manoharan N: "Oligonucleotide conjugates as potential antisense drugs with improved uptake, biodistribution, targeted delivery, and mechanism of action", Antisense & Nucleic Acid Drug Development, Mary Ann Liebert, Inc., New York, US, vol. 12, Jan. 1, 2002, pp. 103-128.

*Primary Examiner* — Tracy Vivlemore
(74) *Attorney, Agent, or Firm* — JMB Davis Ben-David

(57) ABSTRACT

Provided herein are sphingolipid-polyalkylamine phosphoramidites, methods of generating sphingolipid-polyalkylamine-oligonucleotide compounds, pharmaceutical compositions comprising such compounds, and to methods of use thereof in treating cancer.

15 Claims, 11 Drawing Sheets

SPHINGOLIPID-POLYALKYLAMINE-OLIGONUCLEOTIDE COMPOUNDS

RELATED APPLICATIONS

This is the U.S. National Stage of International Application No. PCT/IL2014/050691, filed Jul. 30, 2014, which claims the benefit of U.S. Provisional Application Ser. No. 61/860,274 filed Jul. 31, 2013, entitled "SPHINGOLIPID-POLYALKYLAMINE-OLIGONUCLEOTIDE COMPOUNDS" and which is incorporated herein by reference in its entirety and for all purposes.

SEQUENCE LISTING

This application incorporates-by-reference nucleotide sequences which present in the file named "250_PCT1.ST25", which is 24 kb in size, and which was created on Jul. 27, 2014 in the IBM-PC machine format, having an operating system compatibility with MS-Windows, and is submitted herewith.

FIELD OF THE INVENTION

Disclosed herein are sphingolipid-polyalkylamine based compounds including sphingolipid-polyalkylamine phosphoramidites and methods to generate sphingolipid-polyalkylamine-oligonucleotide compounds, the sphingolipid-polyalkylamine-oligonucleotide compounds, pharmaceutical compositions comprising same and methods of use thereof for the modulation of gene expression. The oligonucleotides include triplex DNA and single-stranded and double-stranded oligonucleotides including antisense molecules, and RNAi molecules such as double-stranded RNA (dsRNA), including siRNA, siNA, miRNA anti-miR and saRNA useful in treatment of subjects suffering from cancer.

BACKGROUND OF THE INVENTION

Use of therapeutic oligonucleotides, including double-stranded RNA (dsRNA), in the clinic has been hampered by the lack of efficient and safe delivery systems. Cationic lipids have been used to deliver therapeutic oligonucleotides, however, their use is limited by cell toxicity and the fact that cationic lipids accumulate primarily in the liver.

International Patent Publication Nos. WO 2008/104978, WO 2009/044392, WO 2011/066475, WO 2011/084193 and WO 2011/085056 disclose chemically modified dsRNA, and are hereby incorporated by reference in their entirety.

A process for large-scale preparation of sphingosine is provided in U.S. Pat. No. 6,469,148 and sphingolipid-polyalkylamine conjugates are disclosed in U.S. Pat. No. 7,771,711; both are incorporated by reference in their entirety.

PCT publication No. WO 2010/150004 relates to oligonucleotides carrying lipid molecules and their use as inhibitors of gene expression.

There remains a need for active and safe dsRNA therapeutic agents, which exhibit at least one of improved cellular uptake with enhanced endosomal release, increased circulation time, favorable biodistribution, reduced toxicity and reduced immunogenicity compared to the unmodified counterparts, while retaining therapeutic activity.

SUMMARY OF THE INVENTION

Provided herein are oligonucleotide compounds comprising a sphingolipid-polyalkylamine conjugate, methods for preparing such compounds and intermediates useful in generating such compounds. The sphingolipid-polyalkylamine oligonucleotide compounds disclosed herein possess structures and modifications which are useful, for example in providing at least one of increased cellular uptake, enhanced endosomal release, increased circulation time, improved biodistribution, reduced toxicity, reduced immunogenicity, reduced off-target effects, or enhanced loading into the RISC complex when compared to an unmodified nucleic acid molecule. The sphingolipid-polyalkylamines are beneficially attached to single-stranded or double-stranded nucleic acid molecules and are useful as therapeutic agents in the treatment of cancer.

In one aspect, provided herein is a compound comprising a sphingolipid-polyalkylamine conjugate, having general formula I:

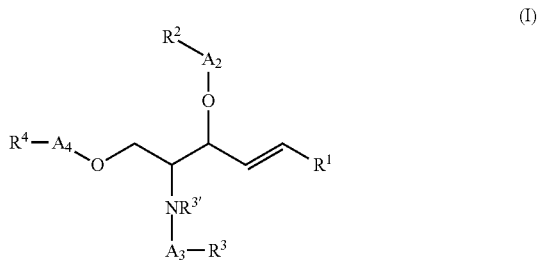

(I)

wherein $R^1$ is a branched or linear $C_7$-$C_{24}$ alkyl, alkenyl or polyenyl;

$R^2$, $R^3$ and $R^4$ each independently is hydrogen, a branched or linear polyalkylamine or derivative thereof, a nucleotide, an oligonucleotide, a coupling moiety, or a protecting group;

$R^{3'}$ is hydrogen; $C_1$-$C_4$ alkyl or a protecting group;

$A_2$, $A_3$ and $A_4$ each independently is present or absent but if present is C(O), C(O)NHX, C(O)NHR$^5$X, C(O)R$^5$X, C(O)R$^5$C(O)X, R$^5$X or R$^5$OC(O)X;

$R^5$ is a branched or linear $C_1$-$C_{20}$ hydrocarbyl chain optionally substituted with one or more heteroatoms;

X is present or absent but if present is S, P, O or NH;

at least one of $R^2$, $R^3$ or $R^4$ is a branched or linear polyalkylamine or derivative thereof; and at least one of $R^2$, $R^3$ or $R^4$ is a nucleotide, an oligonucleotide or a coupling moiety;

or a salt of such compound.

In some embodiments, $R^1$ is $C_7$-$C_{24}$ alkyl, $C_{10}$-$C_{20}$ alkyl or $C_{10}$-$C_{16}$ alkyl. Preferably $R^1$ is $C_{13}$ alkyl.

In some embodiments, $A_2$ is C(O). In some embodiments, $A_4$ is C(O). In some embodiments, $R^2$ is a linear polyalkylamine or a derivative thereof. In some embodiments, $R^4$ is a linear polyalkylamine or a derivative thereof. Preferably, the linear polyalkylamine is spermidine or spermine. In some embodiments, $R^2$ is spermidine. In other embodiments, $R^2$ is spermine. In some embodiments, $R^4$ is spermidine. In other embodiments, $R^4$ is spermine In some embodiments, $R^{3'}$ is hydrogen, $A_2$ is C(O), $A_3$ is absent, $R^2$ is spermine and provided herein is a compound having general formula (Ia):

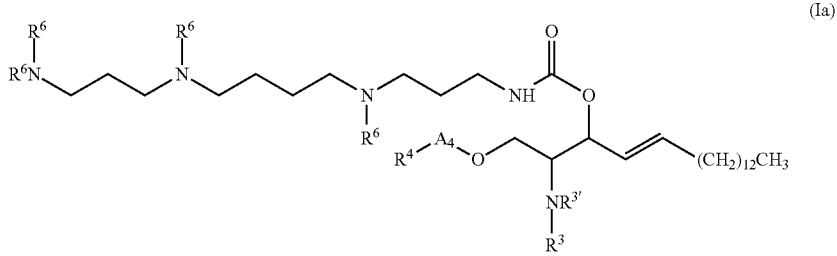
(Ia)

wherein
$A_4$ is present or absent, but if present is selected from the group consisting of C(O), C(O)NHX, C(O)NHR$^5$X, C(O)R$^5$X, C(O)R$^5$C(O)X, R$^5$X and R$^5$OC(O)X;
$R^3$ is hydrogen or a protecting group;
$R^4$ is a nucleotide, an oligonucleotide or a coupling moiety;
$R^5$ is a branched or linear $C_1$-$C_{20}$ hydrocarbyl chain optionally substituted with one or more heteroatoms; and
each $R^6$ independently is hydrogen or a protecting group;
or a salt of such compound.

In some embodiments, $R^{3'}$ is hydrogen, $A_2$ is C(O), $A_3$ is absent, $R^2$ is spermidine and provided herein is a compound having general formula (Ib):

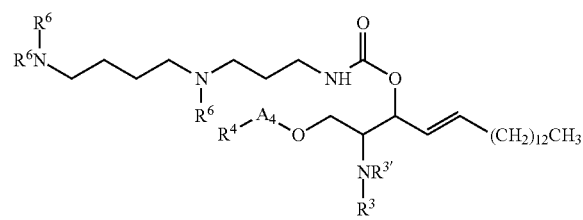

wherein
$A_4$ is present or absent, but if present is selected from the group consisting of C(O), C(O)NHX, C(O)NHR$^5$X, C(O)R$^5$X, C(O)R$^5$C(O)X, R$^5$X and R$^5$OC(O)X;
$R^3$ is hydrogen or a protecting group;
$R^4$ is a nucleotide, an oligonucleotide or a coupling moiety;
$R^5$ is a branched or linear $C_1$-$C_{20}$ hydrocarbyl chain optionally substituted with one or more heteroatoms; and
each $R^6$ independently is hydrogen or a protecting group;
or a salt of such compound.

In various embodiments of general formulae I, Ia and Ib, $A_4$ is C(O)NHR$^5$X, wherein $R^4$ is a nucleotide, an oligonucleotide or a coupling moiety. In some such embodiments, $R^5$ is a $C_6$ hydrocarbyl chain and X is O.

In various embodiments of general formulae I, Ia and Ib, $R^4$ is a coupling moiety. A coupling moiety may be selected from a phosphoramidite; an amine (—NH$_2$); a carboxyl (—COOH) or activated carboxyl including NHS esters; a sulfhydryl (—SH) and disulfide bond (—S—S—), which are reduced to sulfhydryls; a carbonyl (—CHO); a cyano (—CN), a hydroxyl (—OH) and an azide including an aryl azide. In some embodiments $R^5$ is a phosphoramidite, such as a 2-cyanoethyl N,N,N',N'-tetraisopropylphosphorodiamidite. In some embodiments, $R^4$ is an activated carboxyl, preferably a NHS ester.

In various embodiments of general formulae I, Ia and Ib, $R^4$ is a 2-cyanoethyl N,N,N',N'-tetraisopropylphosphorodiamidite, and provided herein is a compound having general formula (IIa) or (IIb) as shown hereinbelow

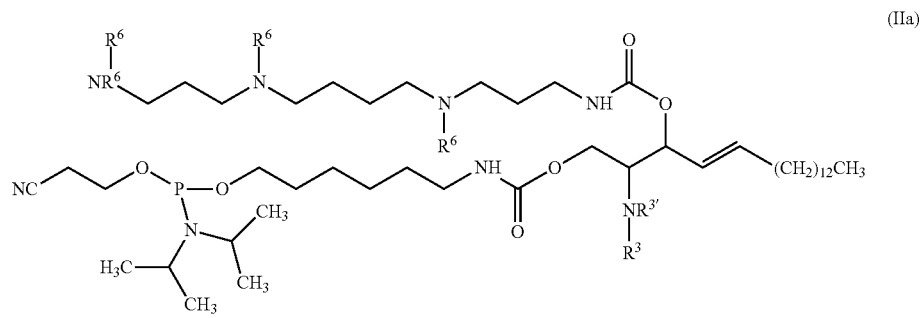
(IIa)

-continued

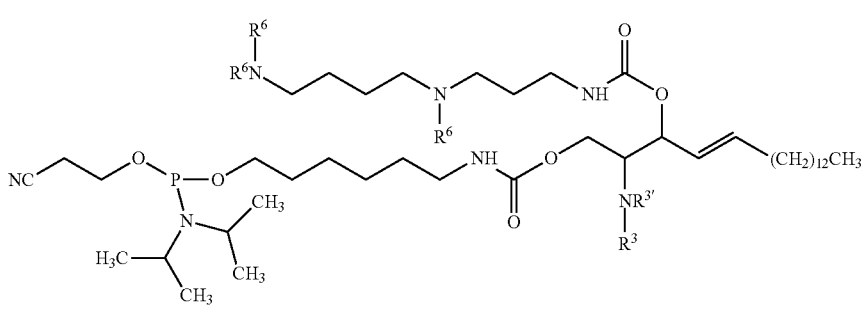
(IIb)

wherein each $R^3$ and $R^6$ independently is hydrogen or a protecting group.

In various embodiments of general formulae I, Ia and Ib, $A_4$ is $C(O)NHR^5C(O)X$, $R^4$ is a NHS ester, $R^5$ is a $C_6$ alkyl chain and X is O and provided herein is a compound having general formula IIIa or IIIb:

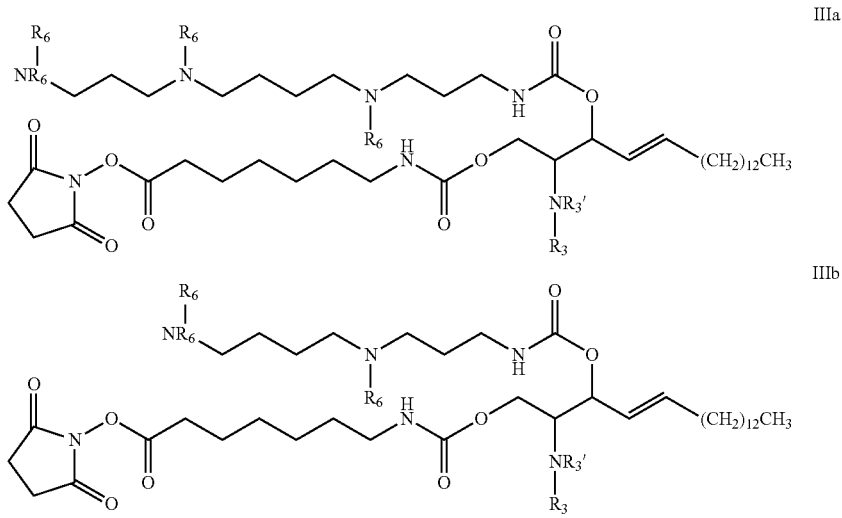

wherein each of $R^3$, $R^{3'}$ and $R^6$ independently is a hydrogen or protecting group.

In various embodiments of any of the general formulae disclosed above, $R^4$ is an oligonucleotide. The oligonucleotide is a single-stranded oligonucleotide or a double-stranded oligonucleotide, which may be partially or fully chemically modified.

The single-stranded oligonucleotide is, for example, an antisense molecule selected from the group consisting of a DNA antisense, a RNA antisense, a DNA/RNA chimera antisense, an exon skipping molecule, an anti-miR, an aRNA, an aptamer, a synthetic mRNA, lncRNA and shRNA. In some embodiments the oligonucleotide is a double-stranded nucleic acid (dsNA) molecule. The double-stranded oligonucleotide is, for example, dsRNA such as siRNA, miRNA, or miRNA mimetic.

In some embodiments of the method, compound for use or use, the chemically modified dsNA molecule comprises
 a. a sense strand of 8 to 49 nucleotides having a 5' terminus and a 3'terminus;
 b. an antisense strand of 15 to 49 nucleotides in length and each strand having a 5' terminus and a 3'terminus;
 c. a 15 to 49 nucleotide sequence of the antisense strand is complementary to a consecutive sequence of a target gene RNA;
 d. a 8 to 49 nucleotide sequence of the sense strand is complementary to the antisense strand.

In some embodiments, the antisense strand and the sense strand are asymmetric, for example, the sense strand is 8 to 14 nucleotides in length and the antisense strand is 15 to 23 nucleotides in length. In some embodiments, each of the antisense strand and the sense strand is independently 19-23 nucleotides in length. In some embodiments, the antisense strand and the sense strand are the same length. In some embodiments, the antisense strand and the sense strand are 19-23 nucleotides in length, preferably 19 nucleotides. In some embodiments the sense strand comprises two or more sets of covalently joined consecutive nucleotides which are not joined by a covalent bond (i.e. the sense strand is "nicked").

In some embodiments the double-stranded nucleic acid molecule is a double-stranded RNA (dsRNA) having the structure set forth below
 5'(N)x-Z 3' (antisense strand)
 3'Z'-(N')y-z" 5' (sense strand)
wherein each of N and N' is an unmodified ribonucleotide, a modified ribonucleotide or an unconventional moiety;
 wherein each of (N)x and (N')y is an oligonucleotide in which each consecutive N or N' is joined to the next N or N' by a covalent bond;

wherein each of x and y is independently an integer between 15 and 49;

wherein z" is present or absent, but if present is a capping moiety covalently attached to the 5' terminus of the sense strand;

wherein each of Z and Z' is independently present or absent, but if present is 1-5 consecutive nucleotides or non-nucleotide moieties or a combination thereof covalently attached at the 3' terminus of the strand in which it is present;

wherein the sphingolipid-polyalkylamine conjugate is covalently attached to at least one of the 3' terminus of the antisense strand, the 3' terminus of the sense strand or the 5' terminus of the sense strand;

wherein the sequence of (N')y is substantially complementary to the sequence of (N)x; and wherein (N)x comprises an antisense sequence complementary to a consecutive sequence in a target RNA;

with the proviso that when the sphingolipid-polyalkylamine conjugate is attached at the 5' terminus of the sense strand z" is absent.

In some embodiments of the dsRNA, each covalent bond joining each consecutive N or N' is independently selected from a phosphodiester bond or a phosphodiester bond.

In certain embodiments of the dsRNA, x=y and each of x and y is an integer from 15-49, or from 17-40, preferably from 18-25. In some embodiments, x=y=19, 20, 21, 22 or 23. Preferably x=y=19 or 21.

In certain embodiments, x=y=19. In some embodiments x is an integer from 19-25 and y is an integer from 15-17, thereby generating a dsRNA having 15-17 nucleotide base pairs.

The sphingolipid-polyalkylamine conjugate is preferably covalently attached to at least one of the 3' terminus of the sense strand (N')y, the 3' terminus of the antisense strand (N)x or the 5' terminus of the sense strand (N')y. In some embodiments, the sphingolipid-polyalkylamine conjugate is covalently attached to the 3' terminus of (N)x. In some embodiments, the sphingolipid-polyalkylamine conjugate is covalently attached to the 3' terminus of (N')y. The 3' terminus of (N)x or (N')y may include Z or Z', respectively, for example a nucleotide or non-nucleotide overhang, to which the sphingolipid-polyalkylamine conjugate is attached. Such compounds may further include a capping moiety (z") covalently attached to the 5' terminus of the sense strand.

In preferred embodiments, the sphingolipid-polyalkylamine conjugate is covalently attached to the 5' terminus of (N')y. In such compounds, one or more nucleotide or non-nucleotide moieties or a combination thereof, is covalently attached at the 3' terminus of (N)x and/or at the 3' terminus of (N)y. In some embodiments, wherein the sphingolipid-polyalkylamine conjugate is attached to the 3' or 5' terminus of (N')y, Z is present. In some embodiments, wherein the sphingolipid-polyalkylamine conjugate is attached to the 3' terminus of (N)x or the 5' terminus of (N')y, Z' is present.

In some embodiments, the sequence of (N')y is fully complementary to the sequence of (N)x, and the sequence of (N)x is fully complementary to the target RNA. The sequence of (N')y may also be fully complementary to the sequence of (N)x and the sequence of (N)x is partially complementary to the target RNA. In such compounds, for example, the 5' terminal nucleotide of the antisense strand [(N)x] is mismatched to the target RNA.

In some embodiments of the dsRNA, each N and N' is an unmodified ribonucleotide.

In some embodiments of the dsRNA, at least one of N or N' is a sugar modified ribonucleotide.

In some embodiments of the dsRNA, at least one of N or N' is an unconventional moiety selected from a DNA, a LNA, a mirror nucleotide, a 2'5' linked nucleotide and an a basic moiety.

In some embodiments, the sequence of (N')y is fully complementary to the sequence of (N)x, and the sequence of (N)x is fully complementary to the target RNA.

In some embodiments, the sequence of (N')y is fully complementary to the sequence of (N)x and the sequence of (N)x is partially complementary to the target RNA.

In some embodiments, the sequence of (N')y is partially complementary to the sequence of (N)x and the sequence of (N)x is partially complementary to the target RNA.

In some embodiments the 5' terminal nucleotide of the antisense strand [(N)x] is mismatched to the target RNA.

In some embodiments of any of the general formulae described herein, wherein a target RNA is mRNA, preferably human mRNA. In other embodiments a target RNA is a non-coding RNA, either long or short, transcribed from a mammalian genome.

In another aspect, provided herein is a composition comprising a compound disclosed herein, or the salt of such a compound; and a carrier. In preferred embodiments the compound comprises a sphingolipid-polyalkylamine-oligonucleotide compound, which includes the features disclosed above. In some embodiments the carrier is a pharmaceutically acceptable carrier. In some embodiments, the composition is formulated for subcutaneous, intraperitoneal or intratumoral administration.

In a third aspect, provided herein is a method for treating cancer in a subject having cancer, comprising administering to the subject a therapeutic amount of a sphingolipid-polyalkylamine-oligonucleotide compound, thereby treating the cancer.

Further provided is a sphingolipid-polyalkylamine-oligonucleotide compound or salt of such compound or composition comprising such compound or salt of such compound, for use in treating cancer.

Further provided is use of the sphingolipid-polyalkylamine oligonucleotide compound or salt of such compound for the manufacture of a medicament for the treatment of cancer.

In yet another aspect, provided is a method for enhancing endosomal release of a therapeutic oligonucleotide into the cytoplasm of a cell, comprising contacting the cell with a sphingolipid-polyalkylamine oligonucleotide thereby enhancing endosomal release. The cell may be contacted with the compound directly or with a composition of such compound. Further provided is a sphingolipid-polyalkylamine-oligonucleotide compound, for use in enhancing endosomal release of a therapeutic oligonucleotide into the cytoplasm of a cell.

Further provided is the use of a sphingolipid-polyalkylamine-oligonucleotide compound, for the manufacture of a medicament for enhancing endosomal release of a therapeutic oligonucleotide into the cytoplasm of a cell.

In another aspect, provided herein is a sphingolipid-polyalkylamine phosphoramidite. The phosphoramidite is useful in the generation of sphingolipid-polyalkylamine oligonucleotide compounds. In certain embodiments of the sphingolipid-polyalkylamine phosphoramidite the sphingolipid is sphingosine; and wherein the polyalkylamine is spermine or spermidine. Further provided, infra, is a method of synthesizing a sphingolipid-polyalkylamine phosphoramidite.

Coupling of the sphingolipid-polyalkylamine conjugate to an oligonucleotide may be carried out during or after chemical synthesis of an oligonucleotide to form a sphingolipid-polyalkylamine-oligonucleotide compound. The sphingolipid-polyalkylamine conjugate may be attached to a terminus of the oligonucleotide or to an internal position in the oligonucleotide. The sphingolipid-polyalkylamine conjugate may be coupled as a phosphoramidite, H-phosphonate, or phosphate triester derivative. A person skilled in the art will determine the appropriate compound and method of coupling.

This disclosure is intended to cover any and all adaptations or variations of combination of features that are disclosed in the various embodiments herein. Although specific embodiments have been illustrated and described herein, it should be appreciated that the invention encompasses any arrangement of the features of these embodiments to achieve the same purpose. Combinations of the above features, to form embodiments not specifically described herein, will be apparent to those of skill in the art upon reviewing the instant description.

Figure 1:
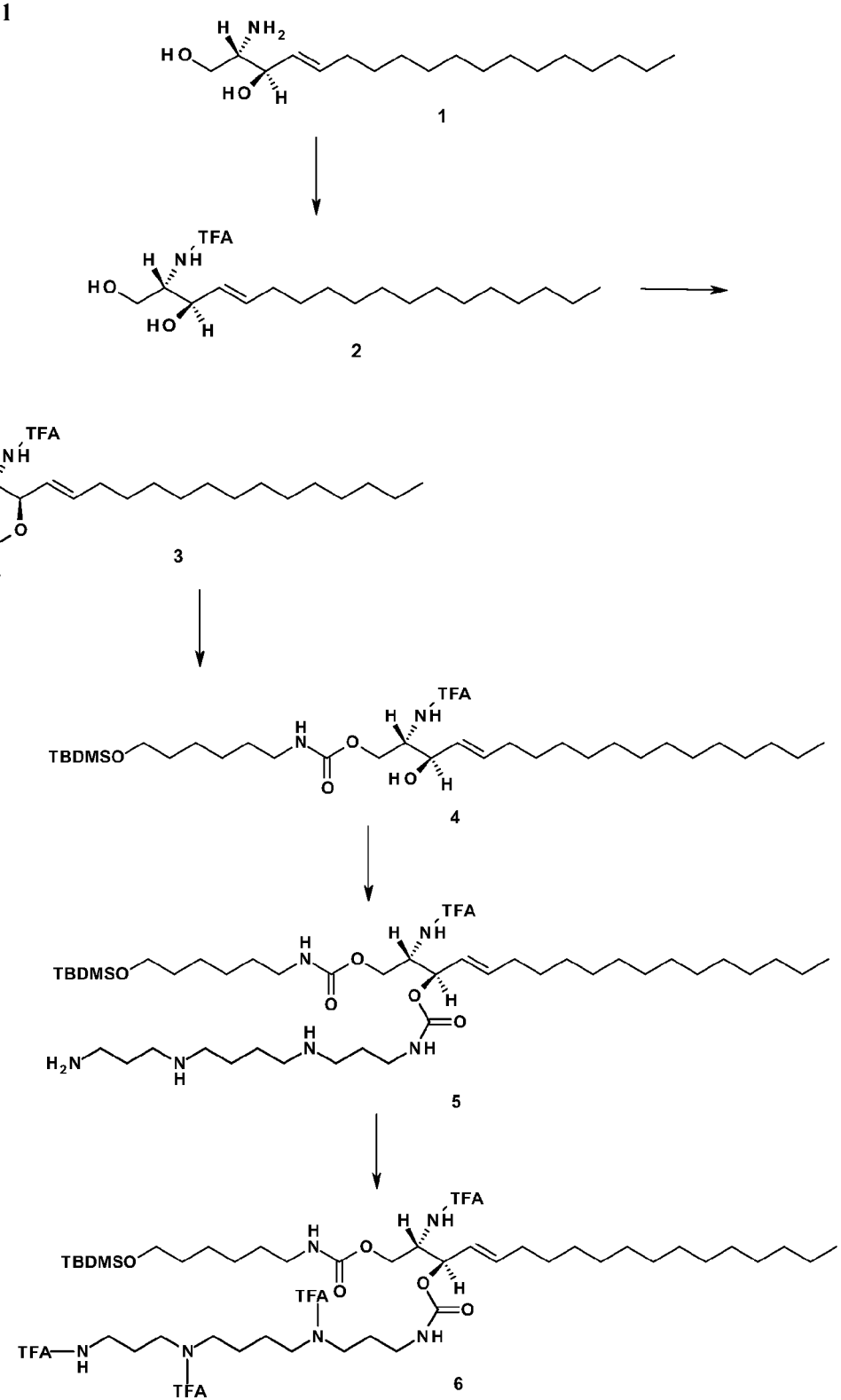
FIG. 1 provides the chemical synthesis pathway used to generate the sphingolipid-spermine phosphoramidite and sphingolipid spermidine phosphoramidite. A description of the synthesis is provided in Example 2, infra.
Figure 1:
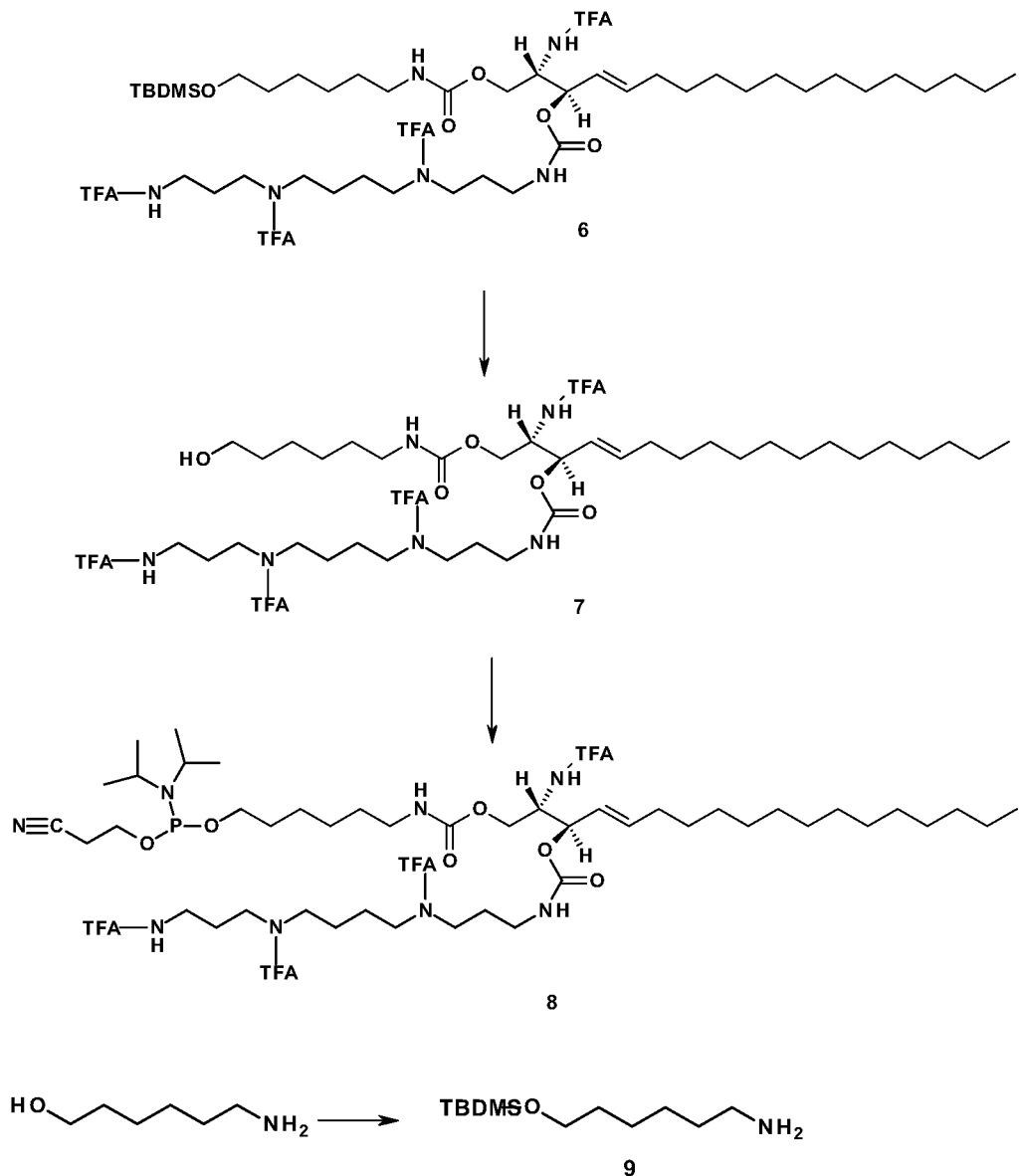

The compounds, methods, materials, and examples that will now be described are illustrative only and are not intended to be limiting; materials and methods similar or equivalent to those described herein can be used in practice or testing of the invention. Other features and advantages of the invention will be apparent from the following detailed description, and from the claims.

DETAILED DESCRIPTION OF THE INVENTION

Disclosed herein are sphingolipid-polyalkylamine derivatives useful in generating sphingolipid-polyalkylamine oligonucleotide compounds, the compounds useful for modulating expression of a target gene, particularly for down-regulating expression of a target gene. The compounds disclosed herein exhibit one or more of increased on-target activity, decreased off-target activity, enhanced uptake into cells accompanied with enhanced endosomal release into the cytoplasm, increased nuclease stability (exonuclease and or endonuclease), and reduced immunomodulation when compared to an unmodified double-stranded nucleic acid compound. Without wishing to be bound to theory, the presence of a sphingolipid-polyalkylamine provides stability to the oligonucleotide in body fluids, enhances cellular uptake and facilitates endosomal escape, by creation of a 'proton sponge effect' in the endosome. The molecules and compositions are able to down-regulate, knock down, attenuate, reduce or inhibit target gene expression and are useful in the treatment of subjects suffering from diseases or conditions and or symptoms associated with such diseases or conditions or at risk of contracting diseases or conditions in which gene expression has adverse consequences.

Accordingly, in certain aspects, modified dsRNA compounds and pharmaceutical compositions comprising same useful in down regulating gene expression are provided. The target gene is a mammalian or non-mammalian target gene.

Definitions

It is to be noted that, as used herein, the singular forms "a", "an" and "the" include plural forms unless the content clearly dictates otherwise. Where aspects or embodiments of the invention are described in terms of Markush groups or other grouping of alternatives, those skilled in the art will recognize that the invention is also thereby described in terms of any individual member or subgroup of members of the group.

The term "inhibit" as used herein refers to reducing the expression of a gene or the activity of the product of such gene to an extent sufficient to achieve a desired biological or physiological effect Inhibition is either complete or partial The terms "dsNA" and "ssNA" also includes saNA (short activating nucleic acid) molecules, which induce target gene expression at the transcriptional and/or post-transcriptional level. For example, activating NAs can induce potent transcriptional activation of associated genes by targeting gene promoters.

The dsNA molecules disclosed herein may be chemically or biologically synthesized, using techniques known to persons with skill in the art.

A "siNA inhibitor" "dsRNA inhibitor" "dsRNA molecule" is a compound which is capable of reducing the expression of a gene or the activity of the product of such gene to an extent sufficient to achieve a desired biological or physiological effect. The term "siNA inhibitor" as used herein refers to one or more of a siRNA, shRNA, synthetic shRNA; miRNA. Inhibition may also be referred to as down-regulation or, for RNAi, silencing. The dsRNA molecule includes a sense strand, also known as a passenger strand, which shares homology to a target RNA; and an antisense strand, also known as a guide strand, which is fully or partially complementary to the sense strand.

As used herein, the term "inhibition" of a target gene or "down-regulation of gene expression" means inhibition of gene expression (transcription or translation) or polypeptide activity. The polynucleotide sequence of the target RNA sequence, refers to a mRNA target, a RNA target or any homologous sequences thereof preferably having at least 70% identity, more preferably 80% identity, even more preferably 90% or 95% identity to the target mRNA or RNA. Therefore, polynucleotide sequences, which have undergone mutations, alterations or modifications as described herein are encompassed in the present invention. The terms "mRNA polynucleotide sequence" and "mRNA" are used interchangeably.

The term "target RNA" refers to an RNA molecule to which at least one strand of the dsNA or ssNA is homologous or complementary or to which a miRNA possesses homology. Target RNA molecule can be mRNA (messenger RNA) and lncRNA (long non-coding RNA) or lincRNA (large intergenic non-coding RNAs) including but not limited to naturally occurring antisense RNAs (AS RNA) and eRNA (enhancer RNA), as well as pre-miRNA or pro-miRNA. Unprocessed mRNA, ribosomal RNA, and viral RNA sequences may also be targets.

A target RNA is typically modulated by a dsNA or ssNA. Modulation usually refers to post-transcriptional downregulation (e.g. via RNAi or AS activity) or up-regulation (e.g. via anti-miR activity). In some embodiments, ss- or dsNA (single stranded or double stranded nucleic acids) can modulate their target RNA without affecting its levels but rather by modulating their function (e.g., anti-miRs that block miRNA activity). In other embodiments, target RNA is referred as a one which levels are affected by ssNA and/or dsNA in the absence of direct sequence homology between the NA and the target. This can happen e.g., in the case of RNAa when activation of target RNA expression is achieved at a transcriptional, rather than at a post-transcriptional, level.

As used herein, the terms "polynucleotide" and "nucleic acid" may be used interchangeably and refer to nucleotide sequences comprising deoxyribonucleic acid (DNA), and ribonucleic acid (RNA). The terms are to be understood to include, as equivalents, analogs of either RNA or DNA made from nucleotide analogs. Throughout this disclosure, mRNA sequences are set forth as representing the corresponding genes.

"Oligonucleotide" or "oligomer" refers to a deoxyribonucleotide or ribonucleotide sequence from about 2 to about 100 nucleotides or longer. In some embodiments the oligonucleotide is a mRNA. Each DNA or RNA nucleotide in the oligonucleotide may be independently natural or synthetic, and or modified or unmodified. Modifications include sugar, base and internucleotide modifications. An oligonucleotide as disclosed herein includes single-stranded molecules and double-stranded molecules, which modulate gene expression. Oligonucleotide includes antisense molecules (molecules which cleave via the RNAi or RNASEH mechanism and include DNA, RNA or DNA/RNA chimera), double stranded RNA (dsRNA) including siRNA, siNA, miRNA, saRNA, and the like, anti-miRs, miR mimetics, ribozymes, aptamers, exon skipping molecules, synthetic mRNA and the like. "Modulate gene expression" includes downregulating (e.g. siRNA) gene expression or upregulating (e.g. saRNA) gene expression.

As used herein, "linker" and "linkage" refer to one or more atoms that join one chemical moiety to another chemical moiety, for example the sphingolipid-polyalkylamine to the phosphoramidite or the sphingolipid-polyalkylamine to the oligonucleotide. The linker is a nucleotide or non-nucleotide agent comprising one atom or a chain of for example, 2, 3, 4, 5, 6, 7, 8, 9, 10, 11, 12, 13, 14, 15, 16, 17, 18, 19, or 20 atoms including carbon, oxygen, sulfur, nitrogen and phosphorus atoms or combinations thereof. Examples of linkers include relatively low molecular weight groups such as amide, ester, carbonate and ether, as well as higher molecular weight linking groups such as polyethylene glycol (PEG) as well as alkyl chains.

As used herein, the term "duplex region" refers to the region in the double stranded molecule in which two complementary or substantially complementary oligonucleotides form base pairs with one another, typically by Watson-Crick base pairing or by any other manner that allows for a duplex formation. For example, an oligonucleotide strand having 19, 20, 21, 22 nucleotide units can base pair with a complementary oligonucleotide of 19, 20, 21, 22 nucleotide units, or can base pair with 15, 16 17 or 18 nucleotides on each strand such that the "duplex region" consists of 15, 16 17 or 18 base pairs. The remaining base pairs may, for example, exist as 5' and 3' overhangs. Further, within the duplex region, 100% complementarity is not required; substantial complementarity is allowable within a duplex region.

As used herein, the term "halogen" includes fluoro, chloro, bromo, and iodo, and is preferably fluoro, chloro or bromo.

The term "$(C_7-C_{24})$alkyl" typically means a straight or branched hydrocarbon radical having 7-24 carbon atoms and includes, e.g., methyl, ethyl, n-propyl, isopropyl, n-butyl, sec-butyl, isobutyl, tert-butyl, n-pentyl, 2,2-dimethylpropyl, n-hexyl, n-heptyl, n-octyl, and the like. Preferred are ($C_{10}$-$C_{14}$)alkyl groups, most preferably methyl and ethyl. The terms "$(C_2-C_8)$alkenyl" and "$(C_2-C_8)$alkynyl" typically mean straight and branched hydrocarbon radicals having 2-8 carbon atoms and 1 double or triple bond, respectively, and include ethenyl, 3-buten-1-yl, 2-ethenylbutyl, 3-octen-1-yl, and the like, and propynyl, 2-butyn-1-yl, 3-pentyn-1-yl, and the like. $(C_2-C_6)$alkenyl and alkynyl radicals are preferred, more preferably $(C_2-C_4)$alkenyl and alkynyl.

The term "$(C_1-C_8)$alkylene" typically means a divalent straight or branched hydrocarbon radical having 1-8 carbon atoms and includes, e.g., methylene, ethylene, propylene, butylene, 2-methylpropylene, pentylene, 2-methylbutylene, hexylene, 2-methylpentylene, 3-methylpentylene, 2,3-dimethylbutylene, heptylene, octylene, and the like. Preferred are $(C_1-C_4)$alkylene, more preferably $(C_1-C_2)$alkylene.

A "coupling moiety" is a functional group that comprises a target for practical conjugation methods. Non-limiting examples of coupling moieties are as follows: phosphoramidites; amines (—$NH_2$), Carboxyls (—COOH) or activated carboxyls including NHS esters; Sulfhydryls (—SH) and disulfide bonds (—S—S—), which are reduced to sulfhydryls Carbonyls (—CHO) Cyano (—CN) Hydroxyl (—OH) Azides including aryl azides.

The term "amine protecting group" as used herein refers to a chemical moiety that can readily be attached to an amine group (and forming a protected amine) when desired to protect said amine from undesired chemical reactions and at a later point be removed from said protected amine to reveal the original amine. Examples of amine protecting groups can be found in references such as Green and Wuts (1991, Protective Groups in Organic Synthesis, Wiley, New York, 2nd Edition) and Bodansky (1993, Principles of Peptide Synthesis, Springer, Berlin). Examples of amine protecting groups include, without being limited to, acetyl, benzoyl, carbobenzyloxy, p-methoxybenzyl carbonyl, methoxycarbonyl, tert-butyloxycarbonyl, 9-fluorenylmethyloxycarbonyl (FMOC), benzyl, a carbamate group, p-methoxybenzyl, 3,4-dimethoxybenzyl (DMPM), p-methoxyphenyl (PMP), monomethoxytrityl (MMT), dimethoxytrityl (DMT), and tosyl.

The term "hydroxyl protecting group", also termed "alcohol protecting group", refers to a chemical moiety that can readily be attached to an hydroxyl group (and forming a protected hydroxy) when desired to protect said hydroxyl from undesired chemical reactions and at a later point be removed from said protected hydroxyl to reveal the original hydroxyl group. Examples of hydroxy protecting groups are well known in the art and can be found in references such as Green and Wuts (1991, Protective Groups in Organic Synthesis, Wiley, New York, 2nd Edition) and Bodansky (1993, Principles of Peptide Synthesis, Springer, Berlin). Non-limiting examples of hydroxyl protecting groups include 4,4'-dimethoxytrityl (DMT), tert-butyldimethylsilyl (TBDMS), tri-iso-propylsilyloxymethyl (TOM), trimethylsilyl (TMS), triisopropylsilyl (TIPS), acetyl, benzyl, and benzoyl.

The term "phosphate moiety" as used herein refers to a monophosphate moiety of the general formula —[O—P(O)(R')—O]$^{2-}$, a diphosphate moiety of the general formula —[O—P(O)(R')—O—P(O)(R')—O]$^{3-}$, or a triphosphate moiety of the general formula —[O—P(O)(R')—O—P(O)(R')—O—P(O)(R')—O]$^{4-}$, wherein R' each independently is O$^-$, S$^-$, BH$_3^-$, or N$^-$, preferably to such mono-, di- and tri-phosphate moieties wherein (i) R' each is O$^-$; or (ii) one of the R's, preferably the R' linked to the phosphate atom at position a, is S$^-$ or BH$_3^-$, and the other R's are O$^-$, as well as to any protonated form thereof. Preferred are monophosphate moieties as defined above, such as —[O—PO$_3$]$^{2-}$, —[O—PO$_2$S]$^{2-}$, and —[O—PO$_2$(BH$_3$)]$^{2-}$, more preferably —[O—PO$_3$]$^{2-}$.

The term "phosphate linking moiety" as used herein refers to a moiety of the general formula —[O—P(O)(R')]$^-$—, wherein R' is O$^-$, S$^-$, BH$_3^-$, or N$^-$, preferably O$^-$, S$^-$, or BH$_3^-$, more preferably O$^-$, as well as to a protonated form thereof.

The term "sphingolipid-polyalkylamine phosphoramidite" as used herein refers to a sphingolipid-polyalkylamine amidite derivative useful for covalently attaching a sphingolipid-polyalkylamine to a nucleotide.

The terms "sphingolipid-polyalkylamine oligonucleotide molecule" and "sphingolipid-polyalkylamine oligonucleotide compound" are interchangeable and refer to an oligonucleotide linked to a sphingolipid-polyalkylamine conjugate. In some non-limiting embodiments, the sphingolipid-polyalkylamine is a sphingolipid-spermine or a sphingolipid-spermidine.

The term "protecting group" refers to a chemical modification of a reactive/functional group that stabilizes the reactive/functional group. Examples of protecting groups used in oligonucleotide synthesis include DMT to protect the 5' hydroxyl or TBDMS (t-butyldimethylsilyl) or TOM (tri-iso-propylsilyloxymethyl) to protect the 2'-hydroxy group. TFA protects labile amine groups.

The various nucleoside analogs disclosed herein may be synthesized according to any suitable technology or procedure known in the art, and preferably include amine and or hydroxy protecting groups present during the synthesis steps.

In some embodiments the oligonucleotide is a single-stranded oligonucleotide such as an antisense molecule. In some embodiments the oligonucleotide is an antisense molecule. In some embodiments the antisense molecule comprising DNA. In other embodiments the antisense oligonucleotide is a DNA/RNA chimera, for example as disclosed in U.S. Pat. Nos. 6,410,323 and 6,426,220.

In some embodiments the oligonucleotide is a double-stranded oligonucleotide such as siRNA, shRNA or miRNA. In some embodiments the double-stranded molecule further comprises at least one 2'O alkyl sugar modified ribonucleotide. In certain embodiments the 2'O-alkyl sugar modified ribonucleotide comprises a 2'O-methyl (methoxy) sugar modification or a 2'methoxyethyl (2'MOE) sugar modification. Other antisense modifications include internucleotide linkage modifications including phosphorothioate linkages.

According to one aspect provided herein are sphingolipid-polyalkylamine oligonucleotide dsRNA molecules comprising unmodified and modified ribonucleotides (e.g. 2'O-methyl (2' OMe) or 2' deoxy, 2' fluoro (2'Fl) sugar modified ribonucleotides), optionally at least one unconventional moiety and at least one sphingolipid-polyalkylamine moiety. In some embodiments the chemically modified dsRNA comprises at least one modified nucleotide selected from the group consisting of a sugar modification, a base modification and an internucleotide linkage modification. In some embodiments a modified ribonucleotide is a 2'OMe sugar modified ribonucleotide. In some embodiments some or all of the pyrimidine ribonucleotides in the antisense strand comprise 2'OMe sugar modified ribonucleotides. In some embodiments some or all of the purines in the antisense strand comprise 2'OMe sugar modified ribonucleotides. In preferred embodiments the antisense strand comprises 2'OMe sugar modified ribonucleotides in nuclease sensitive positions. In preferred embodiments the antisense strand comprises 2'Fl sugar modified ribonucleotides in nuclease sensitive positions. In some embodiments the sense strand comprises 2'OMe sugar modified ribonucleotides in nuclease sensitive positions. In some embodiments the sense strand (e.g. (N')y) comprises one or more 2'OMe sugar modified ribonucleotides. In some embodiments the sense strand comprises one or more deoxyribonucleotide. In some embodiments the siRNA is blunt ended at the 3' terminus of the compound, i.e. the dsRNA or siRNA is blunt ended on the end defined by the 3'-terminus of the sense or passenger strand and the 5'-terminus of antisense or guide strand. In some embodiments the 3'terminus comprises a 3'Pi (3' terminal phosphate). In some embodiments the 5'terminus comprises a 5'Pi (5' terminal phosphate).

In some embodiments the double-stranded molecule further comprises at least one modified ribonucleotide selected from the group consisting of a ribonucleotide having a sugar modification, a base modification or an internucleotide linkage modification and may contain one or more unconventional moiety including DNA, TNA (threose nucleic acid), LNA (locked nucleic acid), ENA (ethylene-bridged nucleic acid), L-DNA or L-RNA, PNA (peptide nucleic acid), arabinoside, phosphonocarboxylate or phosphinocarboxylate nucleotide (PACE nucleotide), or nucleotides with a 6 carbon sugar. All analogs of, or modifications to, a nucleotide/oligonucleotide are employed with the molecules described herein, provided that said analog or modification does not substantially adversely affect the properties, e.g. function, of the nucleotide/oligonucleotide.

In some embodiments nucleotides are selected from those having naturally occurring or synthetic modified bases. Naturally occurring bases include adenine, guanine, cytosine, thymine and uracil. Modified bases of nucleotides include pyrazolotriazine, inosine, xanthine, hypoxanthine, 2-aminoadenine, 6-methyl, 2-propyl and other alkyl adenines, 5-halouracil, 5-halocytosine, 6-azacytosine and 6-az thymine, pseudouracil, deoxypseudouracil, 4-thiouracil, ribo-2-thiouridine, ribo-4-thiouridine, 8-haloadenine, 8-aminoadenine, 8-thioladenine, 8-thiolalkyl adenines, 8-hydroxyl adenine and other 8-substituted adenines, 8-haloguanines, 8-aminoguanine, 8-thiolguanine, 8-thioalkylguanines 8-hydroxylguanine and other substituted guanines, other aza and deaza adenines, other aza and deaza guanines, 5-methylribouridine, 5-trifluoromethyl uracil, 5-methylribocytosine, and 5-trifluorocytosine. In some embodiments one or more nucleotides in an oligomer is substituted with inosine.

Modified deoxyribonucleotide includes, for example 5'OMe DNA (5-methyl-deoxyriboguanosine-3'-phosphate); PACE (deoxyriboadenosine 3' phosphonoacetate, deoxyribocytidine 3' phosphonoacetate, deoxyriboguanosine 3' phosphonoacetate, deoxyribothymidine 3' phosphonoacetate).

Bridged nucleic acids include LNA (2'-O, 4'-C-methylene bridged Nucleic Acid adenosine 3' monophosphate, 2'-O,4'-C-methylene bridged Nucleic Acid 5-methyl-cytidine 3' monophosphate, 2'-O,4'-C-methylene bridged Nucleic Acid guanosine 3' monophosphate, 5-methyl-uridine (or thymidine) 3' monophosphate); and ENA (2'-O,4'-C-ethylene bridged Nucleic Acid adenosine 3' monophosphate, 2'-O,4'-C-ethylene bridged Nucleic Acid 5-methyl-cytidine 3' monophosphate, 2'-O,4'-C-ethylene bridged Nucleic Acid guanosine 3' monophosphate, 5-methyl-uridine (or thymidine) 3' monophosphate).

A sugar modification includes a modification on the 2' moiety of the sugar residue and encompasses amino, fluoro, alkoxy (e.g. methoxy), alkyl, amino, fluoro, chloro, bromo, CN, CF, imidazole, carboxylate, thioate, $C_1$-$C_{10}$ lower alkyl, substituted lower alkyl, alkaryl or aralkyl, $OCF_3$, OCN, O-, S-, or N-alkyl; O-, S-, or N-alkenyl; $SOCH_3$; $SO_2CH_3$; $ONO_2$; $NO_2$, $N_3$; heterocycloalkyl; heterocycloalkaryl; aminoalkylamino; polyalkylamino or substituted silyl, as, among others, described in European patents EP 0 586 520 B1 or EP 0 618 925 B1.

In one embodiment the modified molecules comprise at least one ribonucleotide comprising a 2' modification on the sugar moiety ("2' sugar modification"). In certain embodiments the sugar modified moiety comprises 2'O-alkyl or 2'-fluoro or 2'O-allyl or any other 2' modification. In some embodiments a preferred 2'O-alkyl is 2'O-methyl (methoxy) sugar modification. Other stabilizing modifications are also possible (e.g. terminal modifications).

In some embodiments the backbone of the oligonucleotides is modified and comprises phosphate-D-ribose entities but may also contain thiophosphate-D-ribose entities, triester, thioate, 2'-5' bridged backbone (also may be referred to as 2'5' linked nucleotide or 5'-2'), PACE and the like. Additional modifications include reversible or labile phosphotriester linkages such as those disclosed in US2009093425 and US2011294869, respectively.

As used herein, the terms "non-pairing nucleotide analog" means a nucleotide analog which comprises a non-base pairing moiety including but not limited to: 6 des amino adenosine (Nebularine), 4-Me-indole, 3-nitropyrrole, 5-nitroindole, Ds, Pa, N3-Me riboU, N3-Me riboT, N3-Me dC, N3-Me-dT, N1-Me-dG, N1-Me-dA, N3-ethyl-dC, N3-Me dC. In some embodiments the non-base pairing nucleotide analog is a ribonucleotide (2'OH). In other embodiments the non-base pairing nucleotide analog is a deoxyribonucleotide (2'H). In addition, analogs of polynucleotides may be prepared wherein the structure of one or more nucleotide is fundamentally altered and better suited as therapeutic or experimental reagents. An example of a nucleotide analog is a peptide nucleic acid (PNA) wherein the deoxyribose (or ribose) phosphate backbone in DNA (or RNA) is replaced with a polyamide backbone which is similar to that found in peptides. PNA analogs have been shown to be resistant to enzymatic degradation and to have enhanced stability in vivo and in vitro. Other modifications include polymer backbones, cyclic backbones, acyclic backbones, thiophosphate-D-ribose backbones, triester backbones, thioate backbones, 2'-5' bridged backbone, artificial nucleic acids, morpholino nucleic acids, glycol nucleic acid (GNA), threose nucleic acid (TNA), arabinoside, and mirror nucleoside (for example, beta-L-deoxyribonucleoside instead of beta-D-deoxyribonucleoside). Examples of siRNA compounds comprising LNA nucleotides are disclosed in Elmen et al., (NAR 2005, 33(1):439-447).

Other modifications include 3' terminal modifications also known as capping moieties. Such terminal modifications are selected from the group consisting of a nucleotide, a modified nucleotide, a lipid, a peptide, a sugar and inverted abasic moiety. Such modifications are incorporated, for example at the 3' terminus of the sense and/or antisense strands.

The term "capping moiety" as used herein includes abasic ribose moiety, abasic deoxyribose moiety, modifications abasic ribose and abasic deoxyribose moieties including 2' O alkyl modifications; inverted abasic ribose and abasic deoxyribose moieties and modifications thereof; C6-imino-Pi; a mirror nucleotide including L-DNA and L-RNA; 5'O-Me nucleotide; and nucleotide analogs including 4',5'-methylene nucleotide; 1-(β-D-erythrofuranosyl)nucleotide; 4'-thionucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties.

Certain preferred capping moieties are abasic ribose or abasic deoxyribose moieties; inverted abasic ribose or abasic deoxyribose moieties; C6-amino-Pi; a mirror nucleotide including L-DNA and L-RNA. In some embodiments the molecules are synthesized with one or more inverted nucleotides, for example inverted thymidine or inverted adenosine (see, for example, Takei, et al., 2002, JBC 277(26):23800-06). In some embodiments an inverted abasic deoxyribose moiety is covalently attached to the 5' terminus of the sense strand (N')y.

"Terminal functional group" includes halogen, alcohol, amine, carboxylic, ester, amide, aldehyde, ketone, ether groups.

The term "unconventional moiety" as used herein refers to abasic ribose moiety, an abasic deoxyribose moiety, a deoxyribonucleotide, a modified deoxyribonucleotide, a mirror nucleotide, a non-base pairing nucleotide analog and a nucleotide joined to an adjacent nucleotide by a 2'-5' internucleotide phosphate bond; a pyrazolotriazine nucleotide analog; a threose nucleic acid (TNA) moiety; unlocked nucleic acids (UNA), bridged nucleic acids including locked nucleic acids (LNA) and ethylene bridged nucleic acids (ENA) and morpholinos.

"TNA" refers to (L)-alpha-threofuranosyl nucleotides. The TNA phosphoramidites are linked to adjacent TNA, deoxyribonucleotide or ribonucleotide by (3'-->2') phosphodiester linkages. TNA comprise a four-carbon sugar (Schoning, et al Science 2000. 290:1347-51). In some embodiments, in addition to TNA the siRNA compound further comprises at least one modified ribonucleotide selected from the group consisting of a ribonucleotide having a sugar modification, a base modification or an internucleotide linkage modification and may contain DNA, a mirror nucleotide (L-DNA, L-RNA) and modified nucleotides such as LNA (locked nucleic acid), ENA (ethylene-bridged nucleic acid), PNA (peptide nucleic acid), arabinoside, phosphonocarboxylate or phosphinocarboxylate nucleotide (PACE nucleotide), or nucleotides with a 6 carbon sugar.

What is sometimes referred to herein as an "abasic nucleotide" or "abasic nucleotide analog" is more properly referred to as a pseudo-nucleotide or an unconventional moiety. A nucleotide is a monomeric unit of nucleic acid, consisting of a ribose or deoxyribose sugar, a phosphate, and a base (adenine, guanine, thymine, or cytosine in DNA; adenine, guanine, uracil, or cytosine in RNA). A modified nucleotide comprises a modification in one or more of the sugar, phosphate and or base. The abasic pseudo-nucleotide lacks a base, and thus is not strictly a nucleotide. Abasic deoxyribose moiety includes for example abasic deoxyribose-3'-phosphate; 1,2-dideoxy-D-ribofuranose-3-phosphate; 1,4-anhydro-2-deoxy-D-ribitol-3-phosphate. Inverted abasic deoxyribose moiety includes inverted deoxyriboabasic; 3',5' inverted deoxyabasic 5'-phosphate.

A "mirror" nucleotide is a nucleotide with reversed chirality to the naturally occurring or commonly employed nucleotide, i.e., a mirror image (L-nucleotide) of the naturally occurring (D-nucleotide), also referred to as L-RNA in the case of a mirror ribonucleotide, and "spiegelmer". The mirror nucleotide is a ribonucleotide or a deoxyribonucleotide and my further comprise at least one sugar, base and or backbone modification. See U.S. Pat. No. 6,586,238. Also, U.S. Pat. No. 6,602,858 discloses nucleic acid catalysts comprising at least one L-nucleotide substitution. Mirror nucleotide includes for example L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror dT) and L-RNA (L-riboadenosine-3'-phosphate (mirror rA); L-ribocytidine-3'-phosphate (mirror rC); L-riboguanosine-3'-phosphate (mirror rG); L-ribouridine-3'-phosphate (mirror dU).

In some embodiments, a modified ribonucleotide is a 2'OMe sugar modified ribonucleotide. In some embodiments, some or all of the pyrimidine ribonucleotides in the antisense strand comprise 2'OMe sugar modified ribonucleotides. In some embodiments some or all of the purines in the antisense strand comprise 2'OMe sugar modified ribonucleotides. In preferred embodiments the antisense strand comprises 2'OMe sugar modified ribonucleotides in nuclease sensitive positions. In some embodiments the sense strand comprises 2'OMe sugar modified ribonucleotides in nuclease sensitive positions. In some embodiments the sense strand [e.g. (N')y] comprises one or more 2'OMe sugar modified ribonucleotides. In some embodiments the sense strand comprises one or more deoxyribonucleotide. In some embodiments the siRNA is blunt ended at the 3' terminus of the compound, i.e. the dsRNA or siRNA is blunt ended on the end defined by the 3'-terminus of the sense or passenger strand and the 5'-terminus of antisense or guide strand.

In other embodiments at least one of the two strands has a 3' overhang of at least one nucleotide at the 3'-terminus; the overhang comprises at least one deoxyribonucleotide. At least one of the strands optionally comprises an overhang of at least one nucleotide at the 3'-terminus. The overhang consists of from about 1 to about 5 nucleotides.

In various embodiments the overhangs are independently selected from a nucleotide, a non-nucleotide and a combination thereof. In some embodiments each of Z and/or Z' independently includes a C2, C3, C4, C5 or C6 alkyl moiety, optionally a C3 [propane, —(CH2)$_3$-] moiety or a derivative thereof including propanol (C3-OH), propanediol, and phosphodiester derivative of propanediol ("C3Pi"). In preferred embodiments each of Z and/or Z' includes two hydrocarbon moieties and in some examples is C3Pi-C3OH or C3Pi-C3Pi. Each C3 is covalently conjugated to an adjacent C3 via a covalent bond, preferably a phospho-based bond. In some embodiments the phospho-based bond is a phosphorothioate, a phosphonoacetate or a phosphodiester bond.

In a specific embodiment $x=y=19$ and Z comprises C3-C3. In some embodiments the C3-C3 overhang is covalently attached to the 3' terminus of (N)x or (N')y via a covalent linkage, for example a phosphodiester linkage. In some embodiments the linkage between a first C3 and a second C3 is a phosphodiester linkage. In some embodiments the 3' non-nucleotide overhang is C3Pi-C3Pi. In some embodiments the 3' non-nucleotide overhang is C3Pi-C3Ps. In some embodiments the 3' non-nucleotide overhang is C3Pi-C3OH (OH is hydroxy). In some embodiments the 3' non-nucleotide overhang is C3Pi-C3OH.

In various embodiments the alkyl moiety comprises an alkyl derivative including a C3 alkyl, C4 alkyl, C5 alky or C6 alkyl moiety comprising a terminal hydroxyl, a terminal amino, or terminal phosphate group. In some embodiments the alkyl moiety is a C3 alkyl or C3 alkyl derivative moiety. In some embodiments the C3 alkyl moiety comprises propanol, propylphosphate, propylphosphorothioate or a combination thereof The C3 alkyl moiety is covalently linked to the 3' terminus of (N')y and/or the 3' terminus of (N)x via a phosphodiester bond. In some embodiments the alkyl moiety comprises propanol, propyl phosphate or propyl phosphorothioate.

In other embodiments at least one of the two strands has a 3' overhang of at least one nucleotide at the 3'-terminus; the overhang comprises at least one deoxyribonucleotide. At least one of the strands optionally comprises an overhang of at least one nucleotide at the 3'-terminus. The overhang consists of from about 1 to about 5 nucleotides.

The length of the RNA duplex is from about 15 to about 49 ribonucleotides, or about, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49, preferably 18-40, 18-27, 18-25 or 19 to 23 ribonucleotides. In some embodiments the length of each strand (oligomer) is independently selected from the group consisting of about 18 to about 40 nucleotides, preferably 18 to 27, 18 to 25, 19-23 and more preferably 19 ribonucleotides.

In some embodiments, the complementarity between the antisense strand of the dsRNA and the target nucleic acid is perfect. In other embodiments, the antisense strand of the modified siRNA compound and the target nucleic acid are substantially complementary, i.e. having one, two or up to three mismatches between said antisense strand and the target nucleic acid. In some embodiments the antisense strand is mismatched to the target mRNA at the 5' terminal nucleotide.

In certain embodiments the complementarity between the antisense strand and the sense strand of the dsRNA molecule is perfect. In some embodiments, the strands are substantially complementary, i.e. having one, two or up to three mismatches between said antisense strand and said sense strand. In some embodiments the antisense strand is fully complementary to the sense strand.

Oligonucleotides

Antisense

By the term "antisense" (AS) or "antisense fragment" is meant an oligonucleotide fragment (comprising either deoxyribonucleotides, ribonucleotides or a mixture of both) having inhibitory antisense activity, said activity causing a decrease in the expression of the endogenous genomic copy of a target gene. The sequence of the AS is designed to complement a target mRNA of interest and form an RNA:AS duplex. This duplex formation can prevent processing, splicing, transport or translation of the relevant mRNA. Moreover, certain AS nucleotide sequences can elicit cellular RNase H activity when hybridized with their target mRNA, resulting in mRNA degradation (Calabretta et al, 1996: Antisense strategies in the treatment of leukemias. Semin Oncol. 23(1):78-87). In that case, RNase H will cleave the RNA component of the duplex and can potentially release the AS to further hybridize with additional molecules of the target RNA. An additional mode of action results from the interaction of AS with genomic DNA to form a triple helix which can be transcriptionally inactive.

Many reviews have covered the main aspects of antisense (AS) technology and its therapeutic potential (see for example, Wright & Anazodo, 1995. Antisense Molecules and Their Potential For The Treatment Of Cancer and AIDS. Cancer J. 8:185-189; Scanlon et al., 1995 Oligonucleotides-mediated modulation of mammalian gene expression. FASEB J. 9:1288; Gewirtz, 1993. Oligodeoxynucleotide-based therapeutics for human leukemias, Stem Cells Dayt. 11:96).

The sequence target segment for the antisense oligonucleotide is selected such that the sequence exhibits suitable energy related characteristics important for oligonucleotide duplex formation with their complementary templates, and shows a low potential for self-dimerization or self-complementation (Anazodo et al., 1996). For example, the computer program OLIGO (Primer Analysis Software, Version 3.4), can be used to determine antisense sequence melting temperature, free energy properties, and to estimate potential self-dimer formation and self-complimentary properties. The program allows the determination of a qualitative estimation of these two parameters (potential self-dimer formation and self-complimentary) and provides an indication of "no potential" or "some potential" or "essentially complete potential". Using this program target segments are generally selected that have estimates of no potential in these parameters. However, segments can be used that have "some potential" in one of the categories. A balance of the parameters is used in the selection as is known in the art. Further, the oligonucleotides are also selected as needed so that analogue substitution do not substantially affect function.

Phosphorothioate antisense oligonucleotides do not normally show significant toxicity at concentrations that are effective and exhibit sufficient pharmacodynamic half-lives in animals (Agrawal, 1996. Antisense oligonucleotides: towards clinical trials, TIBTECH, 14:376) and are nuclease resistant.

Single stranded oligonucleotides have been shown to work in RNAi, see for example Lima et al., (2012) Cell 150:883-894 and the preview by Davidson and Monteys (2012) Cell 150:873-875.

RNAi Oligonucleotides

The presence of long dsRNAs in cells stimulates the activity of a ribonuclease III enzyme referred to as "dicer" (Bass, 2000, Cell, 101, 235; Zamore et al., 2000, Cell, 101, 25-33; Hammond et al., 2000, Nature, 404, 293). Dicer is involved in the processing of the dsRNA into short dsRNA pieces known as siNA or siRNA (Zamore et al., 2000, Cell, 101, 25-33; Bass, 2000, Cell, 101, 235; Berstein et al., 2001, Nature, 409, 363). Short interfering RNAs derived from dicer activity are typically about 21 to about 23 nucleotides in length and include about 19 base pair duplexes (Zamore et al., 2000, Cell, 101, 25-33; Elbashir et al., 2001, Genes Dev., 15, 188). Dicer has also been implicated in the excision of 21- and 22-nucleotide small temporal RNAs (stRNAs) from precursor RNA of conserved structure that are implicated in translational control (Hutvagner et al., 2001, Science, 293, 834). The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex (Elbashir et al., 2001, Genes Dev., 15, 188).

RNAi has been studied in a variety of systems. Fire et al., 1998, Nature, 391, 806, were the first to observe RNAi in C. elegans. Bahramian and Zarbl, 1999, Molecular and Cellular Biology, 19, 274-283 and Wianny and Goetz, 1999, Nature Cell Biol., 2, 70, describe RNAi mediated by dsRNA in mammalian systems. Hammond et al., 2000, Nature, 404, 293, describe RNAi in Drosophila cells transfected with dsRNA. Elbashir et al., 2001, Nature, 411, 494 and Tuschl et al., International PCT Publication No. WO 01/75164, describe RNAi induced by introduction of duplexes of synthetic 21-nucleotide RNAs in cultured mammalian cells including human embryonic kidney and HeLa cells. Research in Drosophila embryonic lysates (Elbashir et al., 2001, EMBO J., 20, 6877 and Tuschl et al., International PCT Publication No. WO 01/75164) has revealed certain requirements for siRNA length, structure, chemical composition, and sequence that are essential to mediate efficient RNAi activity.

Nucleic acid molecules (for example having structural features as disclosed herein) may inhibit or down regulate gene expression or viral replication by mediating RNA interference "RNAi" or gene silencing in a sequence-specific manner; see e.g., Zamore et al., 2000, Cell, 101, 25-33; Bass, 2001, Nature, 411, 428-429; Elbashir et al., 2001, Nature, 411, 494-498; and Kreutzer et al., International PCT Publication No. WO 00/44895; Zernicka-Goetz et al., International PCT Publication No. WO 01/36646; Fire, International PCT Publication No. WO 99/32619; Mello and Fire, International PCT Publication No. WO 01/29058; Li et al., International PCT Publication No. WO 00/44914; Hutvagner and Zamore, 2002, Science, 297, 2056-60; McManus et al., 2002, RNA, 8, 842-850.

The selection and synthesis of siRNA corresponding to known genes has been widely reported; (see for example Ui-Tei et al., J Biomed Biotech. 2006; 2006: 65052; Chalk et al., BBRC. 2004, 319(1): 264-74; Sioud & Leirdal, Met. Mol Biol.; 2004, 252:457-69; Levenkova et al., Bioinform. 2004, 20(3):430-2; Ui-Tei et al., NAR. 2004, 32(3):936-48; De Paula et al., RNA 2007, 13:431-56).

For examples of the use of, and production of, modified siRNA see, for example, Braasch et al., Biochem. 2003, 42(26):7967-75; Chiu et al., RNA, 2003, 9(9):1034-48; PCT publications WO 2004/015107 (atugen AG) and WO 02/44321 (Tuschl et al). U.S. Pat. Nos. 5,898,031 and 6,107,094, describe chemically modified oligomers. US Patent Publication Nos. 2005/0080246 and 2005/0042647 relate to oligomeric compounds having an alternating motif and nucleic acid molecules having chemically modified internucleoside linkages, respectively.

Other modifications have been disclosed. The inclusion of a 5'-phosphate moiety was shown to enhance activity of siRNAs in *Drosophila* embryos (Boutla, et al., Curr. Biol. 2001, 11:1776-1780) and is required for siRNA function in human HeLa cells (Schwarz et al., Mol. Cell, 2002, 10:537-48). Amarzguioui et al., (NAR, 2003, 31(2):589-95) showed that siRNA activity depended on the positioning of the 2'-O-methyl modifications. Holen et al (NAR. 2003, 31(9): 2401-07) report that an siRNA having small numbers of 2'-O-methyl modified nucleosides gave good activity compared to wild type but that the activity decreased as the numbers of 2'-O-methyl modified nucleosides was increased. Chiu and Rana (RNA. 2003, 9:1034-48) describe that incorporation of 2'-O-methyl modified nucleosides in the sense or antisense strand (fully modified strands) severely reduced siRNA activity relative to unmodified siRNA. The placement of a 2'-O-methyl group at the 5'-terminus on the antisense strand was reported to severely limit activity whereas placement at the 3'-terminus of the antisense and at both termini of the sense strand was tolerated (Czauderna et al., NAR. 2003, 31(11):2705-16; WO 2004/015107). The molecules of the disclosed herein offer an advantage in that they are stable and active and are useful in the preparation of pharmaceutical compositions for treatment of various diseases.

PCT Patent Publication Nos. WO 2008/104978, WO 2009/044392, WO 2011/066475 and WO 2011/084193 to a co-assignee of the present invention and hereby incorporated by reference in their entirety, disclose dsRNA structures.

PCT Publication No. WO 2008/050329 and U.S. Ser. No. 11/978,089 to a co-assignee of the present invention relate to inhibitors of pro-apoptotic genes, and are incorporated by reference in their entirety.

PCT Patent Publication Nos. WO 2004/111191 and WO 2005/001043 relate to methods for enhancing RNAi.

The role of microRNAs in cancer is being actively researched and novel targets for gene modulation are continuously being identified, see for example Iorio and Croce (2012) EMBO Mol Med 4:143-159 and Chen et al, (2012) J. Biomed. Sci. 19:90.

Provided herein is a method of modulating the expression of target gene by at least 20%, 30%, 40% or 50% as compared to a control, comprising contacting an mRNA transcript of the target gene with one or more of the sphingolipid-polyalkylamine oligonucleotide compounds disclosed herein.

Further provided is one or more of the sphingolipid-polyalkylamine oligonucleotide compounds disclosed herein for use in modulating the expression of target gene by at least 20%, 30%, 40% or 50% as compared to a control.

Further provided is the use of one or more of the sphingolipid-polyalkylamine oligonucleotide compounds disclosed herein for the manufacture of a medicament for modulating the expression of target gene by at least 20%, 30%, 40% or 50% as compared to a control.

Additionally provided herein is a method of modulating the expression of target gene in a mammal by at least 20%, 30%, 40% or 50% as compared to a control, comprising administering one or more of the sphingolipid-polyalkylamine oligonucleotide molecules disclosed herein to the mammal.

Additionally provided herein is one or more of the sphingolipid-polyalkylamine oligonucleotide molecules disclosed herein for use in modulating the expression of target gene in a mammal by at least 20%, 30%, 40% or 50% as compared to a control.

Additionally provided herein is the use of one or more of the sphingolipid-polyalkylamine oligonucleotide molecules disclosed herein in the manufacture of a medicament for modulating the expression of target gene in a mammal by at least 20%, 30%, 40% or 50% as compared to a control.

In some preferred embodiments, the mammal is a human.

Modulating gene expression is down-regulating gene expression or up-regulating gene expression. In some embodiments, modulating gene expression is up regulating gene expression. In some preferred embodiments, modulating gene expression is down regulating gene expression. In some embodiments, down regulating gene expression occurs by way of RNAi.

In various embodiments the down-regulation of the expression of a target gene is selected from the group consisting of down-regulation of gene function (which is examined, e.g. by an enzymatic assay or a binding assay with a known interactor of the native gene/polypeptide, inter alia), down-regulation of polypeptide product of the gene (which is examined, e.g. by Western blotting, ELISA or immuno-precipitation, inter alia) and down-regulation of mRNA expression of the gene (which is examined, e.g. by Northern blotting, quantitative RT-PCR, in-situ hybridization or microarray hybridization, inter alia).

In other embodiments modulation is up-regulation and the up-regulation of the expression of a target gene is selected from the group comprising up-regulation of gene function (which is examined, e.g. by an enzymatic assay or a binding assay with a known interactor of the native gene/polypeptide, inter alia), up-regulation of polypeptide product of the gene (which is examined, e.g. by Western blotting, ELISA or immuno-precipitation, inter alia) and up-regulation of mRNA expression of the gene (which is examined, e.g. by Northern blotting, quantitative RT-PCR, in-situ hybridization or microarray hybridization, inter alia).

In preferred embodiments the oligonucleotide useful for conjugation to the sphingolipid-polyalkylamine is a RNA interference (RNAi) oligonucleotide. A RNAi oligonucleotide is a nucleic acid based molecule capable of inducing RNA interference through interaction with the RNA interference pathway machinery of mammalian cells to degrade or inhibit translation of messenger RNA (mRNA) transcripts of a transgene in a sequence specific manner. Two primary RNAi oligonucleotide are small (or short) interfering RNAs (siRNA) and micro RNAs (miRNA or miR). RNAi oligonucleotides may be for example, RNA antisense, siRNA, siNA, miRNA, double-strand RNA (dsRNA), short hairpin RNA (shRNA). RNAi oligonucleotides may be chemically synthesized using standard synthesizers or recombinantly synthesized using expression cassettes encoding RNA capable of inducing RNAi. In some embodiments the oligonucleotide is a single-stranded oligonucleotide or a double-stranded oligonucleotide. Single-stranded oligonucleotides include antisense molecules (DNA, RNA or DNA/RNA chimeras) and miRNA mimetics. Double-stranded oligonucleotides include siRNA, siNA, shRNA and miRNA.

RNAi oligonucleotides may be chemically synthesized using standard synthesizers or recombinantly synthesized using expression cassettes encoding RNA capable of inducing RNAi. RNAi polynucleotide expression cassettes can be transcribed in the cell to produce small hairpin RNAs that can function as siRNA, separate sense and anti-sense strand linear siRNAs, or miRNA. RNA polymerase III transcribed DNAs contain promoters selected from the list comprising: U6 promoters, H1 promoters, and tRNA promoters. RNA polymerase II promoters include U1, U2, U4, and U5 promoters, snRNA promoters, microRNA promoters, and mRNA promoters.

siRNA comprises a double stranded structure typically containing 15-49 base pairs and preferably 18-25 base pairs and having a nucleotide sequence identical (perfectly complementary) or nearly identical (partially complementary) to a coding sequence in an expressed target gene or RNA within the cell. A siRNA may have dinucleotide 3' overhangs. A siRNA may be composed of two annealed polynucleotides or a single polynucleotide that forms a hairpin structure. A siRNA molecule of the invention comprises a sense region and an antisense region. In one embodiment, the siRNA of the conjugate is assembled from two oligonucleotide fragments wherein one fragment comprises the nucleotide sequence of the antisense strand of the siRNA molecule and a second fragment comprises nucleotide sequence of the sense region of the siRNA molecule. In another embodiment, the sense strand is connected to the antisense strand via a linker molecule, such as a polynucleotide linker or a non-nucleotide linker MicroRNAs (miR-NAs) are small noncoding RNA gene products about 22 nucleotides long that direct destruction or translational repression of their mRNA targets. If the complementarity between the miRNA and the target mRNA is partial, translation of the target mRNA is repressed. If complementarity is extensive, the target mRNA is cleaved. For miRNAs, the complex binds to target sites usually located in the 3' UTR of mRNAs that typically share only partial homology with the miRNA. A "seed region"—a stretch of about seven (7) consecutive nucleotides on the 5' end of the miRNA that forms perfect base pairing with its target—plays a key role in miRNA specificity. Binding of the RISC/miRNA complex to the mRNA can lead to either the repression of protein translation or cleavage and degradation of the mRNA. Recent data indicate that mRNA cleavage happens preferentially if there is perfect homology along the whole length of the miRNA and its target instead of showing perfect base-pairing only in the seed region (Pillai et al. 2007).

Exemplary Sphingolipid-Polyalkylamine Oligonucleotides

The examples provided below have a duplex region of 19 nucleotides; however, nucleic acid molecules disclosed herein can have a duplex region anywhere between 15 and 49 nucleotides, or between 18 and 40 nucleotides and where each strand is independently between 18 and 40 nucleotides in length. In each duplex the antisense strand (N)x is shown on top. "SL" refers to a sphingolipid-polyalkylamine conjugate. Non-limiting examples of sphingolipid-polyalkylamine-oligonucleotide (double stranded nucleic acid molecule) have the following structure: Non-limiting examples of sphingolipid-polyalkylamine-dsRNA molecule have the following structure (upper strand 5'>3' represents antisense strand, lower strand 3'>5" represents sense strand):

5' $(N)_{19}$
3' SL-$(N')_{19}$
5' $(N)_{19}$
3' $(N')_{19}$-SL
5' $(N)_{19}$-SL
3' $(N')_{19}$
5' $(N)_{19}$-C3Pi-C3Pi
3' $(N')_{19}$-SL
5' $(N)_{19}$-C3Pi-C3Pi
3' PiC3-$(N')_{19}$-SL
5' $(N)_{19}$-dTdT
3' PiC3-$(N')_{19}$-SL
5' $(N)_{19}$-dTdT
3' dTdT-$(N')_{19}$-SL
5' $(N)_{19}$-C3Pi-C3Pi
3' dTdT-$(N')_{19}$-SL
5' $(N)_{19}$-dTdT-SL
3' PiC3-$(N')_{19}$-SL
5' $(N)_{19}$-C3Pi-C3Pi
3' SL-$(N')_{19}$-z"
5' $(N)_{19}$-C3Pi-C3Pi
3' HOC3-$(N')_{19}$-SL wherein each N and N' is independently an unmodified ribonucleotide, a modified ribonucleotide or is an unconventional moiety;

wherein each N is linked to the adjacent N by a covalent bond;

wherein each N' is linked to the adjacent N' by a covalent bond;

wherein SL is a sphingolipid-polyalkylamine conjugate covalently attached at a 5' terminus or 3' terminus of the antisense strand or of the sense strand;

wherein C3OH, C3Pi and the like refer to C3 non-nucleotide moieties covalently attached at the 3' termini of a strand;

wherein dTdT refers to a thymidine dinucleotide;

wherein z" is a capping moiety covalently attached to the 5' terminus of the sense strand.

For all of the structures above, in some embodiments the oligonucleotide sequence of (N)x is fully complementary to the oligonucleotide sequence of (N')y. In other embodiments the antisense and sense strands are substantially complementary. In certain embodiments (N)x is fully complementary to a mammalian mRNA. In other embodiments (N)x is substantially complementary to a mammalian mRNA.

Further provided is a pharmaceutical composition comprising a sphingolipid-polyalkylamine compound disclosed herein, in an amount effective to inhibit mammalian or non-mammalian gene expression, and a pharmaceutically acceptable carrier, and use thereof for treatment of any one of the diseases and disorders disclosed herein. In some embodiments the mammalian gene is a human gene. In some embodiments the non-mammalian gene is involved in a mammalian disease, preferably human disease.

Further provided are methods for treating or preventing the incidence or severity of cancer disclosed herein or for reducing the risk or severity of the cancer disclosed herein in a subject in need thereof, wherein the cancer and/or a symptom or risk associated therewith is associated with expression of a mammalian gene or non-mammalian gene the method comprising administering to a subject in need thereof a therapeutically effective amount of a sphingolipid-polyalkylamine oligonucleotide compound disclosed herein. In a preferred embodiment the subject is a human subject. Provided herein are double-stranded nucleic acid molecules for therapy.

Further provided are sphingolipid-polyalkylamine compounds as disclosed herein for use in treating or preventing the incidence or severity of cancer or for reducing the risk or severity of the cancer, wherein the cancer and/or a symptom or risk associated therewith is associated with expression of a mammalian gene or non-mammalian gene.

Further provided is the use of the sphingolipid-polyalkylamine compounds as disclosed herein for the manufacture of a medicament for treating or preventing the incidence or severity of cancer or for reducing the risk or severity of the cancer, wherein the cancer and/or a symptom or risk associated therewith is associated with expression of a mammalian gene or non-mammalian gene.

siRNA Synthesis

Using public and proprietary algorithms the sense and antisense sequences of potential double-stranded RNA molecules are generated.

The oligonucleotides according to the above specifications are prepared essentially as described herein. The modified nucleic acid molecules are synthesized by any of the methods that are well known in the art for synthesis of ribonucleic (or deoxyribonucleic) oligonucleotides. Synthesis is commonly performed in a commercially available synthesizer (available, inter alia, from Applied Biosystems). Oligonucleotide synthesis is described for example in Beaucage and Iyer, Tetrahedron 1992; 48:2223-2311; Beaucage and Iyer, Tetrahedron 1993; 49: 6123-6194 and Caruthers, et. al., Methods Enzymol. 1987; 154: 287-313; the synthesis of thioates is, among others, described in Eckstein, Ann Rev. Biochem. 1985; 54: 367-402, the synthesis of RNA molecules is described in Sproat, in Humana Press 2005 edited by Herdewijn P.; Kap. 2: 17-31 and respective downstream processes are, among others, described in Pingoud et al., in IRL Press 1989 edited by Oliver R. W. A.; Kap. 7: 183-208.

Other synthetic procedures are known in the art, e.g. the procedures described in Usman et al., 1987, J. Am. Chem. Soc., 109, 7845; Scaringe et al., 1990, NAR., 18, 5433; Wincott et al., 1995, NAR. 23, 2677-2684; and Wincott et al., 1997, Methods Mol. Bio., 74, 59, may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

In some embodiments the oligonucleotides disclosed herein are synthesized separately and joined together post-synthetically, for example, by ligation (Moore et al., 1992, Science 256, 9923; Draper et al., International Patent Publication No. WO 93/23569; Shabarova et al., 1991, NAR 19, 4247; Bellon et al., 1997, Nucleosides & Nucleotides, 16, 951; Bellon et al., 1997, Bioconjugate Chem. 8, 204), or by hybridization following synthesis and/or de-protection.

Overlapping pairs of chemically synthesized fragments can be ligated using methods well known in the art (e.g., see U.S. Pat. No. 6,121,426). The strands are synthesized separately and are annealed to each other in the tube. The double-stranded siRNAs are separated from the single-stranded oligonucleotides that were not annealed (e.g. because of the excess of one of them) by HPLC. In relation to the sphingolipid-polyalkylamine compounds disclosed herein, two or more such sequences can be synthesized and linked together for use.

In one embodiment, provide are double-stranded nucleic acid (e.g. dsRNA, siRNA, siNA), which down-regulate the expression of mammalian or non-mammalian target genes. The double-stranded molecules comprise for example at least one pyrazolotriazine nucleotide analog on the sense strand and or the antisense strand. In some embodiments the sense strand comprises a nucleotide sequence derived from the target RNA sequence, and the antisense strand is complementary to the sense strand. In general, some deviation from the target mRNA sequence is tolerated without compromising the siRNA activity (see e.g. Czauderna et al., 2003, NAR 31(11), 2705-2716). A dsRNA of the invention inhibits gene expression on a post-transcriptional level with or without destroying the mRNA. Without being bound by theory, dsRNA may target the mRNA for specific cleavage and degradation and/or may inhibit translation from the targeted message.

In one aspect, provided are nucleic acid molecules (e.g., siNA molecules) in which a) the nucleic acid molecule includes a sense strand and an antisense strand; b) each strand of the molecule is independently 15 to 49 nucleotides in length; (c) a 15 to 49 nucleotide sequence of the antisense strand is complementary to a sequence of a target RNA; d) at least one sphingolipid-polyalkylamine conjugate is covalently attached at the 3' terminus of the sense strand, at the 3' terminus of the antisense strand or at the 5' terminus of the sense strand; and e) 15 to 49 nucleotide sequence of the sense strand is complementary to the a sequence of the antisense strand and includes a 15 to 49 nucleotide sequence of a target RNA.

In some embodiments the antisense strand and the antisense strand are the same length. In some embodiments the antisense strand and the sense strand are 18-25 or 18-23 or 18-21 or 19-21 or 19 nucleotides in length.

Coupling of Sphingolipid-Polyalkylamine Conjugate to a Nucleotide or Oligonucleotide A sphingolipid-polyalkylamine conjugate phosphoramidite may be coupled to the 5' terminus of a nucleotide in a synthesizer, for example, at the final step of synthesis. Alternatively, a sphingolipid-polyalkylamine compound may be coupled to a solid support followed by the addition of nucleotides to form a conjugate with a 2' or 3' linkage (sphingolipid-polyalkylamine covalently linked to the 2' or 3' position in the sugar of the terminal nucleotide of the oligonucleotide). Another possibility is to prepare the oligonucleotide and then, in a post synthesis step, to attach or couple the sphingolipid-polyalkylamine conjugate to a terminal nucleotide or internal nucleotide, after removal of a suitable protective group on the selected nucleotide, to form a linkage at a terminal site or at an internal site on the oligonucleotide. Preferably, the sphingolipid-polyalkylamine conjugate is attached to a terminal nucleotide, to form a conjugate with a linkage at a terminal site. For siRNA oligonucleotides, the sphingolipid-polyalkylamine conjugate may be attached to one terminus or both termini of the sense strand or to the 3' terminus of the antisense strand, either directly or via a linker A sphingolipid-polyalkylamine conjugate may be coupled to an oligonucleotide in a variety of ways. Possible linkages include amide, phosphate, thioether, amino and ether linkages. An amide linkage may be generated by reacting an activated carboxylic acid derivative of a sphingolipid-polyalkylamine with an amino linker attached to an oligonucleotide. Activation may be achieved in solution phase or on a solid support using methods known to those skilled in the art. Non-limiting examples include using dicyclohexylcarbodiimide (DCC) and N-hydroxysuccinimide (NHS), 1-ethyl-3-(3-dimethylaminopropyl)carbodiimide HCl (EDC), or activated esters of NHS, nitrophenyl, pentachlorophenyl, acid anhydride or sulfonyl chloride. In addition, for the solid support reaction, activation may be in the form of an acid chloride. A phosphate linkage results from the reaction of an activated phosphate derivative of a sphingolipid-polyalkylamine conjugate and the 5' hydroxyl group on an oligonucleotide. The activated phosphate may be, for example, a phosphoramidite, an H-phosphonate, a triester or a diester.

Pharmaceutical Compositions

While it is possible for the sphingolipid-polyalkylamine oligonucleotide molecules disclosed herein to be administered as the raw chemical, it is preferable to present them as a pharmaceutical composition. Accordingly, provided herein is a pharmaceutical composition comprising one or more of the sphingolipid-polyalkylamine oligonucleotide compounds disclosed herein; and a pharmaceutically acceptable carrier. In some embodiments the pharmaceutical composition comprises two or more sphingolipid-polyalkylamine oligonucleotide compounds disclosed herein.

Further provided are pharmaceutical compositions comprising at least one sphingolipid-polyalkylamine oligonucleotide compound, or salt of such compound, disclosed herein in an amount effective to inhibit a target gene expression; and a pharmaceutically acceptable carrier. The sphingolipid-polyalkylamine oligonucleotide compound may be processed intracellularly by endogenous cellular complexes (for example DICER) to produce one or more nucleic acid molecules disclosed herein.

Further provided are pharmaceutical compositions comprising a pharmaceutically acceptable carrier and one or more of the compounds disclosed herein in an amount effective to inhibit expression in a cell of a mammalian target gene.

In some embodiments, the sphingolipid-polyalkylamine oligonucleotide compounds, or salts of such compounds, disclosed herein are the main active component in a pharmaceutical composition. In other embodiments a sphingolipid-polyalkylamine oligonucleotide compound disclosed herein is one of the active components of a pharmaceutical composition containing two or more therapeutic agents, said pharmaceutical composition further being comprised of one or more dsRNA molecules which target one or more target genes or for example, a small molecule drug.

Further provided is a process of preparing a pharmaceutical composition, which comprises: providing one or more sphingolipid-polyalkylamine oligonucleotide compound disclosed herein; and admixing said compound with a pharmaceutically acceptable carrier.

In a preferred embodiment, a sphingolipid-polyalkylamine oligonucleotide compound disclosed herein used in the preparation of a pharmaceutical composition is admixed with a carrier in a pharmaceutically effective dose.

Also provided are kits, containers and formulations that include a sphingolipid-polyalkylamine oligonucleotide compound as provided herein for reducing expression of a target gene for administering or distributing the nucleic acid molecule to a patient. A kit may include at least one container and at least one label. Suitable containers include, for example, bottles, vials, syringes, and test tubes. The containers can be formed from a variety of materials such as glass, metal or plastic. In one embodiment, the container holds a sphingolipid-polyalkylamine oligonucleotide compounds as disclosed herein. Kits may further include associated indications and/or directions; reagents and other compositions or tools used for such purpose can also be included.

The container can alternatively hold a composition comprising an active agent (e.g. sphingolipid-spermine oligonucleotide compound) that is effective for treating, diagnosis, prognosing or prophylaxing a condition and can have a sterile access port (for example the container can be an intravenous solution bag or a vial having a stopper pierceable by a hypodermic injection needle). The active agent in the composition can be a sphingolipid-polyalkylamine compound as disclosed herein.

A kit may further include a second container that includes a pharmaceutically-acceptable buffer and may further include other materials desirable from a commercial and user standpoint, including other buffers, diluents, filters, stirrers, needles, syringes, and/or package inserts with indications and/or instructions for use.

The container holding the sphingolipid-polyalkylamine oligonucleotide compound may include a package that is labeled, and the label may bear a notice in the form prescribed by a governmental agency, for example the Food and Drug Administration, which notice is reflective of approval by the agency under Federal law, of the manufacture, use, or sale of the polynucleotide material therein for human administration.

Dosages

The useful dosage to be administered and the particular mode of administration of the sphingolipid-polyalkylamine oligonucleotide compound will vary depending upon such factors as the cell type, or for in vivo use, the age, weight and the particular subject and region or organ thereof to be treated, the particular nucleic acid and delivery method used, the therapeutic or diagnostic use contemplated, the indication and the form of the formulation, for example, naked, suspension, emulsion, micelle or liposome, as will be readily apparent to those skilled in the art. Typically, dosage is administered at lower levels and increased until the desired effect is achieved.

A "therapeutically effective dose" for purposes herein is determined by considerations as are known in the art. The dose must be effective to achieve improvement including but not limited to improved survival rate or more rapid recovery, or improvement or alleviation of elimination of symptoms and other indicators as are selected as appropriate measures by those skilled in the art. The dsRNA disclosed herein can be administered in a single dose or in multiple doses.

A suitable dosage unit of nucleic acid molecules may be in the range of 0.001 to 0.25 milligrams per kilogram body weight of the recipient per day, or in the range of 0.01 to 20 micrograms per kilogram body weight per day, or in the range of 0.01 to 10 micrograms per kilogram body weight per day, or in the range of 0.10 to 5 micrograms per kilogram body weight per day, or in the range of 0.1 to 2.5 micrograms per kilogram body weight per day.

Suitable amounts of nucleic acid molecules may be introduced and these amounts can be empirically determined using standard methods. Effective concentrations of individual nucleic acid molecule species in the environment of a cell may be about 1 femtomolar, about 50 femtomolar, 100 femtomolar, 1 picomolar, 1.5 picomolar, 2.5 picomolar, 5 picomolar, 10 picomolar, 25 picomolar, 50 picomolar, 100 picomolar, 500 picomolar, 1 nanomolar, 2.5 nanomolar, 5 nanomolar, 10 nanomolar, 25 nanomolar, 50 nanomolar, 100 nanomolar, 500 nanomolar, 1 micromolar, 2.5 micromolar, 5 micromolar, 10 micromolar, 100 micromolar or more.

An appropriate dosage for a mammal may be from 0.01 ug to 1 g per kg of body weight (e.g., 0.1 ug, 0.25 ug, 0.5 ug, 0.75 ug, 1 ug, 2.5 ug, 5 ug, 10 ug, 25 ug, 50 ug, 100 ug, 250 ug, 500 ug, 1 mg, 2.5 mg, 5 mg, 10 mg, 25 mg, 50 mg, 100 mg, 250 mg, or 500 mg per kg).

Dosage levels of the order of from about 0.1 mg to about 140 mg per kilogram of body weight per day are useful in the treatment of the above-indicated conditions (about 0.5 mg to about 7 g per subject per day). The amount of active ingredient that can be combined with the carrier materials to produce a single dosage form varies depending upon the host treated and the particular mode of administration. Dosage unit forms generally contain between from about 0.1 mg to about 500 mg of an active ingredient.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

Pharmaceutical compositions that include the compounds disclosed herein may be administered once daily, qid, tid, bid, QD, or at any interval and for any duration that is medically appropriate. However, the therapeutic agent may also be dosed in dosage units containing two, three, four, five, six or more sub-doses administered at appropriate intervals throughout the day. In that case, the nucleic acid molecules contained in each sub-dose may be correspondingly smaller in order to achieve the total daily dosage unit. The dosage unit can also be compounded for a single dose over several days, e.g., using a conventional sustained release formulation which provides sustained and consistent release of the dsRNA over a several day period. Sustained release formulations are well known in the art. The dosage unit may contain a corresponding multiple of the daily dose. The composition can be compounded in such a way that the sum of the multiple units of nucleic acids together contains a sufficient dose.

Delivery

The sphingolipid-polyalkylamine-oligonucleotide compounds disclosed herein are administered as the compound per se (i.e. as naked siRNA) or as pharmaceutically acceptable salt and are administered alone or as an active ingredient in combination with one or more pharmaceutically acceptable carrier, solvent, diluent, excipient, adjuvant and vehicle. In some embodiments, the sphingolipid-polyalkylamine oligonucleotide compounds are delivered to the target tissue by direct application of the naked molecules prepared with a carrier or a diluent such as PBS or other physiological solutions.

The term "naked siRNA" refers to siRNA molecules that are free from any delivery vehicle that acts to assist, promote or facilitate entry into the cell, including viral sequences, viral particles, liposome formulations, lipofectin or precipitating agents and the like. For example, siRNA in PBS is "naked siRNA".

Pharmaceutically acceptable carriers, solvents, diluents, excipients, adjuvants and vehicles as well as implant carriers generally refer to inert, non-toxic solid or liquid fillers, diluents or encapsulating material not reacting with the sphingolipid-polyalkylamine-oligonucleotide compounds disclosed herein.

Additionally, the compositions may include an artificial oxygen carrier, such as perfluorocarbons (PFCs) e.g. perfluorooctyl bromide (perflubron).

Additional formulations for improved delivery of the compounds disclosed herein can include non-formulated compounds and compounds bound to targeting antibodies (Song et al., Nat Biotechnol. 2005. 23(6):709-17) or aptamers.

The naked compounds or the pharmaceutical compositions comprising the compounds disclosed herein are administered and dosed in accordance with good medical practice, taking into account the clinical condition of the individual patient, the disease to be treated, the site and method of administration, scheduling of administration, patient age, sex, body weight and other factors known to medical practitioners.

The sphingolipid-polyalkylamine oligonucleotide compounds are preferably administered orally, subcutaneously or parenterally including intravenous, and intraperitoneally, as well as infusion techniques. Implants of the compounds are also useful.

Liquid forms are prepared for invasive administration, e.g. injection. The liquid compositions include aqueous solutions, with and without organic co-solvents, aqueous or oil suspensions, emulsions with edible oils, as well as similar pharmaceutical vehicles. In a particular embodiment, the administration comprises intravenous administration.

Methods of Treatment

In one aspect provided herein is a method of treating a subject suffering from cancer comprising administering to the subject a therapeutically effective amount of a sphingolipid-polyalkylamine-oligonucleotide compound disclosed herein. In preferred embodiments the subject being treated is a warm-blooded animal and, in particular, mammal including human.

In a further aspect, provided herein is a sphingolipid-polyalkylamine-oligonucleotide compound as disclosed herein for use in treating a subject suffering from cancer.

In an additional aspect, provided herein is the use of a sphingolipid-polyalkylamine-oligonucleotide compound as disclosed herein for the manufacture of a medicament for treating cancer.

"Treating a subject" refers to administering to the subject a therapeutic substance (i.e. sphingolipid polyalkylamine oligonucleotide) effective to ameliorate symptoms associated with cancer, to lessen the severity or cure cancer, to slow down the progression of cancer, to cancer from occurring or to postpone the onset of cancer. "Treatment" refers to both therapeutic treatment and prophylactic or preventative measures, wherein the object is to prevent cancer, to delay the onset of cancer or reduce the symptoms of cancer. Those in need of treatment of cancer include those already having cancer, those prone to having cancer, and those in which cancer is to be prevented. The compounds disclosed herein are administered before, during or subsequent to the onset of cancer.

A "therapeutically effective dose" refers to an amount of a pharmaceutical compound or composition which is effective to achieve an improvement in a subject or his physiological systems including, but not limited to, improved survival rate, more rapid recovery, improvement or elimination of symptoms, delayed onset of a disorder, slower progress of disease and other indicators as are selected as appropriate determining measures by those skilled in the art.

Provided herein are compounds, compositions and methods useful in the treatment of cancer. The terms "cancer" and "cancerous" refer to or describe the physiological condition in mammals that is typically characterized by unregulated cell growth and includes benign and malignant growths. Examples of cancer include but are not limited to, carcinoma, lymphoma, blastoma, sarcoma, and leukemia or lymphoid malignancies. Other examples of such cancers include kidney or renal cancer, breast cancer, colon cancer, rectal cancer, colorectal cancer, lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, liver cancer, bladder cancer, cancer of the peritoneum, hepatocellular cancer, gastric or stomach cancer including gastrointestinal cancer, gastrointestinal stromal tumors (GIST), pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma and acute hematologic malignancies, endometrial or uterine carcinoma, endometriosis, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, leiomyosarcomas, urinary tract carcinomas, thyroid carcinomas, Wilm's tumor, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. "Tumor", as used herein, refers to all neoplastic cell growth and proliferation, whether malignant or benign, and all pre-cancerous and cancerous cells and tissues.

Additionally, provided is a method of down-regulating the expression of a target gene by at least 20%, 30%, 40% or 50% as compared to a control comprising contacting target mRNA with one or more of the sphingolipid-polyalkylamine oligonucleotide compounds disclosed herein.

Additionally, provided are sphingolipid-polyalkylamine oligonucleotide compounds disclosed herein for use in down-regulating the expression of a target gene by at least 20%, 30%, 40% or 50% as compared to a control, wherein the molecules are to be contacted with target mRNA.

Additionally, provided are the use of sphingolipid-polyalkylamine oligonucleotide compounds disclosed herein for the manufacture of a medicament for down-regulating the expression of a target gene by at least 20%, 30%, 40% or 50% as compared to a control, wherein the molecules are to be contacted with target mRNA.

In various embodiments the sphingolipid-polyalkylamine oligonucleotide compounds down-regulates target gene whereby the down-regulation is selected from the group comprising down-regulation of gene function, down-regulation of polypeptide and down-regulation of mRNA expression.

Provide herein is a method of inhibiting the expression of a target gene by at least 20%, 30%, or 40%, preferably by 50%, 60% or 70%, more preferably by 75%, 80% or 90% as compared to a control comprising contacting an mRNA transcript of the target gene with one or more of the sphingolipid-polyalkylamine oligonucleotide compounds disclosed herein.

Further provided herein are the sphingolipid-polyalkylamine oligonucleotide molecules disclosed herein for use in inhibiting the expression of a target gene by at least 20%, 30%, or 40%, preferably by 50%, 60% or 70%, more preferably by 75%, 80% or 90% as compared to a control, wherein the sphingolipid-polyalkylamine oligonucleotide compounds are to be contacted with an target RNA.

Further provided herein is the use of the sphingolipid-polyalkylamine oligonucleotide compounds disclosed herein in the manufacture of a medicament for inhibiting the expression of a target gene by at least 20%, 30%, or 40%, preferably by 50%, 60% or 70%, more preferably by 75%, 80% or 90% as compared to a control, wherein the compounds are to be contacted with target RNA.

In one embodiment the sphingolipid-polyalkylamine oligonucleotide compounds disclosed herein inhibit the target gene polypeptide, whereby the inhibition is selected from the group comprising inhibition of function (which is examined by, for example, an enzymatic assay or a binding assay with a known interactor of the native gene/polypeptide, inter alia), inhibition of target protein (which is examined by, for example, Western blotting, ELISA or immuno-precipitation, inter alia) and inhibition of target mRNA expression (which is examined by, for example, Northern blotting, quantitative RT-PCR, in-situ hybridization or microarray hybridization, inter alia).

In additional embodiments provided is a method of treating a subject suffering from or susceptible to cancer accompanied by an elevated level of a mammalian or non-mammalian target gene, the method comprising administering to the subject a sphingolipid-polyalkylamine oligonucleotide compound disclosed herein in a therapeutically effective dose thereby treating the subject.

In additional embodiments provided is a sphingolipid-polyalkylamine oligonucleotide compound disclosed herein for use in treating a subject suffering from or susceptible to cancer accompanied by an elevated level of a mammalian or non-mammalian target gene.

In additional embodiments provided is the use of a sphingolipid-polyalkylamine oligonucleotide compound disclosed herein in the manufacture of a medicament for treating a subject suffering from or susceptible to cancer accompanied by an elevated level of a mammalian or non-mammalian target gene.

Without limitation a mammalian target gene associated with cancer is PLK, RAC1 or K-RAS. One with skill in the art will be able to identify relevant cancer target genes and generate an active antisense or dsRNA molecule to target the gene or gene transcription product. Other examples include antagomirs (antimirs) for ongogenic genes.

In additional embodiments provided is a method of treating a subject suffering from or susceptible to cancer accompanied by reduced function of a mammalian or non-mammalian target gene, the method comprising administering to the subject a sphingolipid-polyalkylamine oligonucleotide compound disclosed herein in a therapeutically effective dose thereby treating the subject.

In additional embodiments provided is a sphingolipid-polyalkylamine oligonucleotide compound disclosed herein for use in treating a subject suffering from or susceptible to cancer accompanied by reduced function of a mammalian or non-mammalian target gene.

In additional embodiments provided is the use of a sphingolipid-polyalkylamine oligonucleotide compound disclosed herein in the manufacture of a medicament for treating a subject suffering from or susceptible to cancer accompanied by reduced function of a mammalian or non-mammalian target gene.

For example, sphingolipid-polyalkylamine oligonucleotide compound which up-regulates expression of p53 in a p53 negative tumor would be desired. Other examples include tumor suppressors that are not mutated/deleted but just down-regulated; MHC I that is frequently selected against in cancer progression to avoid immune attack on cancer cells and miRNA mimetics for tumor suppressor miRNA. RNA aptamers are useful in therapy and are easily linked to the sphingolipid-polyalkylamine conjugate. Non-limiting examples of RNA aptamers are disclosed in for example, Zhou, et al., (2012), Frontiers in Genetics 3, article 234.

Combination Therapy

The methods of treating the diseases disclosed herein include administering a sphingolipid-polyalkylamine oligonucleotide compound disclosed herein in conjunction or in combination with an additional inhibitor, a substance which improves the pharmacological properties of the sphingolipid-polyalkylamine oligonucleotide compound, or an additional compound known to be effective in the treatment of a subject suffering from or susceptible to any of the hereinabove mentioned diseases and disorders. In some embodiments the sphingolipid-polyalkylamine oligonucleotide compound is administered together with chemotherapy or radiation therapy. In some embodiments, the sphingolipid-polyalkylamine oligonucleotide compounds are preferably administered systemically, for example intravenous administration.

In another embodiment, provided are pharmaceutical compositions comprising a combination of sphingolipid-polyalkylamine oligonucleotide compound disclosed herein together with at least one additional therapeutically active agent or therapy. By "in conjunction with" or "in combination with" is meant prior to, simultaneously or subsequent to. Accordingly, the individual components of such a combination are administered either sequentially or simultaneously from the same or separate pharmaceutical formulations.

Accordingly, in another embodiment, an additional pharmaceutically effective compound is administered in conjunction with the pharmaceutical composition disclosed herein. In addition, the sphingolipid-polyalkylamine oligonucleotide compounds disclosed herein are used in the preparation of a medicament for use as adjunctive therapy with a second therapeutically active compound to treat such conditions. Appropriate doses of known second therapeutic agents for use in combination with a chemically modified nucleic acid molecule disclosed herein are readily appreciated by those skilled in the art.

In some embodiments the combinations referred to above are presented for use in the form of a single pharmaceutical formulation.

By "in conjunction with" is meant that the additional pharmaceutically effective compound is administered prior to, at the same time as, or subsequent to administration of the compounds or the pharmaceutical compositions disclosed herein. The individual components of such a combination referred to above, therefore, can be administered either sequentially or simultaneously from the same or separate pharmaceutical formulations. As is the case for the sphingolipid-polyalkylamine oligonucleotide compounds, a second therapeutic agent can be administered by any suitable route, for example, by oral, buccal, inhalation, sublingual, rectal, vaginal, transurethral, topical (dermal, nasal etc) percutaneous (i.e., transdermal), or parenteral (including intravenous, intramuscular, subcutaneous, and intracoronary) administration.

In some embodiments, a sphingolipid-polyalkylamine oligonucleotide compound disclosed herein and a second therapeutic agent (e.g. dsRNA or chemotherapy) are administered by the same route, either provided in a single composition as two or more different pharmaceutical compositions. However, in other embodiments, a different route of administration for the sphingolipid-polyalkylamine oligonucleotide compound disclosed herein and the second therapeutic agent is either possible or preferred. Persons skilled in the art are aware of the best modes of administration for each therapeutic agent, either alone or in combination.

In various embodiments, the sphingolipid-polyalkylamine oligonucleotide compounds disclosed herein are the main active component in a pharmaceutical composition.

The treatment regimen according to the invention is carried out, in terms of administration mode, timing of the administration, and dosage, so that the functional recovery of the patient from the adverse consequences of the conditions disclosed herein is improved or so as to postpone the onset of a disorder. The amount of active ingredient that can be combined with a carrier to produce a single dosage form varies depending upon the host treated and the particular mode of administration. Dosage unit forms generally contain between from about 0.1 mg to about 500 mg of an active ingredient The invention has been described in an illustrative manner, and it is to be understood that the terminology used is intended to be in the nature of words of description rather than of limitation.

Modifications and variations of the present invention are possible in light of the above teachings. It is, therefore, to be understood that within the scope of the appended claims, the invention can be practiced otherwise than as specifically described.

The present invention is illustrated in detail below with reference to examples, but is not to be construed as being limited thereto.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook et al., *Molecular cloning: A laboratory manual*, Cold Springs Harbor Laboratory, New-York (1989, 1992), and in Ausubel et al., *Current Protocols in Molecular Biology*, John Wiley and Sons, Baltimore, Md. (1988), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in PCR Protocols: A Guide To Methods And Applications, Academic Press, San Diego, Calif. (1990). In situ (In cell) PCR in combination with Flow Cytometry is useful for detection of cells containing specific DNA and mRNA sequences (Testoni et al., Blood 1996, 87:3822.) Methods of performing RT-PCR are also well known in the art.

Example 1

Selection and Generation of Sense Strand and Antisense Strand Sequences for dsRNAs Using proprietary algorithms and the known sequence of a target gene, 18 and 19-mer sequences for potential dsNAs are generated. The antisense strand sequences generated using this method are fully or substantially complementary to a section of target mRNA sequence. In some embodiments the antisense sequence is fully complementary to a section of the corresponding mRNA sequence. In general, the double-stranded nucleic acid molecules having specific sequences that are selected for in vitro testing are specific for human and a second species such as rat, mouse non-human primate or rabbit genes.

The exemplary compounds target Rac1 (*Homo sapiens* ras-related C3 botulinum toxin substrate 1 (rho family, small GTP binding protein Rac1) (RAC1), transcript variant Rac1, mRNA) gi|156071503|ref|NM_006908.4 (SEQ ID NO:1); PLK1 (*Homo sapiens* polo-like kinase 1) gi|34147632|ref|NM_005030.3 (SEQ ID NO:2) and KRAS (*Homo sapiens*

Kirsten rat sarcoma viral oncogene homolog (KRAS), transcript variant a, mRNA) gi|575403058|ref|NM_033360.3 (SEQ ID NO:3) and (*Homo sapiens* Kirsten rat sarcoma viral oncogene homolog (KRAS), transcript variant b, mRNA) gi|575403057|ref|NM_004985.4 (SEQ ID NO:4).

Polynucleotide sequences of target RNA sequences of mammalian and non-mammalian target genes are available, for example, on the NCBI web site [http://www.ncbi.nlm.nih.gov/].

Synthesis of Chemically Modified Oligonucleotides

The sense strand and antisense strand were chemically synthesized and chemically modified nucleotide monomers were incorporated into the strands. The chemical modifications utilized herein were as follows:

```
Rac1_28:
SENSE STRAND
                                              (SEQ ID NO: 5)
(5' > 3')  CGUGCAAAGUGGUAUCCUG
and ANTISENSE STRAND
                                              (SEQ ID NO: 6)
(5' > 3')  CAGGAUACCACUUUGCACG Plk1_28
SENSE STRAND
                                              (SEQ ID NO: 7)
(5' > 3')  AGAAGAUGCUUCAGACAGU
and ANTISENSE STRAND
                                              (SEQ ID NO: 8)
(5' > 3')  ACUGUCUGAAGCAUCUUCU Kras
SENSE STRAND
                                              (SEQ ID NO: 9)
(5' > 3')  GUAAGGCAGACCCAGUAUA ANTISENSE STRAND
                                              (SEQ ID NO: 10)
(5' > 3')  UAUACUGGGUCUGCCUUAC
```

Table 1 provides a description of exemplary siRNA compounds synthesized.

TABLE 1

| Exemplary siRNA strands synthesized and compounds targeting RAC1 (siRAC1): | | |
|---|---|---|
| Compound name | Sense strand (5' > 3') | Antisense strand (5' > 3') |
| RAC1_28_S2045 | zSLSp;mC;rG;mU;rG;mC; Ar;rA;rA;rG;mU;rG;rG;mU; rA;rU;mC;rC;mU;rA | mU;rA;rG;rG;rA;mU;rA;rC;mC; rA;mC;rU;mU;rU;mG;rC;mA;rC; mG |
| RAC1_28_S2081 | zSLSpdp;mC;rG;mU;rG;mC; rA;rA;rA;rG;mU;rG;rG;mU; rA;rU;mC;rC;mU;rA | mU;rA;rG;rG;rA;mU;rA;rC;mC; rA;mC;rU;mU;rU;mG;rC;mA;rC; mG |
| RAC1_28_S2281 | zSLSp;mC;rG;mU;rG;mC;rA; rA;rA;rG;mU;rG;rG;mU;rA; rU;mC;rC;mU;rA | mU;rA;rG;rG;rA;mU;rA;rC;mC; rA;mC;rU;mU;rU;mG;rC;mA;rC; mG;zcy3$ |
| RAC1_28_S2139 | zSLSpdp;mC;rG;mU;rG;mC; rA;rA;rA;rG;mU;rG;rG;mU; rA;rU;mC;rC;mU;rA | rAps;rA;rG;rG;rA;2fU;rA;2fC; 2fC;2fA;2fC;2fU;2fU;2fU;rG; 2fC;rA;2fC;rGps;zdTps;zdT$ |
| RAC1_28_S1908 (control) | mC;rG;mU;rG;mC;rA;rA;rA; rG;mU;rG;rG;mU;rA;rU;mC; rC;mU;rA | mU;rA;rG;rG;rA;mU;rA;rC;mC; rA;mC;rU;mU;rU;mG;rC;mA;rC; mG |
| RAC1_28_S2132 (control) | mC;rG;mU;rG;mC;rA;rA;rA; rG;mU;rG;rG;mU;rA;rU;mC; rC;mU;rA | mU;rA;rG;rG;rA;mU;rA;rC;mC; rA;mC;rU;mU;rU;mG;rC;mA;rC; mG;zcy3$ |
| KRAS_2_S2309 | zSLSp;rG;mU;rA;rA;rG;rG; mC;rA;rG;rA;rC;rC;mC;rA; rG;mU;rA;mU;rA | mU;rA;mU;rA;rC;mU;rG;rG;rG; rU;rC;rU;rG;rC;mC;rU;mU;rA; mC |
| KRAS_2_S2087 (control) | rG;mU;rA;rA;rG;rG;mC;rA; rG;rA;rC;rC;mC;rA;rG;mU; rA;mU;rA | mU;rA;mU;rA;rC;mU;rG;rG;rG; rU;rC;rU;rG;rC;mC;rU;mU;rA; mC |
| PLK1_28_S2272 | zSLSp;rA;rG;rA;rA;rG;rA; mU;rG;rC;rU;rU;mC;rA;rG; rA;mC;rA;rG;rU | rA;rC;mU;rG;rU;rC;mU;rG;rA; rA;rG;rC;rA;rU;mC;rU;mU;rC; mU |

TABLE 1-continued

Exemplary siRNA strands synthesized and compounds targeting RAC1 (siRAC1):

| Compound name | Sense strand (5' > 3') | Antisense strand (5' > 3') |
| --- | --- | --- |
| PLK1_28_S2054 (control) | zc6Np;rA;rG;rA;rA;rG;rA; mU;rG;rC;rU;rU;mC;rA;rG; rA;mC;rA;rG;rU | rA;rC;mU;rG;rU;rC;mU;rG;rA; rA;rG;rC;rA;rU;mC;rU;mU;rC; mU |

TABLE 2

| Legend for compound tables | |
| --- | --- |
| Modification Code | Modification Description |
| $ | No 3' Phosphate |
| m | 2'-O-methyl ribo-nucleotide-3'-phosphate |
| rN2p | ribo-nucleotide-2'-phosphate |
| nc | Nicked |
| zdT | Deoxy-Thymidine-3'-Phosphate |
| zidT | Inverted-Deoxy-Thymidine-5'-Phosphate |
| d | deoxyribose-5'-phosphate |
| zdT; zdT | dTdT overhang at 3' terminus |
| zidB | Inverted abasic deoxyribose-5'-phosphate; At 5' = 5'-5' idAb; At 3' = 3'-3' idAb |
| zc6Np | Amino-C6-Phosphate |
| 5'p | 5'-regular Phosphate |
| dB | abasic deoxyribose-3'-phosphate (Tetrahydrofuran) |
| m5r | 5-Methyl-ribonucleotide (cytidine/uridine) |
| zrA; zrG | rArG |
| zirB | Inverted abasic ribose-5'-phosphate |
| zrB; zrB | abasic ribose-3'-phosphate x2 |
| zirB; zirB | Inverted abasic ribose-5'-phosphate x2 |
| zdB; zdB | abasic deoxyribose-3'-phosphate x2 |
| zc3p; zc3p | 1,3-Propanediol-Pi x2 = (CH2)3-Pi x2 |
| zc3p; zrG | (CH2)3-Pi_rG |
| zc3p; zrB | (CH2)3-Pi; ribo-Abasic-3'-Pi |
| zc3p | (CH2)3-Pi = 3-Hydroxypropane-1-phosphate |
| z(c12Np)2-SD | (C12-Amino-Pi)2- Symmetrical Doubler |
| z(c12p)2-SD | (C12-Pi)2-Symmetrical Doubler |
| d | deoxyUridine |
| rNps | Phosphorothioated RNA base (rNps = rN*) |
| zc3p; zc3p; zc3p | (CH2)3-Pi x3; = 3-Hydroxypropane-1-phosphate; |
| zc3p; zc3ps | (CH2)3-pi_1,3-Propanediol-Phosphorotioate |
| idB | Inverted abasic deoxyribose-5'-phosphate |
| s | 5' phosphorothioate = non-cleavable Pi |
| ptd | Pyrazolo-triazine Deoxy, C-C nucleoside |
| zc12Np | Amino-C12-Phosphate |
| z(CH2CH2O)3p; z(CH2CH2O)3p | (CH2CH2O)3-pi_(CH2CH2O)3-pi |
| zTHNBc6p;zc6p | Tetrahydronaphtalene-butyric-C6 phosphate_(CH2)6-pi |
| zTHNBc6p;z(CH2CH2O)3p | Tetrahydronaphtalene-butyric-C6-phosphate_(CH2CH2O)3- |
| zTHNBc6p | Tetrahydronaphtalene-butyric-C6 phosphate |
| zSLSp; zThiC6SSp | Sphingolipid-Spermine-pi_Thiol Modifier-C6-S-S-phosphate |
| zSLSpd; zThiC6SSp | Sphingolipid-Spermidine-pi_Thiol Modifier-C6-S-S- |
| zSLSpdp | Sphingolipid-Spermidine-phosphate |
| zThiC6SSp | Thiol Modifier-C6-S-S-phosphate |
| zc6Np; zThiC6SSp | NH2-C6-pi_Thiol Modifier-C6-S-S-phosphate |
| ztnaA | TNA adenosine |
| ztnaC | TNA cytidine |
| dtna | D-Threose Nucleic Acid |
| mNps | Phosphorothioated-2'OMe RNA base (mNps = mN*) |
| 2f | 2'-deoxy-2'-fluoro nucleoside |
| zdTps; zdT | Thymidine-Phosphorothioate; Thymidine_overhang at 3'end |
| zThiC6SSp; zVEp | Thiol Modifier-C6-S-S_Vitamin E-pi |
| zPGA; zc6Np | PGA_NH2-C6-pi |
| ptr | Pyrazolo-triazine Ribo, C-C nucleoside |
| zPGA;;c6Np;zThiC6SSp | PGA_NH2-C6-pi_Thiol Modifier-C6-S-S-phosphate |
| rN2ps | Ribo-nucleotide-2'-phosphorotioate; Phosphorothioated 2'-5'- |
| zc3ps; zc3p | 1,3-Propanediol-Phosphorotioate_(CH2)3 |
| zc3ps | 1,3-Propanediol-Phosphorotioate |
| zSD | Symmetrical Doubler |
| z(VEp)2-SD | (Vitamin E-Pi)2-Symmetrical Doubler |
| zptrA | rA-Pyrazolo-triazine |

TABLE 2-continued

Legend for compound tables

| Modification Code | Modification Description |
|---|---|
| zptrA; zptrA | rA-Pyrazolo-triazine x2 |
| zc3ps; zc3ps | 1,3-Propanediol-Phosphorotioate x2 |
| zptdA | dA-Pyrazolo-triazine |
| zptdA; zptdA | dA-Pyrazolo-triazine x2 |

RAC1_28_S2045:

sense strand (SEQ ID NO:3) with 2'-O-methyl sugar modified ribonucleotides present in position (5'>3') 1, 3, 5, 10, 13, 16 and 18, a sphingolipid-spermine moiety conjugate to the 5' terminus, and a 3' phosphate.

antisense strand (SEQ ID NO:4) with 2'-O-methyl sugar modified ribonucleotides present in position (5'>3') 1, 6, 9, 11, 13, 15, 17 and 19, and a 3' phosphate.

RAC1_28_S2081:

sense strand (SEQ ID NO:3) with 2'-O-methyl sugar modified ribonucleotides present in position (5'>3') 1, 3, 5, 10, 13, 16 and 18, a sphingolipid-spermidine moiety conjugated to the 5' terminus, and a 3' phosphate.

antisense strand (SEQ ID NO:4) with 2'-O-methyl sugar modified ribonucleotides present in position (5'>3') 1, 6, 9, 11, 13, 15, 17 and 19, and a 3' phosphate.

RAC1_28_S2281:

sense strand (SEQ ID NO:3) with 2'-O-methyl sugar modified ribonucleotides present in position (5'>3') 1, 3, 5, 10, 13, 16 and 18, a sphingolipid-spermidine moiety conjugated to the 5' terminus, and a 3' phosphate.

antisense strand (SEQ ID NO:4) with 2'-O-methyl sugar modified ribonucleotides present in position (5'>3') 1, 6, 9, 11, 13, 15, 17 and 19, and a 3' CY3 moiety.

RAC1_28_S2139 sense strand (SEQ ID NO:3) with 2'-O-methyl sugar modified ribonucleotides present in position (5'>3') 1, 3, 5, 10, 13, 16 and 18, a sphingolipid-spermidine moiety conjugated to the 5' terminus, and a 3' phosphate.

antisense strand (SEQ ID NO:4) with 2'-deoxy-fluro sugar modified ribonucleotides present in position (5'>3') 6, 8, 9, 10, 11, 12, 13, 14, 16 and 18, a dTdt overhang covalently attached to the 3' terminus and phosphorothioate linkages between nucleotides 1-2, the 3' terminal nucleotide and the dT and between dT-dT.

RAC1_28_S1908 (Unconjugated Control):

CGUGCAAAGUGGUAUCCUG sense strand (SEQ ID NO:3) with 2'-O-methyl sugar modified ribonucleotides present in position (5'>3') 1, 3, 5, 10, 13, 16 and 18, and a 3' phosphate.

CAGGAUACCACUUUGCACG antisense strand (SEQ ID NO:4) with 2'-O-methyl sugar modified ribonucleotides present in position (5'>3') 1, 6, 9, 11, 13, 15, 17 and 19, and a 3' phosphate.

RAC1_28_S2132 (Unconjugated Control):

CGUGCAAAGUGGUAUCCUG sense strand (SEQ ID NO:3) with 2'-O-methyl sugar modified ribonucleotides present in position (5'>3') 1, 3, 5, 10, 13, 16 and 18, and a 3' phosphate.

CAGGAUACCACUUUGCACG antisense strand (SEQ ID NO:4) with 2'-O-methyl sugar modified ribonucleotides present in position (5'>3') 1, 6, 9, 11, 13, 15, 17 and 19, and a 3' CY3 moiety.

KRAS_2_S2309:

sense strand (SEQ ID NO:7) with 2'-O-methyl sugar modified ribonucleotides present in position (5'>3') 2, 7, 13, 16 and 18 a sphingolipid-spermine moiety conjugated to the 5' terminus, and a 3' phosphate.

antisense strand (SEQ ID NO:8) with 2'-O-methyl sugar modified ribonucleotides present in position (5'>3')1, 3, 6, 15, 17 and 19, and a 3' phosphate.

KRAS_2_S2087 (Unconjugated Control):

sense strand (SEQ ID NO:7) with 2'-O-methyl sugar modified ribonucleotides present in position (5'>3') 2, 7, 13, 16 and 18 and a 3' phosphate.

antisense strand (SEQ ID NO:8) with 2'-O-methyl sugar modified ribonucleotides present in position (5'>3')1, 3, 6, 15, 17 and 19, and a 3' phosphate.

PLK1_28_S2272:

sense strand (SEQ ID NO:5) with 2'-O-methyl sugar modified ribonucleotides present in position (5'>3') 7, 12 and 16, a sphingolipid-spermine moiety conjugated to the 5' terminus, and a 3' phosphate.

antisense strand (SEQ ID NO:6) with 2'-O-methyl sugar modified ribonucleotides present in position (5'>3') 3, 7, 15, 17 and 19, and a 3' phosphate.

PLK1_28_S2054 (Unconjugated Control):

sense strand (SEQ ID NO:5) with 2'-O-methyl sugar modified ribonucleotides present in position (5'>3') 7, 12 and 16, a 5' C6 amino cap and a 3' phosphate.

antisense strand (SEQ ID NO:6) with 2'-O-methyl sugar modified ribonucleotides present in position (5'>3') 3, 7, 15, 17 and 19, and a 3' phosphate.

Example 2

Synthesis of Sphingolipid-Spermine/Spermidine Phosphoramidite

FIG. 1 shows the scheme used for synthesizing a sphingosine-spermine/spermidine-phosphoramidite. Abbreviations: TFA: trifluoroacetate group; TBDMS:t-butyldimethylsilyl group; CC-column chromatography; MeOH-methanol; THF-tetrahydrofuran; DSC—Di(succinimido) carbonate; DMAP—4-Dimethylaminopyridine; DCM-4-(dicyanomethylene)-2-methyl-6-(p-dimethylaminostyryl)-4H-pyran; TBAF-Tetra-n-butylammonium fluoride.

Details of the synthesis steps are provided hereinbelow:

Compound 2

To a solution of D-erythro-sphingosine (1 g of compound 1) in MeOH (16 mL) ethyltrifluoroacetate (0.6 mL) and triethylamine (0.93 mL) are added. The mixture is stirred for 16 h, then solvent is evaporated to dryness under reduce pressure to yield crude compound 2. Crude product is purified by CC (silica, DCM/MeOH as eluent).

Compound 3

Compound 2 (1 g) is dissolved in THF (300 mL), followed by DSC (0.6 g) and DMAP (0.17 g) are added. The mixture is stirred for 6 h, and the solvent is evaporated to dryness. Crude product is purified by CC (silica, DCM/MeOH as eluent) to obtain compound 3.

Compound 4

Compound 9 (0.33 g) is dissolved in pyridine, then DMAP (17 mg) and compound 3 (600 mg) are added. The mixture is stirred for 16 h, after which the solvent is evaporated to dryness. Crude product is purified by CC (silica, Hexane/EtOAc as eluent) to obtain compound 4.

Compound 5

Compound 4 (840 g) is dissolved in DCM (300 mL), then DSC (0.5 g) and DMAP (0.14 g) are added. The mixture is stirred for 1 h, then Spermine/Spermidine (0.25 g) is added and reaction is stirred for 16 h. Crude product is purified by CC (silica, DCM/MeOH as eluent) to obtain compound 5.

Compound 6

Compound 5 (0.8 g) is dissolved in MeOH (15 ml), then ethyltrifluoroacetate (1.8 mL) and triethylamine (3 mL) are added and reaction is stirred for 6-8 h. Solvent is evaporated to dryness, and crude product is purified by CC (silica, DCM/MeOH as eluent) to obtain compound 6.

Compound 7

Compound 6 is dissolved in THF (40 mL) and a solution of 1M TBAF (23 mL) in dry THF is added. The mixture is stirred for 16 h, then worked-up with EtOAc/water, and evaporated to dryness. Crude product is purified by CC (Silica gel, DCM/MeOH as eluent).

Compound 8

Compound 7 (2 g) and DCI (137 mg) are dissolved in dry freshly distilled DCM (30 mL). PCl-reagent (0.8 ml) is then added drop wise and the mixture is stirred for 1 hr. Crushed ice is added and the mixture is extracted with DCM (2×20 ml), the combined organic phase washed with cold brine, dried, and DCM evaporated. The crude product is purified by chromatography (eluent: pentane/EA/Et3N) to give a colorless to off-white oil useful for incorporating into an oligonucleotide.

Compound 9:

6-aminohexanol (1 g) is dissolved in dry pyridine (10 mL), then TBDMS-Cl (1.5) is added. The mixture is stirred for 8 h, then solvent is evaporated to dryness under reduce pressure. Working up is performed with DCM/water, and solvent is evaporated to obtain crude product 9. Crude product is purified by CC (silica, DCM/MeOH as eluent).

Example 3

Synthesis of Chimeric Oligonucleotides

The sphingolipid-polyalkylamine phosphoramidites were incorporated into oligonucleotides by coupling to the oligonucleotide strand during synthesis, in particular into antisense strands and/or sense strands useful in generating antisense oligonucleotide compounds or double-stranded RNA nucleic acid molecules, including siRNA, siNA, antimiR and miRNA.

For large scale synthesis (20 µmol), sphingolipid-polyalkylamine phosphoramidite (300 mg) was dissolved in acetonitrile (1.65 ml, 0.15M). Sphingolipid-polyalkylamine was coupled twice (Coupling time was 10 min for each coupling step).

Cleavage and De-Protection of siRNA-Sphingolipid-Polyalkylamine

For an oligonucleotide strand (e.g. siRNA strand) bound to resin (344 mg), NH$_4$OH (33% in water): Methylamine (33% in EtOH) were added (v/v; total 3.44 ml) in a sealed tube and incubated for 3.5 h at 65° C. in a heat block. After 3.5 h the tube was cooled to RT and the resin was spin down in a centrifuge at 4000 rpm for 5 min. The supernatant was decanted to a fresh tube and washed twice with EtOH: H$_2$O (3.5 ml×2). The supernatants were combined and dried by lyophilizer. After the oligonucleotide was dried, DMSO (0.344 ml) and TEA 3HF (3.44 ml) were added in a sealed tube and incubated for 3 h at 65° C. in a heat block. After this period, the oligonucleotide was cooled to RT and further cooling to −20° C. The oligonucleotide was precipitated with pre-cooled BuOH.

The siRNA-sphingolipid-polyalkylamine compounds were purified on HPLC due to two peaks that obtained. Peak 1 is the desire siRNA conjugate to sphingolipid-polyalkylamine and peak 2 is the same conjugate, but with TFA protecting group.

Similar methods are used for coupling single stranded and other double stranded oligonucleotide molecules.

Inventors have shown that a sphingolipid-polyalkylamine dsRNA compound exhibits enhanced cellular uptake and endosomal escape compared to an unmodified dsRNA molecule.

Example 4

In Vitro Knockdown Activity of Sphingolipid-polyalkylaminesiRNA Compounds (SL-Spermine and SL-Spermidine)

In vitro knockdown activity of a target gene by sphingolipid polyalkylamine siRAC1 compounds, sphinglolipid-spermine (SL-Spermine-RAC1_28_S2045) or sphingolipid spermidine (SL-Spermidine RAC1_28_S2081) was analyzed and compared to activity of non-conjugated siRNA (RAC1_28_S1908). Target knockdown activity was studied using the psiCHECK™ system.

The psiCHECK™ expression system (Promega) enables the evaluation of the intrinsic potency of inhibitory oligonucleotides, e.g. siRNA or antisense, by monitoring the changes in the activity of Luciferase reporter gene carrying the target sites for inhibitory oligonucleotide action in its 3' untranslated region (3'-UTR). The activity of a siRNA toward this target sequence usually results either in cleavage and subsequent degradation of the cleaved mRNA. or translation inhibition of the protein encoded by the target gene. In addition, the psiCHECK™-2 vector contains a second reporter gene, Firefly luciferase, transcribed from a different promoter and unaffected by the inhibitory oligonucleotide under study. This allows for normalization of *Renilla* luciferase expression across different transfections.

psiCHECK™-2-based construct was prepared for the evaluation of the on-target activity of the guide strands (GS, antisense) of RAC1 siRNAs, the off target activity of the guide strand seed sequence (GS-SM) and/or the target activity of the passenger strand (PS-CM, also referred to as off target activity of an siRNA). In the construct, one copy of the full target sequence of the test molecules GS was cloned into the multiple cloning site located in the 3'-UTR of the *Renilla* luciferase, downstream to the stop codon. The psiCHECK™-2 plasmid was transfected into human HeLa cells. The transfected HeLa cells were seeded into the wells of a 96-well plate and incubated at 37° C. with the siRNA of interest added in duplicates without transfection reagent. The final concentrations of the RAC1 siRNA compounds tested were 0.03, 0.1, 0.3, and 1 µM. Control cells were not exposed to any siRNA.

48 hours following siRNA transfection, the cells were harvested for protein extraction. *Renilla* and FireFly Luciferase activities were measured in individual cell protein extracts using Dual-Luciferase® Assay kit according to the manufacturer procedure. *Renilla* Luciferase activity values were normalized by Firefly Luciferase activity values obtained from the same samples. siRNA activity was expressed as percentage of residual normalized *Renilla* Luciferase activity in a test sample from the normalized *Renilla* Luciferase activity in negative control cells.

Figure 2:
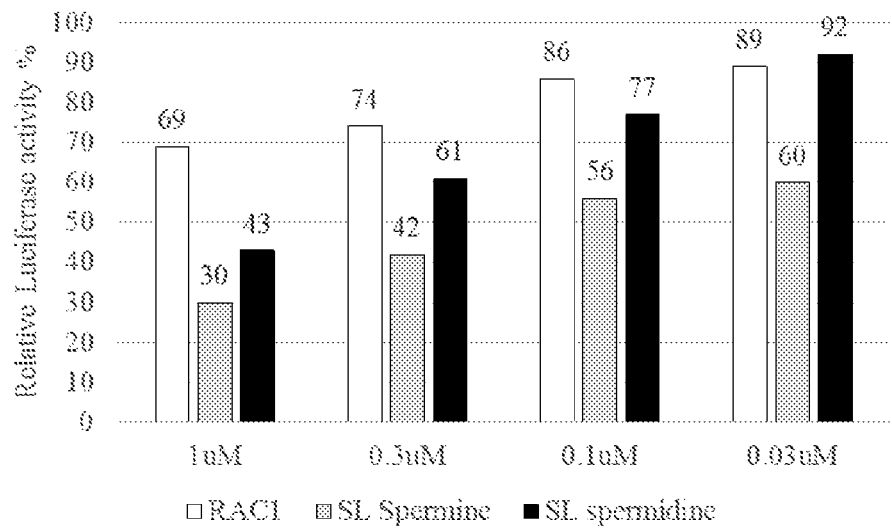
FIG. 2 is a graph showing 2, dose-dependent knockdown of *Renilla* Luciferase activity by sphingolipid polyalkylamine siRNA compounds but not for their non-conjugated counterparts.

The study was repeated at least twice and representative results are shown in FIG. 2.

As shown in FIG. 2, dose-dependent knockdown of *Renilla* Luciferase activity was demonstrated for all sphingolipid polyalkylamine siRNA compounds tested but not for their non-conjugated counterparts.

Example 5

In-Vitro Knockdown Activity of Sphingolipid-Spermine-siRNA Compounds

In vitro knockdown activity of target genes, KRAS and PLK1, by siRNA duplexes conjugated to sphingolipid spermine (SL-Spermine-KRAS_2_S2309 and SL-Spermine-PLK1_28_S2272, respectively) was analyzed and compared to activity of non conjugated siRNA (KRAS_2_S2087 and PLK1_28_S2054, respectively). Target knockdown activity was studied using the psiCHECK™ system, as described above in Example 4. The study was repeated at least twice and representative results are shown in FIG. 3.

Figure 3:
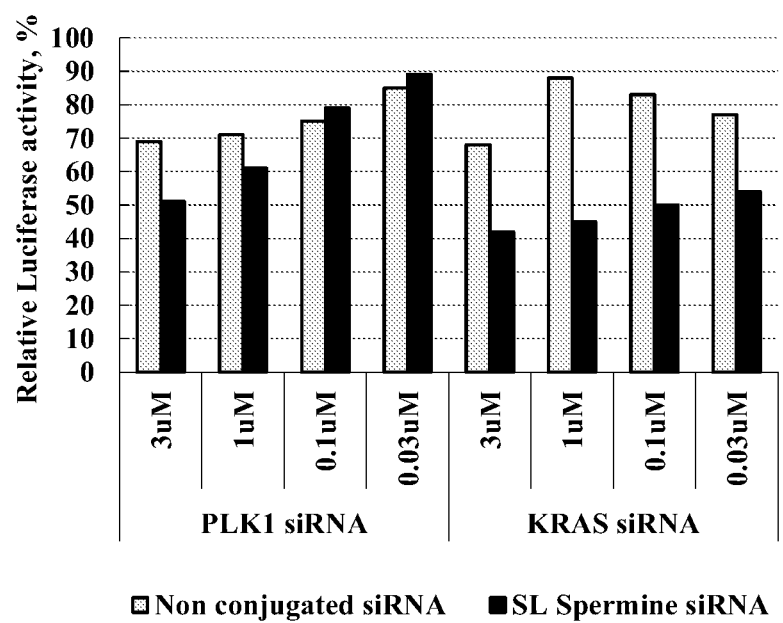
FIG. 3 is a graph showing dose-dependent knockdown of *Renilla* Luciferase activity for sphingolipid-spermine siRNA compounds but not for their non-conjugated counterparts.

As shown in FIG. 3, dose-dependent knockdown of *Renilla* Luciferase activity was demonstrated for all sphingolipid-spermine siRNA compounds tested but not for their non-conjugated counterparts suggesting that the activity we observe is not siRNA sequence dependent.

Example 6

Stability of Sphingolipid-Spermine siRNA Compounds in Plasma and Cell Extract

The stability of sphingolipid spermine RAC1_28 siRNA compounds against degradation by nucleases was analyzed n plasma and cell extract.

The sphingolipid-polyalkylamine siRNA compounds were incubated for 24 hours at 37° C. in mouse plasma and Ct26 cell extract. At time points between 0 and 24 hours after incubation, 1 ng aliquots were transferred to TBE-loading buffer, snap frozen in liquid nitrogen and stored at −20° C. until use. The aliquots were thawed on ice and analyzed by non-denaturing polyacrylamide gel electrophoresis.

Figure 4:
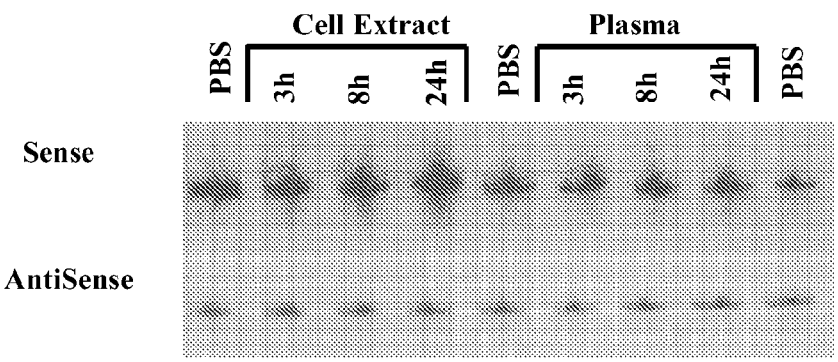
FIG. 4 is a picture of a PAGE gel showing stability of the sense and antisense strands of a sphingolipid-spermine siRNA in cell extract and in plasma.

Based on the gel migration patterns, presented in FIG. 4, the sphingolipid spermine siRNA tested, were found to be stable for at least 24 hours at 37° C. in plasma and cell extract.

Example 7 pK of Sphingolipid-Spermine and Sphingolipid-Spermidine siRNA-Compounds

In the present experiment the pharmacokinetics (Pk) of the sphingolipid-spermine and sphingolipid-spermidine RAC1 siRNA compounds in plasma was compared to the non-conjugated RAC1 siRNA following i.v. administration of 1 mg/kg siRNA to Rats. At 10 min, 30 min, 1 h, 4 h, 8 h and 24 h after the siRNA administration, blood samples (around 50 μl of total volume from tail) were collected, into EDTA collecting tubes. Collected blood samples obtained from all animals were processed for plasma separation by centrifugation (2500 g, for 15 minutes at room temperature). The siRNA was extracted from the plasma using Triton X-100 extraction. For determining the RAC1 siRNA levels in the samples cDNA was prepared using the Stem loop method for siRNA detection. qPCR was carried out standard protocols. In a slight variation to the protocol the SYBR fast ABI prism Ready mix kit (KAPA cat no.KK-KK4605) was used with an elongation/extension time of 30 secs. 0.4 μl of each primer and 6.4 μl of water was used per sample in the reaction mix.

Figure 5:
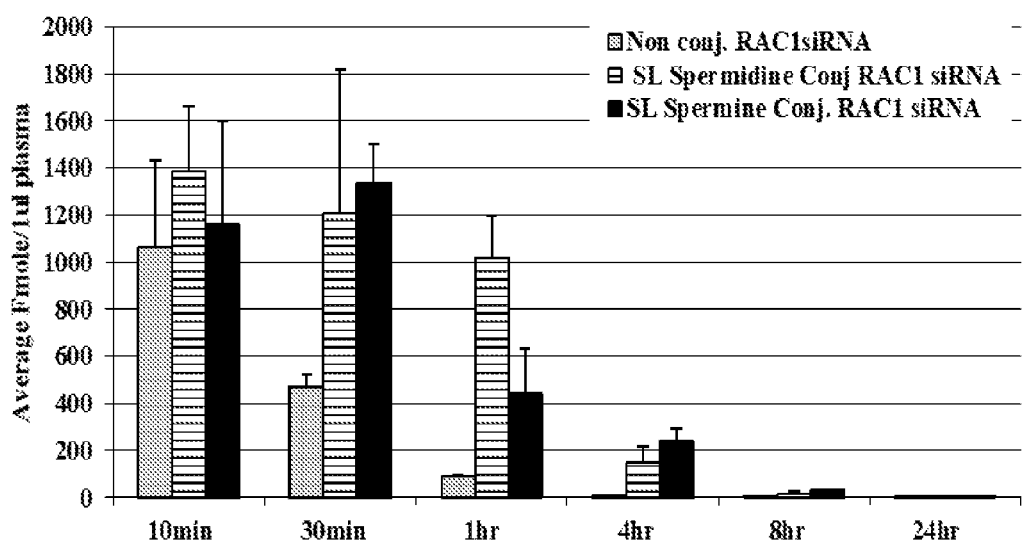
FIG. 5 is a graph showing levels of sphingolipid spermine siRNA compounds in plasma.

The results are presented in FIG. 5. As can be seen in FIG. 5, the level of the sphingolipid spermine siRNA compounds in plasma was higher than the non-conjugated siRNA at all time points examined. For example at 1 h from i.v. injection less than 10% of the non conjugated siRNA was found in plasma while more than 70% of the SL-spermine siRNA compound (and more than 30% of the sphingolipid-spermidine siRNA compound, data not shown) could be detected in plasma suggesting higher retention and longer circulation time for the sphingolipid spermine and sphingolipid spermidine siRNA compounds.

Example 8

Cytokine Induction in PBMC of Sphingolipid-Polyalkylamine siRNA Compounds

Sphingolipid spermidine RAC1 siRNA compound (RAC1_28_S2081) and sphingolipid spermine RAC1 siRNA compound (RAC1_28_S2054) were diluted in PBMCs Growth Medium to the concentrations of 400, 200 and 20 nM. RAC1_28_S1908 was tested at the concentration of 400 nM. LPS was dissolved with Water, Cell Culture Grade, to achieve a stock solution of 2000 μg/ml.

PBMCs were isolated from a pool of fresh blood of 3 healthy human donors obtained from the Blood Bank as following. Whole blood was diluted 1:2 (10 ml+10 ml) with RPMI 1640. Diluted blood was gently overlaid onto Lymphoprep (1:3 ratio) and centrifuged at 22° C., 900 g, for 25 minutes (break off). Opaque-light PBMCs ring was removed from the interphase of each donor into a new 50 ml tube to create a pool of the donors. PBMCs were washed with a total of 40 ml RPMI 1640 and centrifuged 800 g for 10 min. Afterwards, pelleted cells were re-suspended in 40 ml PBMCs Growth Medium. PBMCs were counted with automated cell counter (TC20; BioRad). Cells were re-suspended with PBMCs Growth Medium to a final concentration of $3*10^6$/ml. One ml of cell suspension of each PBMCs pool was divided into each well of 12 well plates. In each well, siRNA, negative and positive controls were added in triplicates to achieve the final concentrations. Plates were incubated at 37±1° C. humidified, 5±0.5% $CO_2$/air. After 24±2 hours of incubation period, cells were collected, centrifuged at 800 g for 7 min and supernatant was removed, divided into 2 aliquots and stored in [(−70)-(−80°) C.] freezer for quantification of IL-6 and TNF-α secreted cytokines. IL-6 and TNF-α cytokines levels were determined using Human DuoSet ELISA kits (R&D Systems), according to the manufacturer's instructions. For the IL6 ELISA, PC sample were diluted 1:100 and 1:1000 in the kit's reagent diluent. For the TNFα ELISA, PC samples were diluted 1:10 and 1:50 kit's reagent diluent. Test Items, in both ELISAs, were examined as undiluted and diluted 1:5 in the kit's reagent diluent.

Figure 6A:
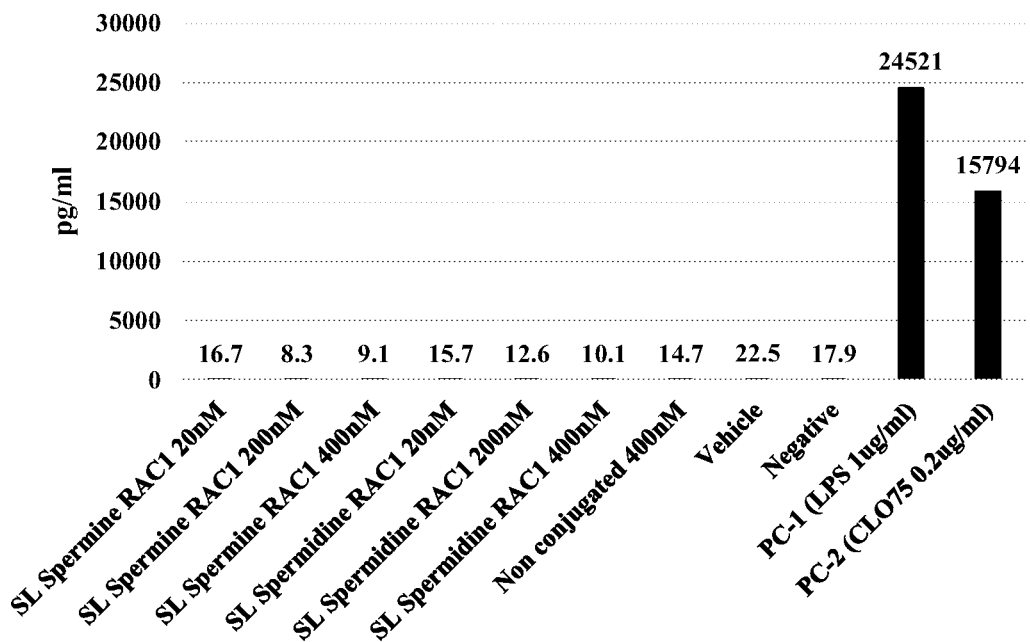
FIGS. 6A, 6B and 7 are graphs showing results that the sphingolipid-polyalkylamine siRNA compounds do not elicit an immune response.
Figure 6B:
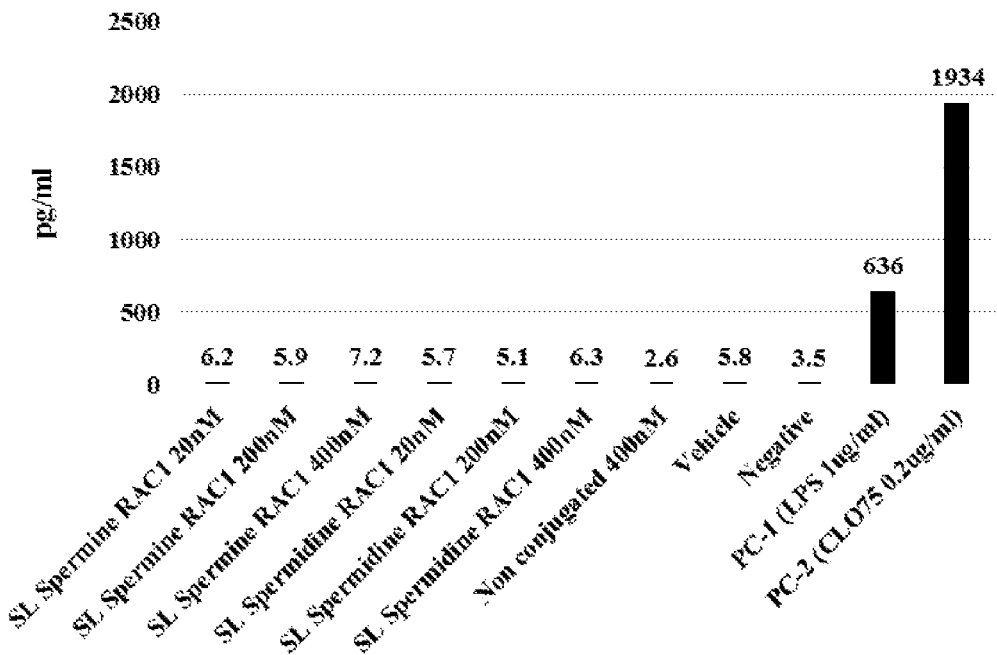

The level of IL-6 and TNFα is presented in FIGS. 6A and 6B.

As shown in FIG. 6A, following 24 hours of incubation with PBMCs, the Positive Controls treatments (LPS and CL075) induced high and significant IL-6 secretion, in comparison to the Negative Control (Growth medium) treatment. No significant induction of IL-6 cytokine secretion was observed in any of the siRNA including the sphingolipid spermine and sphingolipid spermidine siRNA compounds.

As shown in FIG. 6B, following 24 hours of incubation with PBMCs, the Positive Controls treatments (LPS and CL075) induced high and significant TNFα secretion, in comparison to the Negative Control (Growth medium) treatment. No significant induction of TNFα cytokine secretion was observed in any of the siRNA including the sphingolipid spermine and sphingolipid spermidine siRNA compounds.

Example 9

IFN Responsive Gene Activation in PBMC

Fresh human blood (at RT) was mixed at 1:1 ratio with sterile 0.9% NaCl at RT, and gently loaded (1:2 ratio) on Ficoll (Lymphoprep, Axis-Shield cat #1114547). Samples were centrifuged at RT (22° C., 800 g) in a swinging centrifuge for 30 minutes, washed with RPMI1640 medium and centrifuged (RT, 250 g) for 10 minutes. Cells were counted and seeded at final concentration of $1.5 \times 10^6$ cell/ml in growth medium (RPMI1640+10% FBS+2 mM L-glutamine+1% Pen-Strep) and incubated for 1 hours at 37° C. before exposure to sphingolipid-polyalkylamine siRNA compounds. Cells were treated (contacted) with the test siRNAs at different concentrations using the Lipofectamine®2000 reagent (Invitrogen) according manufacturer's instructions and incubated at 37° C. in a 5% $CO_2$ incubator for 24 hours.

As a positive control for IFN response, cells were treated with either poly(I:C), a synthetic analog of double strand RNA (dsRNA) which is a TLR3 ligand (InvivoGen Cat# tlrl-pic) at final concentrations of 0.25-5.0 µg/mL or to Thiazolaquinolone (CLO75), a TLR 7/8 ligand (InvivoGen Cat# tlrl-c75) at final concentrations of 0.075-2 µg/mL. Cell treated with Lipofectamine®2000 reagent were used as negative (reference) control for IFN response.

At about 24 hours following incubation, cells were collected and supernatant was transferred to new tubes. Samples were frozen immediately in liquid nitrogen and secretion of IL-6 and TNF-α cytokines was tested using IL-6, DuoSet ELISA kit (R&D System DY2060), and TNF-α, DuoSet ELISA kit (R&D System DY210), according to manufacturer's instructions. RNA was extracted from the cell pellets and mRNA levels of human genes IFIT1 (interferon-induced protein with tetratricopeptide repeats 1) and MX1 (myxovirus (influenza virus) resistance 1, interferon-inducible protein p78) were measured by qPCR. Measured mRNA quantities were normalized to the mRNA quantity of the reference gene peptidylprolyl isomerase A (cyclophilin A; CycloA). Induction of IFN-signaling was evaluated by comparing the quantity of mRNA from IFIT1 and MX1 genes from treated cells, relative to their quantities non-treated cells. The qPCR results are those that passed QC standards, i.e. the value of the standard curve slope was in the interval [−4, −3], $R^2 > 0.99$, no primer dimers. Results that did not pass the QC requirements were disqualified from analysis.

Figure 7:
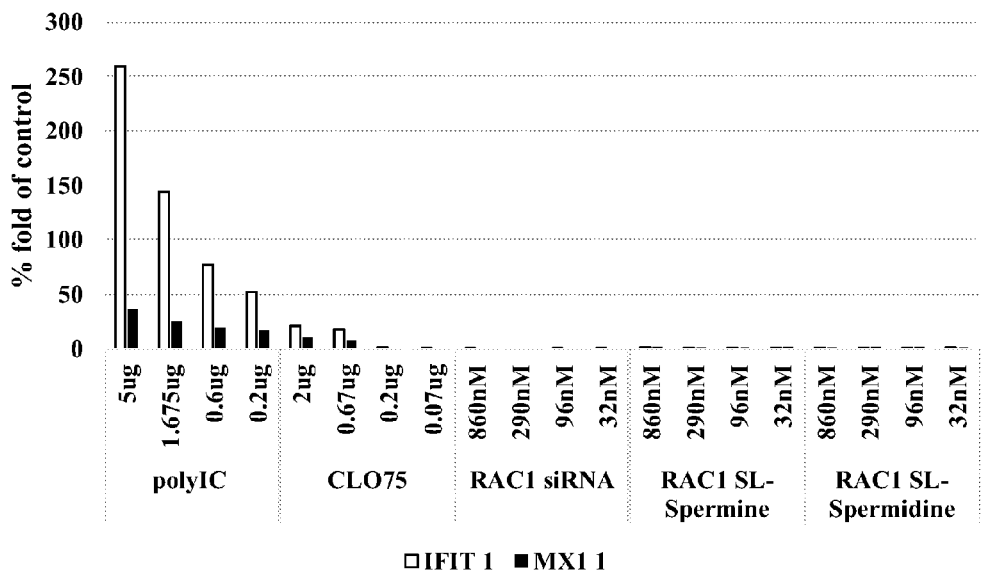

The levels of MX1 and IFIT mRNA in sphingolipid spermine and sphingolipid spermidine siRNA compound treated cells are presented as fold of control treated As can be seen in FIG. 7 an increase in the expression levels of two of the genes tested (IFIT1 and MX1) after treatment with the positive control CL075 and Poly (I:C). There is no significant change in the expression levels of MX1 and IFIT genes following treatment with all siRNA, including the non conjugated siRNA at all concentrations tested.

Example 10

Complement Activation in PBMC

The potential of sphingolipid spermine and sphingolipid spermidine siRNA compounds to activate complement in human plasma was examined using an enzyme immunoassay for the quantification of the complement terminal SC5b-9 complex. Normal human plasma was thawed quickly at 37° C. and immediately transferred to ice. The plasma was divided into 80 µl samples and 20 µl of the following items were added. The following control were used: Positive control solutions included: Zymosan, CVF, and complement Activator. Negative control (saline) solution and 50 mM EDTA inhibitor control solution (ratio 1:5). siRNA and saline were added directly to plasma as noted in the Study Protocol. Tubes were incubated at 37° C. for 1 hr with gentle shaking Samples were plunged in ice, and the complement reactions were stopped by addition of 24 µl of 50 mM EDTA and vortex well. Particles were removed from the serum sample by centrifugation (20,000 g×10 min at 4° C.). Supernatant was removed to a new tube and freeze at −80° C. until subjected to analysis of SC5b-9 quantification. For ELISA supernatants were diluted 1:10 with Specimen Diluent. The SC5b-9 levels were determined using SC5b-9 ELISA kit according to the manufacturer's instructions.

Figure 8:
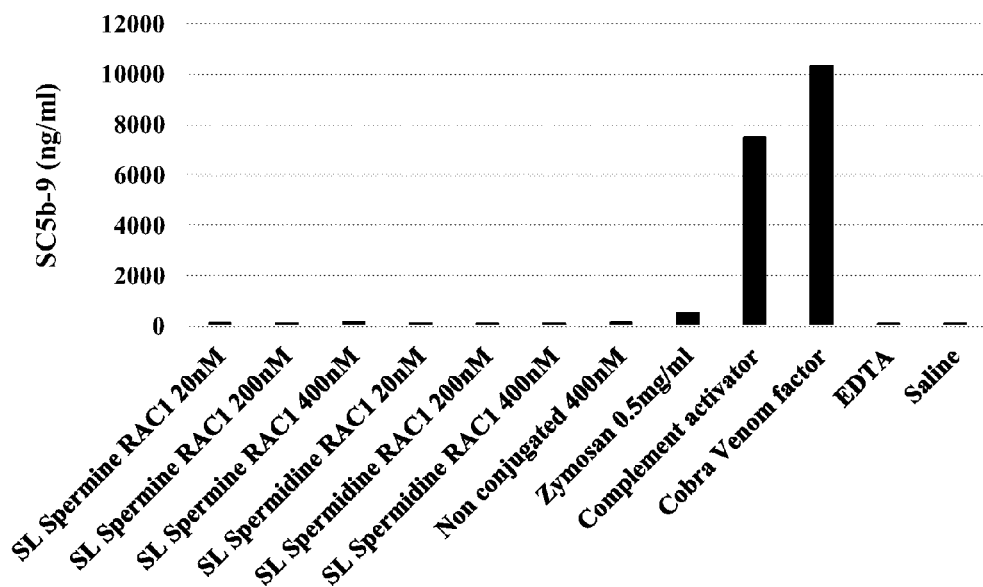
FIG. 8 is a graph showing results that the sphingolipid-polyalkylamine siRNA compounds do not activate complement

The levels of SC5b-9 are presented in FIG. 8. As can be seen in FIG. 8 the sphingolipid spermine and sphingolipid spermidine siRNAs did not induce generation of SC5b-9 complex and thus, do not activate complement in human plasma.

Example 11

In Vivo Toxicity in Rat

The potential toxicity of the unconjugated siRNA (RAC1_28_S1908), sphingolipid spermine siRNA (SL-Spermine-RAC1_28_S2045), and sphingolipid-spermidine siRNA (SL-Spermidine-RAC1_28_S2081) was assessed following a single intravenous (IV) administration of 2 escalating dose levels and their respective controls in BALB/c mice.

Animals were subjected to a single bolus IV injection into one of the tail veins at either 10 mg/kg or 50 mg/kg siRNA dose. Each group comprised of 6 males and 6 females BALB/cOlaHsd mice, where half of each group (3 males and 3 females) were assigned to 24 hour or 7 days termination time points Animals were subjected to clinical hematology and biochemistry assessment at 24 hours and 7 days post dosing, followed by gross macroscopic examination.

Mortality: No mortality occurred in any of the animals throughout the 7-Days study period. Clinical Signs: No abnormal clinical signs were noted in any of the animals on the day of dosing and throughout the entire study period. Body Weight and Body Weight Gain: Mean group body weight and gain values appeared similar in all study groups and no statistical differences were noted when treated test groups compared to the saline control group.

Hematology and Biochemistry: All hematology and biochemistry parameters of both males and females of the test groups, at the 1 and 7 days time points, appeared to be similar to those of the Saline control. Some statistically significant changes were noted in both males and females of the test groups at both termination time points in the platelets and ALT parameters; however all values were within the normal expected range for this strain of mice and did not appear to have any biological effect.

Macroscopic Examination: No gross pathological findings were noted in any of the animals at each termination time point. In view of the reported findings and under the conditions of this study it may be concluded that a single bolus IV injection of up to 50 mg/kg of RAC1_28_S2045 and 10 mg/kg of RAC1_28_S2081 may be consider safe, toxicity wise, since no apparent effect in mortality, observed clinical signs, body weight, clinical pathology and adverse effect in gross lesions at necropsy were noted.

In view of the reported findings it may be concluded that a single bolus IV injection of up to 50 mg/kg of sphingolipid-spermine siRNA and 10 mg/kg of sphingolipid-spermidine siRNA are safe, toxicity wise, since no apparent effect in mortality, observed clinical signs, body weight, clinical pathology and adverse effect in gross lesions at necropsy were noted.

In order to evaluate the siRNA biodistribution in normal mice, liver, spleen and bone marrow and examined the level of siRNA delivered to these tissues. 24 hours post iv injection mice were euthanized, tissues-harvested, and subjected to siRNA quantification by Stem and Loop qPCR method.

Total RNA was prepared from retina samples using EZ-RNA II Total RNA Isolation Kit (Biological Industries, #20-410-100). In some cases triton extracts were prepared from the retina samples: retina samples were weighed and ×10 volume of 0.25% preheated Triton X-100 was added to each sample. The mixtures were vortexed, incubated at 95° C. for 10 min, cooled on ice (10 min) and finally centrifuged (20,000 g, 20 min, 4° C.). Supernatants were collected.

For specific amplification of the siRNA contained in the total RNA samples (or in the triton extracts), complementary DNA (cDNA) was prepared by a reverse transcription (RT) reaction using Superscript II kit (Invitrogen, #18064-014), 1 µg total RNA (or 5 µl triton extract supernatant) as template and a stem & loop (S&L) primer, which is partially complementary to the antisense strand of the subject siRNA and in addition, harbors a stem & loop structure at its 5'-end.

```
RT primers:
For RAC1_28 amplification:
1648-2/Rac128ASRT
                                            (SEQ ID NO: 11)
GTCGTATCCAGTGCAGGGTCCGAGGTATTCGCACTGGATACGACCG
TGCAA
```

The resulting cDNA served as a template for siRNA amplification using the SYBER-Green based quantitative PCR (qPCR) method (SYBR Green Master Mix, Applied Biosystems; #4309155) and two amplification primers: one complementary to the siRNA sequence and the second complementary to the stem & loop region of the RT primer.

```
qPCR primers:
RAC1_28
1695-3/Rac128ASF2
                                            (SEQ ID NO: 12)
CGGCGGCAGGATACCACTTTG 1681-1/Rev_3
                                            (SEQ ID NO: 13)
AGTGCAGGGTCCGAGGTATT
```

For absolute quantification of siRNA in the test samples, standard curves were generated by the spiking of several known siRNA quantities (10-3 pmols) into retina extracts followed by RNA extraction and cDNA preparation as described above. Serial dilutions prepared from the spiked samples cDNA, were amplified by qPCR. The resulting Ct values (Ct=Threshold Cycle, the PCR cycle in which fluorescence level exceeds a chosen threshold limit) obtained in each reaction, were plotted against the corresponding ($Log_{10}$) siRNA quantity values for the generation of a standard curve, which was used for the quantification of siRNA in unknown samples by interpolation.

Figure 9A:
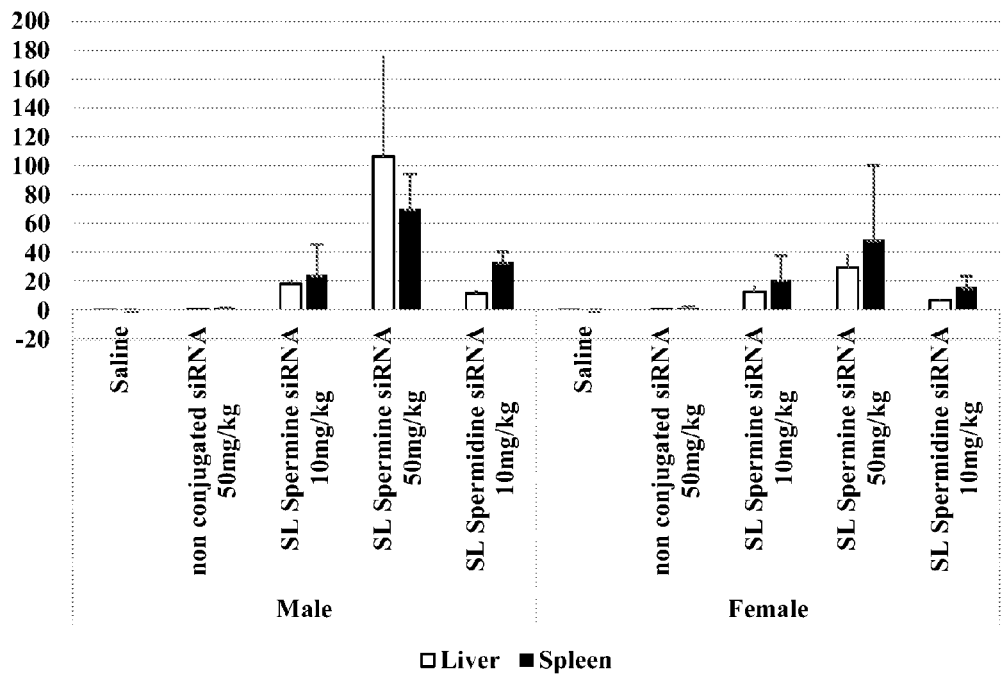
FIGS. 9A and 9B are graphs showing levels of accumulation of the sphingolipid-polyalkylamine siRNA compounds in liver and spleen.
Figure 9B:
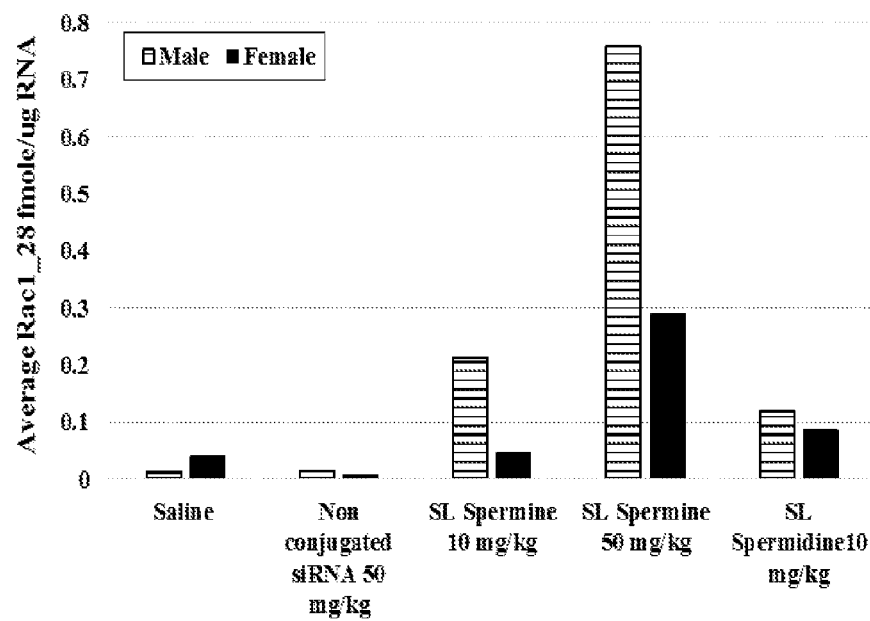

FIGS. 9A and 9B present the quantitative amount of each siRNA in the different tissues. As can be seen in FIGS. 9A and 9B dose dependence accumulation of sphingolipid spermine siRNA compounds was observed in both spleen, liver and bone marrow. Moreover, a significantly higher amount of siRNA was identified in the spleen, liver and bone marrow in mice treated with the sphingolipid-spermine siRNA compared to amount of siRNA identified in tissues taken from mice treated with non-conjugated siRNA, reaching up to ~100 fold higher accumulation of the sphingolipid spermine siRNA in liver compared to the non conjugated siRNA (at a 50 mg/kg siRNA dosage)

Example 12

Sphingolipid-Spermine siRNA Compounds Show Improved Accumulation in Mice LLC1 Tumor Tissue In the present experiment, the concentrations of sphingolipid-spermine siRNA (SL-Spermine RAC1_28_S2045 and RAC1_28_S2081) and non conjugated RAC1 siRNA (Rac1_28_S1908) compounds were determined in LLC1 tumors 24 hours following continuous subcutaneous (SC) delivery by implanted ALZET micro osmotic pumps (Model: ALZET osmotic pump 2001D model, 200 µl, 80 µl/h, 1 day, Corp., Cupertino, Calif.) at 30 mg/Kg dose in C57BL mice bearing solid Lewis Lung Carcinoma (LLC1) tumors on their flanks. Each experimental group included 6 C57BL mice bearing solid Lewis Lung Carcinoma (LLC1) tumors on their flanks. 48 hours post pump implantation, mice were euthanized, and tumors were harvested, and subjected to siRNA quantification by Stem and Loop qPCR method.

Figure 10:
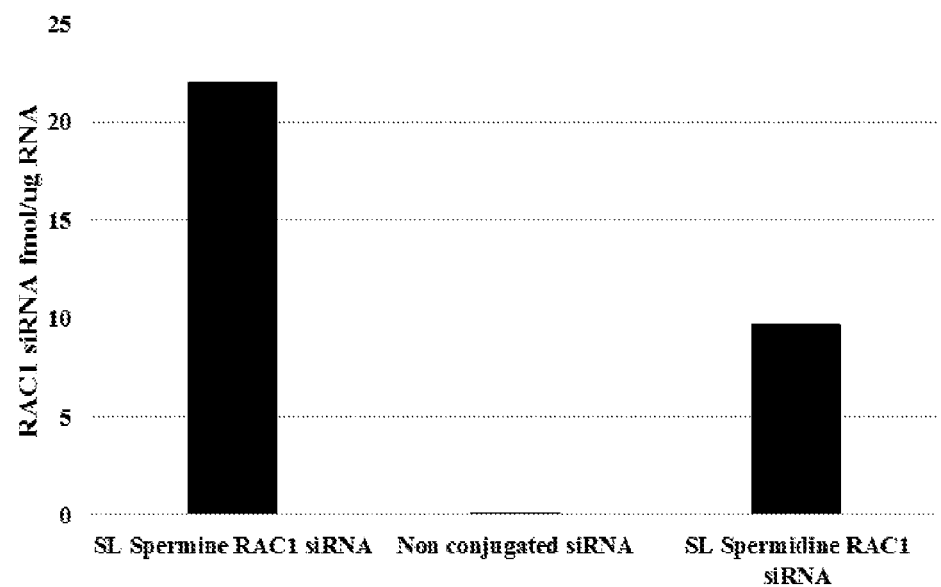
FIG. 10 is a graph showing levels of accumulation of sphingolipid-polyalkylamine siRNA compounds in LLC1 tumor cells following subcutaneous administration.

The level of siRNA delivered to the LLC1 tumor cells from mice treated with 30 mg/kg sphingolipid polyalkylamine siRNA compounds was significantly higher than the amount of siRNA accumulated in tumor cells from mice treated with 30 mg/kg non conjugated siRNA. As can be seen in FIG. 10 ~150 fold higher amount siRNA could be found in tumor cells taken from mice treated with the sphingolipid-spermine siRNA and ~60 more siRNA in tumor cells taken from mice treated with the sphingolipid-spermine siRNA compound compared to the mice treated with the same amount of non conjugated siRNA compound.

Example 13

Knockdown Activity of Sphingolipid-Spermine siRNA Compounds Targeting RAC1 mRNA in Mice SKOV3 Tumors The RNAi-mediated cleavage of RAC1 mRNA in mice SKOV tumors following 3 ip administrations of 10 mg/kg of the sphingolipid-spermine siRNA (RAC1_28_52045) was confirmed by Rapid Amplification of cDNA Ends (RACE). RNAi-mediated cleavage of a target mRNA occurs between nucleotides complementary to bases 10-11 of the siRNA guide strand to produce two mRNA fragments: a 5' fragment representing the region upstream to the cleavage site and the 3'-fragment representing the region downstream to the cleavage site. The presence of the downstream fragment can be detected using the RACE method, which is based on the ligation of an oligonucleotide adapter to the 5' end of this fragment, followed by RT-PCR amplification using adapter-specific forward and gene-specific reverse primers.

RNA was extracted from SKOV3 tumor samples 24 hours after intraperitoneal (i.p.) injection of the compounds listed in Table 3 and subjected to RACE analysis. Amplification products were analyzed by Southern blot hybridization with an oligonucleotide probe specific for the predicted mRNA-RACE adaptor junction. Cells transfected with 20 nM of RAC1 served as the positive control.

Figure 11:
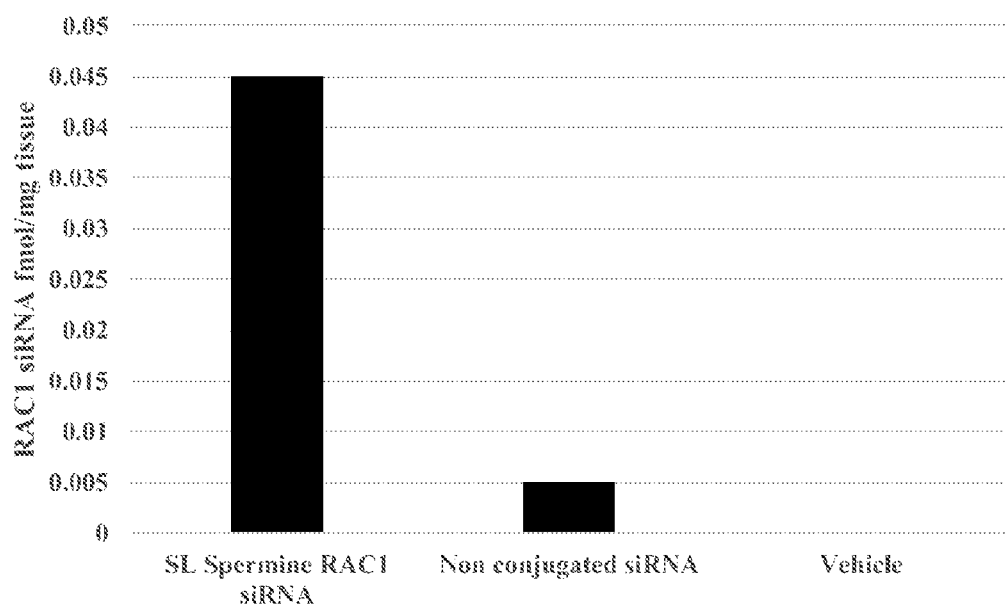
FIG. 11 a graph showing levels of accumulation of sphingolipid-polyalkylamine siRNA compounds in LLC1 tumor cells following subcutaneous administration.
Figure 12:
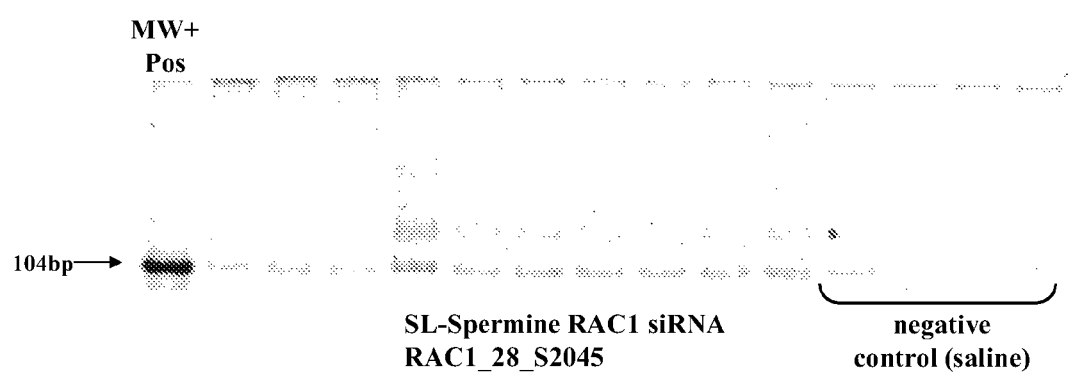
FIG. 12 is a picture of a PAGE gel showing the RACE product from RNAi-mediated cleavage of RAC1 mRNA by sphingolipid-spermine siRAC1 compound in tumors.

The results, presented in FIG. 11 indicate the generation of the specific proper RT-PCR (RACE) product predicted for RNAi-mediated cleavage of RAC1 mRNA by conjugated siRNA. However, RACE product was observed only in RNA samples derived from eyes injected with control saline.

Example 14

Cell Penetration of Sphingolipid-Spermine Cy3 Labeled siRNA, RAC1_28_S2281 microscopy The purpose of this study was to determine penetration of RAC1_28_S2132 (non conjugated Cy3 siRNA) and RAC1_28_S2281 (SL-Spermine Cy3 siRNAs) to cells. The study included siRNA treatments followed with immuno-fluorescent staining (IF) with early endosome marker- (EEA1). Cells were analyzed in order to define co-localization of both components (siRNA and early endosome) along the tested time points.

Stained cells were analyzed under ApoTome optical sectioning in the fluorescent microscope. Images represented in Cut-view format with Maximal Intensity Projection (MIP). Cut-view function creates 2D image of all optical sectioning images taken. In order to determine state of co-localization of the siRNA with the early endosome, a color shift consideration alone is not reliable, and the use of analytical software for image analysis is essential in such study. In the following analysis AxioVision properties (profile and histogram) were used to process the Z-stack images, from all tested siRNA's and to evaluate selected areas for co-localization.

TABLE 3 detection of cells that display co-localization with EEA1

| Co-localization | Rac1_28_S2132 (naked) | Rac1_28_S2281 (SL) |
|---|---|---|
| 1 h | − | − |
| 2 h | − | + |
| 3 h | − | + |
| 4 h | − | + |
| 6 h | − | + |

As can be seen in Table 3, Cells treated with sphingolipid spermine siRNA compounds display co-localization of the siRNA with early endosome at time points 2 h, 3 h, 4 h and 6 h. This co-localization was not observed with the non-conjugated siRNA, which showed only faint signal in the cells.

Example 15

Cell Internalization Kinetics by FACS

In the present study the internalization kinetics of the sphingolipid-spermine siRNA compound (RAC1_28_S2281) was analyzed. HeLa cells were grown in DMEM, supplemented with 10% fetal bovine serum 4 mM L-Glutamine at 37 C with 5% CO2.

Figure 13A:
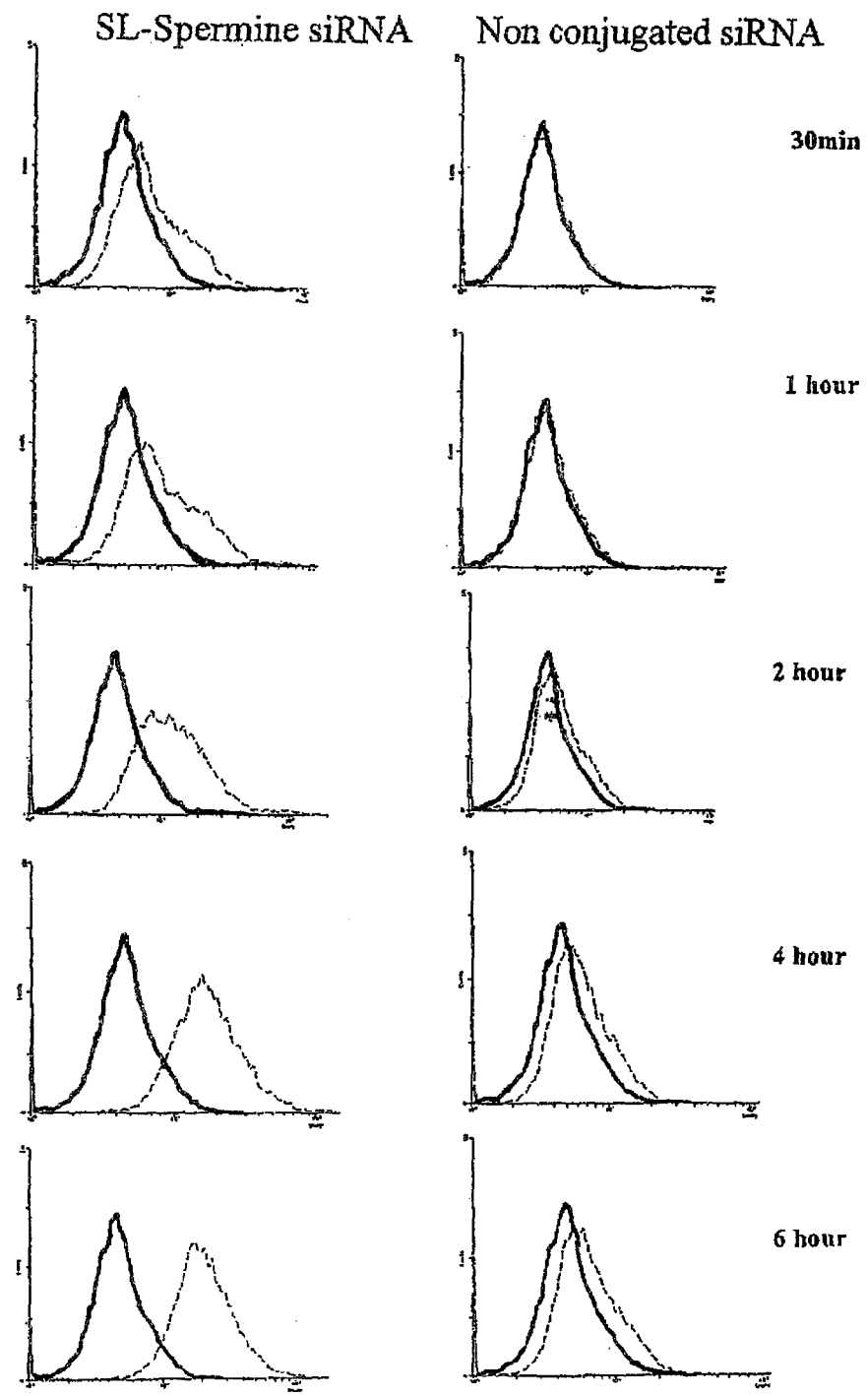
FIGS. 13A and 13B show FACS shifts of untreated and sphingolipid-spermine siRNA treated cells.
Figure 13B:
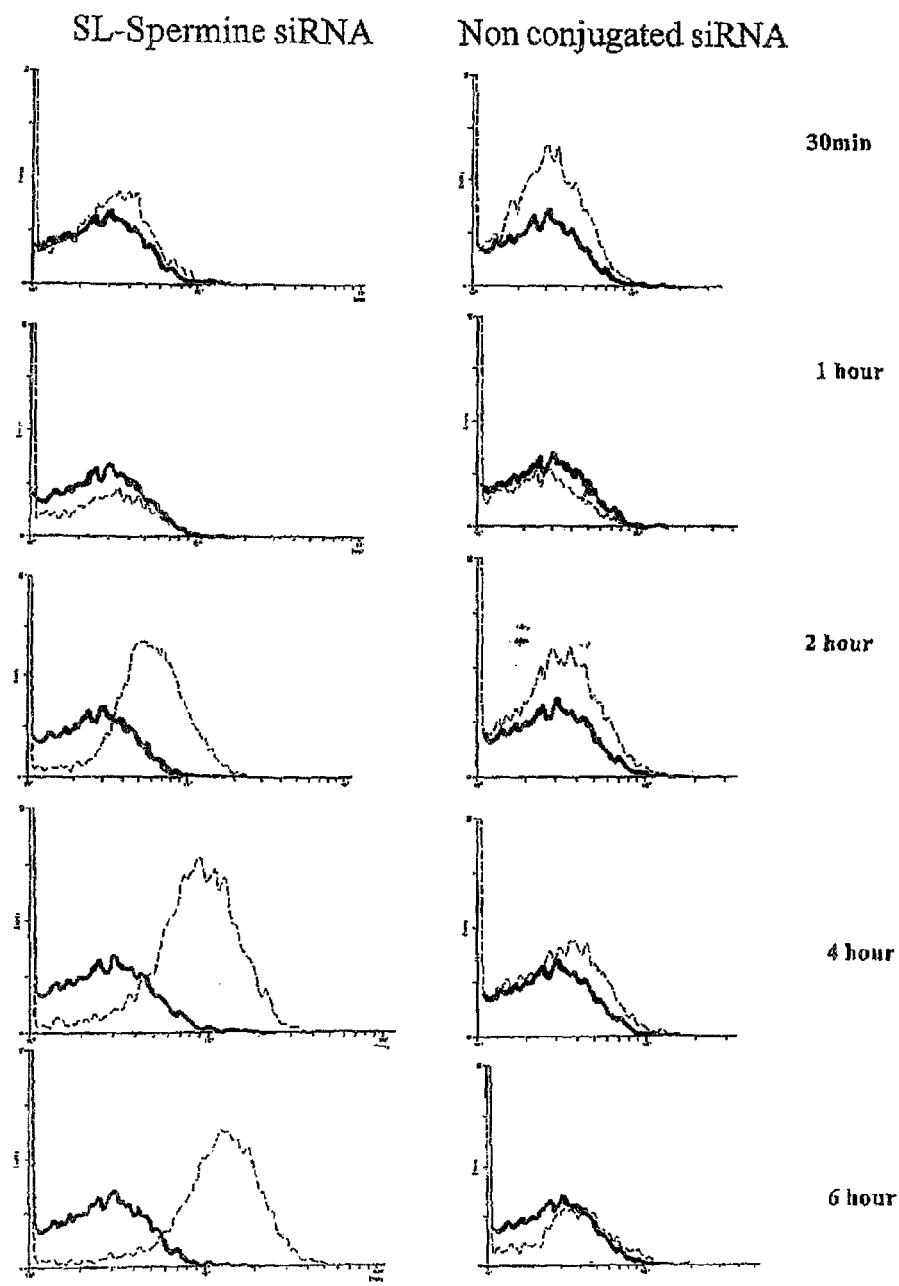

The cells were seeded in 6-well tissue culture plates a day before treatment. The staining procedure included incubation of cells with 100 nM of either sphingolipid-spermine siRNA compound (RAC1_28_S2281) or non conjugated control for 0.5, 1, 2, 4 and 6 h. The cell media was removed, and the cells were washed in 1 ml PBS and centrifuged at 1400 rpm for 5 min. Cells were re-suspended in PBS and Cy3 siRNA detection in HeLa cells was observed by FACS. The cells were gated using forward (FSC-H)-versus side-scatter (SSC-H) to exclude debris and dead cells and cy3 intensity was measured by FACScalibur using FL-2 filter The quenching of external fluorescence, which distinguishes internalized from surface-adherent particles, can be accomplished with the use of vital dyes such as trypan blue (TB), which are incapable of penetrating intact cell membranes In order to distinguish between siRNA molecules that are internalized and are inside the cells from siRNA that is bound to the cells membrane, TB quenching protocol was used. The cells were incubated with 50 µl of 0.4% Trypan Blue for 10 min at RT, to allow quenching of extracellular Cy3 signal. Following this treatment only the Cy3 signal from siRNA that is in the cell can be observed. In FIGS. 13A and 13B, the solid line represents the untreated cells, and a dashed line represents the sphingolipid spermine treated cells. As can be seen in FIG. 13A, a shift in cell signal can be observed in cells treated with the conjugated siRNA (dashed line) already after 30 min suggesting binding of the sphingolipid spermine conjugated siRNA to the cells. This shift is increased reaching full staining of most of the cells after 6 h. This shift is hardly observed in the histogram for the cells that were treated with the non-conjugated siRNA. Moreover, the FACS analysis presented in FIG. 13B of cells treated with TB shows signal shift of cells treated with conjugated siRNA at 2 h of incubation. Suggesting that the sphingolipid spermine siRNA compound labeled with Cy3 that was already bound in 30 min (see above) was internalized and is found inside the cells. This cell signal shift isn't seen in the analysis of the cells treated with non conjugated siRNA labeled with Cy3 suggesting that the non conjugated siRNA cannot penetrate the cells.

Although the above examples have illustrated particular ways of carrying out embodiments of the invention, in practice persons skilled in the art will appreciate alternative ways of carrying out embodiments of the invention, which are not shown explicitly herein. It should be understood that the present disclosure is to be considered as an exemplification of the principles of this invention and is not intended to limit the invention to the embodiments illustrated.

Those skilled in the art will recognize, or be able to ascertain using no more than routine experimentation, equivalents of the specific embodiments of the invention described herein. Such equivalents are intended to be encompassed by the following claims.

The invention claimed is:

1. A compound comprising a sphingolipid-polyalkylamine conjugate, having general formula I:

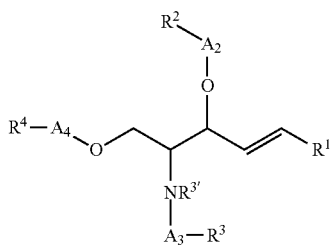

wherein
R$^1$ is a branched or linear C$_7$-C$_{24}$ alkyl, alkenyl or polyenyl;
R$^2$ is spermine,
R$^3$ and R$^4$ each independently is selected from the group consisting of hydrogen, a branched or linear polyalkylamine, an oligonucleotide and a protecting group;
R$^{3'}$ is hydrogen, C$_1$-C$_4$ alkyl or a protecting group;
A$_2$, A$_3$ and A$_4$ are each independently present or absent, but if present is selected from the group consisting of C(O), C(O)NHX, C(O)NHR$^5$X, C(O)R$^5$X, C(O)R$^5$C(O)X, R$^5$X and R$^5$OC(O)X;
R$^5$ is a branched or linear C$_1$-C$_{10}$ alkyl chain optionally substituted with one or more heteroatoms;
X is present or absent but if present is S, P, O or NH; and at least one of R$^3$ or R$^4$ is an oligonucleotide;
or a salt of such compound.

2. The compound or the salt of such compound of claim 1, wherein R$^1$ is C$_7$-C$_{24}$ alkyl, C$_{10}$-C$_{20}$ alkyl, C$_{10}$-C$_{16}$ alkyl, or C$_{13}$ alkyl.

3. The compound or the salt of such compound of claim 2, wherein A$_2$ or A$_4$ is C(O).

4. The compound or the salt of such compound of claim 1, wherein R$^{3'}$ is H, A$_2$ is C(O) and A$_3$ is absent.

5. The compound or the salt of such compound of claim 1, wherein the compound has a general formula Ia:

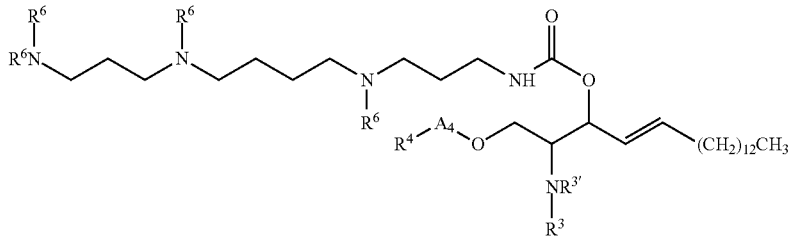

wherein
A$_4$ is present or absent, but if present is selected from the group consisting of C(O), C(O)NHX, C(O)NHR$^5$X, C(O)R$^5$X, C(O)R$^5$C(O)X, R$^5$X and R$^5$OC(O)X;
R$^3$ and R$^{3'}$ independently is hydrogen or a protecting group;
R$^4$ is an oligonucleotide;
R$^5$ is a branched or linear C$_1$-C$_{10}$ alkyl chain optionally substituted with one or more heteroatoms; and
each R$^6$ independently is hydrogen or a protecting group.

6. The compound or the salt of such compound of claim 1, wherein R$^4$ is an oligonucleotide which is a single-stranded oligonucleotide or a double-stranded oligonucleotide.

7. The compound or the salt of such compound of claim 6, wherein the double-stranded oligonucleotide is a double stranded RNA molecule selected from the group consisting of siRNA, miRNA, and miRNA mimetic.

8. The compound or the salt of such compound of claim 7, wherein the double-stranded oligonucleotide is a double-stranded RNA having the structure set forth below
5'(N)x-Z 3' antisense strand
3'Z'—(N')y-z''5' (sense strand)
wherein each of N and N' is an unmodified ribonucleotide, a modified ribonucleotide or an unconventional moiety;
wherein each of (N)x and (N')y is an oligonucleotide in which each consecutive N or N' is joined to the next N or N' by a covalent bond;
wherein each of x and y is independently an integer between 15 and 49;
wherein z'' is present or absent, but if present is a capping moiety covalently attached to the 5' terminus of the sense strand;
wherein each of Z and Z' is independently present or absent, but if present is 1-5 consecutive nucleotides or non-nucleotide moieties or a combination thereof covalently attached at the 3' terminus of the strand in which it is present;
wherein the sphingolipid-polyalkylamine conjugate is covalently attached to at least one of the 3' terminus of the antisense strand, the 3' terminus of the sense strand or the 5' terminus of the sense strand;
wherein the sequence of (N')y is substantially complementary to the sequence of (N)x; and wherein (N)x comprises an antisense sequence complementary to a consecutive sequence in a target RNA;
with the proviso that when the sphingolipid-polyalkylamine conjugate is attached at the 5' terminus of the sense strand z'' is absent.

9. The compound or the salt of such compound of claim 8, wherein x=y and each of x and y is 19, 20, 21, 22 or 23.

10. The compound or the salt of such compound of claim 8, wherein x is an integer from 19-25 and y is an integer from 15-17.

11. The compound or the salt of such compound of claim 8, wherein the sphingolipid-polyalkylamine conjugate is covalently attached to the 3' terminus of (N')y or to the 3' terminus of (N)x.

12. The compound or the salt of such compound of claim 8, wherein the sphingolipid-polyalkylamine conjugate is covalently attached to the 5' terminus of (N')y.

13. A composition comprising the compound or the salt of such compound of claim 1; and a pharmaceutically acceptable carrier.

14. A method for treating cancer in a subject having cancer comprising administering to the subject a therapeutic amount of the composition of claim 5.

15. The method of claim 14, wherein the compound is formulated for intratumoral, systemic, intraperitoneal or subcutaneous administration.

\* \* \* \* \*

SEQUENCE LISTING

<160> NUMBER OF SEQ ID NOS: 13

<210> SEQ ID NO 1
<211> LENGTH: 2341
<212> TYPE: RNA
<213> ORGANISM: homo_sapiens

<400> SEQUENCE: 1

| | | | | | |
|---|---|---|---|---|---|
| gggaggccgg | augugagugg | agcggccauu | uccuguuucu | cugcaguuuu | ccucagcuuu      60 |
| gggugguggc | cgcugccggg | caucggcuuc | caguccgcgg | agggcgaggc | ggcguggaca     120 |
| gcggccccgg | cacccagcgc | cccgccgccc | gcaagccgcg | cgcccguccg | ccgcgccccg     180 |
| agcccgccgc | uuccuaucuc | agcgcccugc | cgccgccgcc | gcggcccagc | gagcggcccu     240 |
| gaugcaggcc | aucaagugug | gguggugggg | agacggagcu | uagguaaaa  | cuugccuacu     300 |
| gaucaguuac | acaaccaaug | cauuuccugg | agaauauauc | ccuacugucu | uugacaauua     360 |
| uucugccaau | guuaugguag | auggaaaacc | ggugaaucug | ggcuuauggg | auacagcugg     420 |
| acaagaagau | uaugacagau | uacgccccu  | auccuauccg | caaacagaug | uguucuuaau     480 |
| uugcuuuucc | cuugugaguc | cugcaucauu | ugaaaaugug | cgugcaaagu | gguauccuga     540 |
| ggugcggcac | cacuguccca | acacucccau | cauccuagug | ggaacuaaac | uugaucuuag     600 |
| ggaugauaaa | gacacgaucg | agaaacugaa | ggagaagaag | cugacuccca | ucaccuaucc     660 |
| gcagggucua | gccauggcua | aggagauugg | ugcuguaaaa | uaccuggagu | gcucggcgcu     720 |
| cacacagcga | ggccucaaga | cagucuuuga | cgaagcgauc | cgagcagucc | ucugcccgcc     780 |
| ucccgugaag | aagaggaaga | gaaaaugccu | gcuguuguaa | augcucagc  | cccucguucu     840 |
| ugguccuguc | ccuuggaacc | uuuguacgcu | ugcucaaaa  | aaaacaaaa  | aaaaaaaaca     900 |
| aaaaaaaaa  | acaacggugg | agccuucgca | cucaaugcca | acuuuugu   | acagauuaau     960 |
| uuuuccauaa | aaccauuuuu | ugaaccaauc | aguaauuuua | agguuuguu  | uguucuaaau    1020 |
| guaagaguuc | agacucacau | ucuauuaaaa | uuuagcccua | aaaugacaag | ccuucuuaaa    1080 |
| gccuuauuuu | ucaaaagcgc | ccccccauu  | cuuguucaga | uuaagaguug | ccaaaauacc    1140 |
| uucugaacua | cacugcauug | uugugccgag | aacaccgagc | acugaacuuu | gcaaagaccu    1200 |
| ucgucuuuga | gaagacggua | gcuucugcag | uuaggaggug | cagacacuug | cucuccuaug    1260 |
| uaguucucag | augcguaaag | cagaacagcc | ucccgaauga | agcguugcca | uugaacucac    1320 |
| cagugaguua | gcagcacgug | uucccgacau | aacauuguac | uguaauggag | ugagcguagc    1380 |
| agcucagcuc | uuuggaucag | ucuuugugau | uucauagcga | guuucugac  | cagcuuuugc    1440 |
| ggagauuuug | aacagaacug | cuauuuccuc | uaaugaagaa | uucuguuuag | cuguggguguu   1500 |
| gccggguggg | gugugguguga | ucaaaggaca | aagacaguau | uuugacaaaa | uacgaagugg    1560 |
| agauuuacac | uacauuguac | aaggaaugaa | agucacgg   | guaaaaacuc | uaaaagguua    1620 |
| auuucuguca | aaugcaguag | augaugaaag | aaagguuggu | auuaucagga | aauguuuucu    1680 |
| uaagcuuuuc | cuuucucuua | caccugccau | gccuccccaa | auugggcauu | uaauucaucu    1740 |
| uuaaacuggu | uguucuguua | gucgcuaacu | aguaaguge  | uuuucuuaua | gaaccccuuc    1800 |
| ugacugagca | auaugccucc | uuguauuaua | aaaucuuucu | gauaaugcau | uagaagguuu    1860 |
| uuuugucgau | uaguaaaagu | gcuuccaug  | uuacuuuauu | cagagcuaau | aagugcuuuc    1920 |
| cuuaguuuuc | uaguaacuag | guguaaaaau | cauguguugc | agcuuuauag | uuuuaaaau    1980 |
| auuuuagaua | auucuaaac  | uaugaaccuu | cuuaacauca | cugucuugcc | agauuaccga    2040 |
| cacugucacu | ugaccaauac | ugacccucuu | uaccucgccc | acgcggacac | acgccuccug    2100 |

-continued

| | | |
|---|---|---|
| uagucgcuuu gccauuugau guuccuuugg gucugugagg uucguaaaac ugugcuagug | 2160 |
| cugacgaugu ucuguacaac uuaacucacu ggcgagaaua cagcguggga cccuucagcc | 2220 |
| acuacaacag aauuuuuuaa auugacaguu gcagaauugu ggaguguuuu acauugauc | 2280 |
| uuuugcuaau gcaauuagca uuauguuuug cauguaugac uuaauaaauc cuugaaucau | 2340 |
| a | 2341 |

<210> SEQ ID NO 2
<211> LENGTH: 2204
<212> TYPE: RNA
<213> ORGANISM: homo_sapiens

<400> SEQUENCE: 2

| | | |
|---|---|---|
| gagcggugcg gaggcucugc ucggaucgag gucugcagcg cagcuucggg agcaugagug | 60 |
| cugcagugac ugcagggaag cuggcacggg caccggccga cccugggaaa gccggggucc | 120 |
| ccggaguugc agcucccgga gcuccggcgg cggcuccacc ggcgaaagag aucccggagg | 180 |
| uccuagugga cccacgcagc cggcggcgcu augugcgggg ccgcuuuuug ggcaagggcg | 240 |
| gcuuugccaa gugcuucgag aucucggacg cggacaccaa ggaguguuc gcgggcaaga | 300 |
| uugugccuaa gucucugcug cucaagccgc accagaggga aagaugucc auggaaauau | 360 |
| ccauucaccg cagccucgcc caccagcacg ucuaggauu ccacggcuuu ucgaggaca | 420 |
| acgacuucgu guucguggug uuggagcucu gccgccggag gucucuccug gagcugcaca | 480 |
| agaggaggaa agcccugacu gagccugagg cccgauacua ccuacggcaa auugugcuug | 540 |
| gcugccagua ccugcaccga aaccgaguua uucaucgaga ccuaagcug ggcaaccuuu | 600 |
| uccugaauga agaucuggag gugaaaauag gggauuuugg acuggcaacc aaagucgaau | 660 |
| augacgggga gaggaagaag acccugugug ggaccccuaa uuacauagcu cccgaggugc | 720 |
| ugagcaagaa agggcacagu ucgagguggu gugugggguc cauuggggugu aucauguaua | 780 |
| ccuuguuagu gggcaaaacca ccuuuugaga cuucuugccu aaaagagacc uaccuccgga | 840 |
| ucaagaagaa ugaauacagu auucccaagc acaucaaccc cguggccgcc ucccucaucc | 900 |
| agaagaugcu ucagacagau cccacugccc gccaaccau uaacgagcug cuuaaugacg | 960 |
| aguucuuuac uucuggcuau aucccugccc gucuccccau caccugccug accauuccac | 1020 |
| caagguuuuc gauugcuccc agcagccugg accccagcaa ccggaagccc ucacagucc | 1080 |
| ucaauaaagg cuuggagaac ccccugccug agcguccccg ggaaaaagaa gaaccagugg | 1140 |
| uucgagagac aggugaggug gucgacugcc accucaguga caugcugcag cagcugcaca | 1200 |
| gugucaaugc cuccaagccc ucggagcgug ggcuggucag gcaagaggag gcugaggauc | 1260 |
| cugccugcau ccccaucuuc ugggucagca auguggugga cuauucggac aaguacggcc | 1320 |
| uuggguauca gcucugugau aacagcgugg gggugcucuu caaugacuca acacgcccuca | 1380 |
| uccucuacaa ugauggugac agccugcagu acauagagcg ugacggcacu gaguccuacc | 1440 |
| ucaccgugag uucccaucccc aacuccuuga ugaagaagau caccccuccuu aaauauuucc | 1500 |
| gcaauuacau gagcgagcac uugcugaagg caggugccaa caucacgccg cgcgaaggug | 1560 |
| augagcucgc ccggcugccc uaccacggga ccugguccg caccgcagc gccaucaucc | 1620 |
| ugcaccucag caacggcagc gugcagauca acuucuucca ggaucacacc aagcucaucu | 1680 |
| ugugcccacu gauggcagcc gugaccuaca ucgacgagaa gcgggacuuc cgcacauacc | 1740 |
| gccugagucu ccuggaggag uacggcugcu gcaaggagcu ggccagccgg cuccgcuacg | 1800 |

| | |
|---|---|
| cccgcacuau gguggacaag cugcugagcu cacgcucggc cagcaaccgu cucaaggccu | 1860 |
| ccuaauagcu gcccucccu ccggacuggu gcccuccuca cucccaccug caucggggc | 1920 |
| ccauacuggu uggcucccgc ggugccaugu cugcagugug ccccccagcc ccgguggcug | 1980 |
| ggcagagcug caucauccuu gcagguggg guugcugugu aaguuauuuu uguacauguu | 2040 |
| cggguguggg uucuacagcc uugucccccu cccccucaac cccaccauau gaauuguaca | 2100 |
| gaauauuucu auugaauucg gaacugaccu uccuuggcu uuaugcacau uaaacagaug | 2160 |
| ugaauauuca aaaaaaaaa aaaaaaaaa aaaaaaaaa aaaa | 2204 |

<210> SEQ ID NO 3
<211> LENGTH: 5889
<212> TYPE: RNA
<213> ORGANISM: homo_sapiens

<400> SEQUENCE: 3

| | |
|---|---|
| uccuaggcgg cggccgcggc ggcggaggca gcagcggcgg cggcagugc ggcggcgaag | 60 |
| guggcggcg cucggccagu acuccccggcc cccgccauuu cggacuggga gcgagcgcgg | 120 |
| cgcaggcacu gaaggcggcg gcggggccag aggcucagcg gcucccaggu gcggagaga | 180 |
| ggccugcuga aaaugacuga auauaaacuu guggauguug gagcugguggg cguaggcaag | 240 |
| agugccuuga cgauacagcu aauucagaau cauuuugugg acgaauauga uccaacaaua | 300 |
| gaggauuccu acaggaagca aguaguaauu gauggagaaa ccugucucuu ggauauuuc | 360 |
| gacacagcag gucaagagga guacagugca augagggacc aguacaugag gacuggggag | 420 |
| ggcuuucuuu guguauuugc cauaauuau acuaaaucau ugaagauau ucaccauuau | 480 |
| agagaacaaa uuaaaagagu uaaggacucu gaagaugu cuaugguccu aguaggaaau | 540 |
| aaaugugauu ugccuucag aacaguagac acaaaacagg cucaggacuu agcaagaagu | 600 |
| uauggaauuc cuuuuauuga aacaucagca agacaagac agagaguggga ggaugcuuuu | 660 |
| auacauuggg ugagggagau ccgacaauac agauugaaa aaaucagcaa agaagaaaag | 720 |
| acuccuggcu gugugaaaau uaaaaaaugc auuauaaugu aaucggguug uugaugaugc | 780 |
| cuucuauaca uuaguucgag aaauucgaa acauaaagaa aagaugagca aagaugguaa | 840 |
| aaagaagaaa aagaagucaa agacaaagug uguauuaug uaaauacaau uuguacuuuu | 900 |
| uucuuaaggc auacuaguac aaguggaauu uuuguacau uacacuaaau auuuagcauu | 960 |
| uguuuuagca uuaccuaauu uuuuuccugc uccaugcaga cuguuagcuu uuaccuuaaa | 1020 |
| ugcuauuuuu aaaaugacag uggaaguuuu uuuuuccucu aagugccagu auucccagag | 1080 |
| uuuugguuuu ugaacuagca augccuguga aaaagaaacu gaauaccuaa gauuucuguc | 1140 |
| uuggguuuu uggugcaugc aguugauuac ucuuauuuu ucuuaccaau ugugaauguu | 1200 |
| ggugugaaac aaauuaauga agcuuuugaa ucacccuau ucuguguuuu aucuagucac | 1260 |
| auaaauggau uaauuacuaa uuucaguuga gaccuucuaa uugguuuuua cugaaacauu | 1320 |
| gagggaacac aaauuuaugg gcuuccugau gaugauucu cuaggcauca uguccuauag | 1380 |
| uuugucaucc cugaugaaug uaaaguuaca cuguucacaa agguuugcc ccuuccac | 1440 |
| ugcuauuagu cauggucacu cuccccaaaa uauuauauuu uucuauaaa agaaaaaaa | 1500 |
| uggaaaaaaa uuacaaggca auggaaacua uuauaaggcc auuccuuuu cacauuagau | 1560 |
| aaauuacuau aaagacuccu aauagcuuuu ccguuaagg cagacccagu augaaauggg | 1620 |
| gauuauuaua gcaaccauuu uggggcuaua uuuacaugcu acuaaauuuu uauauaauu | 1680 |
| gaaaagauuu uaacaaguau aaaaaauucu cauaggaauu aaaugugauc ucccuguguc | 1740 |

```
agacugcucu uccauaguau aacuuuaaau cuuuucuuca acuugagucu uugaagauag   1800
uuuuaauucu gcuugugaca uuaaaagauu auuugggcca guuauagcuu auuaggugug   1860
gaagagacca agguugcaag gccaggcccu gugugaaccu ugagcuuuc auagagaguu   1920 ucacagcaug gacugugucc ccacggucau ccaguguugu caugcauugg uuagucaaaa   1980
uggggaggga cuagggcagu uggauagcu caacaagaua caaucucacu cuguggugu    2040 ccugcugaca aaucaagagc auugcuuug uuucuuaaga aaacaaacuc uuuuuaaaa    2100 auuacuuuua aauauuaacu caaaaguuga gauuuggggg uggugugug ccaagacauu    2160 aauuuuuuuu uuaaacaaug aagugaaaaa guuuacaau cucuagguuu ggcuaguucu    2220
cuuaacacug guuaaauuaa cauugcauaa acacuuuca agucugaucc auauuuaaua    2280
augcuuuaaa auaaaaauaa aaacaauccu uugauaaau uaaaaugu acuuauuua      2340 aaauaaauga agugagaugg cauggugagg ugaaaguauc acggacuag aagaaggug    2400 acuuagguuc uagauaggug ucuuuuagga cucugauuuu gaggacauca cuuacuaucc   2460 auucuucau guuaaagaa gucaucucaa acucuuaguu uuuuuuuuu acaacuaugu     2520 aauuuauauu ccauuacau aaggauacac uuauuguca agcucagcac aaucuguaaa    2580
uuuuuaaccu auguuacacc aucuucagug ccagucuugg gcaaaauugu gcaagaggug   2640
aaguuuauau uugaauaucc auucgguu uaggacucuu cuuccauauu agugucaucu    2700
ugccucccua ccuuccacau gccccaugac uugaugcagu uuuaauacuu guaauucccc   2760
uaaccauaag auuuacugcu gcugggaua ucuccaugaa guuucccac ugagucacau    2820 cagaaaugcc cuacaucuua uuuccucagg gcucaagaga aucugacaga uaccauaaag   2880
ggauuugacc uaaucacuaa uuuucaggug guggcugaug cuuugaacau ucucuugcug   2940
cccaauccau uagcgacagu aggauuuuuc aaaccuggua ugaauagaca gaacccuauc   3000
caguggaagg agaauuuaau aaagauagu cugaaagaau uccuaggua aucuauaacu    3060 aggacuacuc cugguaacag uaauacauuc cauuguuuua guaaccagaa aucuucaugc   3120
aaugaaaaau acuuuaauuc augaagcuua cuuuuuuuu uugggucag agucucgcuc    3180 uugucacccca ggcuggaaug caguggcgcc aucucagcuc acugcaaccu ccaucuccca   3240
gguucaagcg auucgcgug cucggccucc ugaguagcug ggauuacagg cgugugccac   3300
uacacucaac uaauuuugu auuuuuagga gagacgggu ucacccugu uggccaggcu     3360 ggucucgaac uccugaccuc aagugauuca cccaccuugg ccucauaaac cuguuuugca   3420
gaacucauuu auucagcaaa uauuuauuga gugccuacca gaugccaguc accgcacaag   3480
gcacugggua uaugguaucc ccaaacaaga gacauaaucc cggcccuuag guagugcuag   3540 uggucugu aauacuuac uaaggccuuu gguauacgac ccagagauaa cacgaugcgu      3600
auuuuaguuu ugcaaagaag ggguuuggu ucugugccag cucuauaauu guuuugcuac    3660
gauuccacug aaacucuucg aucaagcuac uuuauguaaa ucacuucauu guuuuaaagg   3720
aauaaacuug auuauaugu uuuuuauuu ggcauaacug ugauucuuuu aggacaauua    3780
cuguacacau uaaggaguau gucagauauu cauauugacc caaagugua auauccagu    3840 uuucucugca uaaguaauua aaauauacuu aaaaauuaau aguuuaucu ggguacaaau   3900 aaacaggugc cugaacuagu ucacagacaa ggaaacuucu auguaaaaau cacuaugauu   3960
ucugaauugc uaugugaaac uacagaucuu uggaacacug uuuagguagg uguuaaagac   4020
uuacacagua ccucguuucu acacagagaa agaaauggcc auacuucagg aacugcagug   4080
```

| | |
|---|---|
| cuuaugaggg gauauuuagg ccucuugaau uuuugaugua gaugggcauu uuuuuaaggu | 4140 |
| agugguuaau uaccuuuaug ugaacuuuga augguuaaac aaaagauuug uuuuuguaga | 4200 |
| gauuuuaaag ggggagaauu cuagaaauaa auguuaccua auuauuacag ccuuaaagac | 4260 |
| aaaaauccuu guugaaguuu uuuuaaaaaa agcuaaauua cauagacuua ggcauuaaca | 4320 |
| uguuugugga agaauauagc agacguauau uguaucauuu gagugaaugu ucccaaguag | 4380 |
| gcauucuagg cucuauuuaa cugagucaca cugcauagga auuuagaacc uaacuuuuau | 4440 |
| agguuaucaa aacuguuguc accauugcac aauuuuguee uaauauauac auagaaacuu | 4500 |
| uguggggcau guuaaguuac aguuugcaca agucaucuc auuuguauuc cauugauuuu | 4560 |
| uuuuuucuuc uaaacauuuu uucuucaaac aguauauaac uuuuuuagg ggauuuuuuu | 4620 |
| uuagacagca aaaacuaucu gaagauuucc auuugucaaa aaguaaugau uccuugauaa | 4680 |
| uuguguagua auguuuuuua gaacccagca guuaccuuaa agcugaauuu auauuuagua | 4740 |
| acuucugugu uaauacugga uagcaugaau ucugcauuga gaaacugaau agcugucaua | 4800 |
| aaaugaaacu uucuuucuaa agaaagauac ucacaugagu ucuugaagaa uagucauaac | 4860 |
| uagauuaaga ucuguguuuu aguuuaauag uuugaagugc cuguuuggga uaaugauagg | 4920 |
| uaauuuagau gaauuuaggg gaaaaaaaag uuaucugcag auauguugag ggcccaucuc | 4980 |
| ucccccacac cccccacaga gcuaacuggg uuacaguguu uuauccgaaa guuccaauu | 5040 |
| ccacugucuu uguuuucau guugaaaaua cuuuugcauu uuuccuuuga ugccaauuu | 5100 |
| cuuacuagua cuauuucuua auguaacaug uuuaccugga auguauuua acuauuuuug | 5160 |
| uauaguguaa acugaaacau gcacauuuug uacauugugc uuucuuuugu gggacauaug | 5220 |
| cagugugauc caguuguuuu ccaucauuug guugcgcuga ccuaggaaug uuggucauau | 5280 |
| caaacauuaa aaaugaccac ucuuuuaauu gaaauuaacu uuuaaauguu uauaggagua | 5340 |
| ugcugcuguga agugaucuaa aauuuguaau auuuuuguca ugaacuguac uacuccuaau | 5400 |
| uauuguaaug uaauaaaaau aguuacagug acuaugagug uguauuuauu caugaaauuu | 5460 |
| gaacuguuug ccccgaaaug gauauggaau acuuuauaag ccauagacac uauaguauac | 5520 |
| cagugaaucu uuuaugcagc uuguuagaag uauccuuuau uucuaaaagg ugcuguggau | 5580 |
| auuauguaaa ggcguguuug cuuaaacuua aaaccauauu uagaaguaga ugcaaaacaa | 5640 |
| aucugccuuu augacaaaaa aauaggauaa cauuauuuau uuauuuccuu uuaucaaaga | 5700 |
| agguaauuga uacacaacag gugacuuggu uuuaggccca aagguagcag cagcaacauu | 5760 |
| aauaauggaa auaauugaau aguuaguauu guaguuaaau gccagucacc agcaggcuau | 5820 |
| uucaaggucu gaaguaauga cuccauacau auuauuuauu ucuauaacua cauuuaaauc | 5880 |
| auuaccagg | 5889 |

<210> SEQ ID NO 4
<211> LENGTH: 5765
<212> TYPE: RNA
<213> ORGANISM: homo_sapiens

<400> SEQUENCE: 4

| | |
|---|---|
| uccuaggcgg cggccgcggc ggcggaggca gcagcggcgg cggcagugge ggcggcgaag | 60 |
| gugggcggcgg cucggccagu acuccccggcc cccgccauuu cggacuggga gcgagcgcgg | 120 |
| cgcaggcacu gaaggcggcg gcggggccag aggcucagcg gcucccaggu gcgggagaga | 180 |
| ggccugcuga aaaugacuga auauaaacuu gugguaguu gagcugguug gcuaggcaag | 240 |
| agugccuuga cgauacagcu aauucagaau cauuuugugg acgaauauga uccaacaaua | 300 |

| | | | | |
|---|---|---|---|---|
| gaggauuccu | acaggaagca | aguaguaauu | gauggagaaa | ccugucucuu ggauauucuc | 360 |
| gacacagcag | gucaagagga | guacagugca | augagggacc | aguacaugag gacuggggag | 420 |
| ggcuuucuuu | guguauuugc | cauaaauaau | acuaaaucau | ugaagauau ucaccauuau | 480 |
| agagaacaaa | uuaaaagagu | uaaggacucu | gaagauguac | cuauggyccu aguaggaaau | 540 |
| aaaugugauu | ugccuucuag | aacaguagac | acaaacagg | cucaggacuu agcaagaagu | 600 |
| uauggaauuc | cuuuuauuga | aacaucagca | agacaagac | aggguguuga ugaugccuuc | 660 |
| uauacauuag | uucgagaaau | ucgaaaacau | aaagaaaaga | ugagcaaaga ugguaaaaag | 720 |
| aagaaaaaga | agucaaagac | aaagugugua | auuauguaaa | uacaauuugu acuuuuucu | 780 |
| uaaggcauac | uaguacaagu | gguaauuuuu | guacauuaca | cuaaauuauu agcauugyuu | 840 |
| uuagcauuac | cuaauuuuuu | uccugcuccca | ugcagacugu | uagcuuuuac cuuaaaugcu | 900 |
| uauuuaaaa | ugacagugga | aguuuuuuuu | uccucuaagu | gccaguauuc ccagaguuuu | 960 |
| gguuuuugaa | cuagcaaugc | cugugaaaaa | gaaacugaau | accaagauu ucugucuugg | 1020 |
| gguuuuuggu | gcaugcaguu | gauuacuucu | uauuuucuu | accaauugyg aauguuggug | 1080 |
| ugaaacaaau | uaaugaagcu | uuugaaucau | cccuauucug | uguuuaaucu agucacauaa | 1140 |
| auggauuaau | uacuaauuuc | aguugagacc | uucuaauugg | uuuuuacuga aacauugagg | 1200 |
| gaacacaaau | uuaugggcuu | ccugaugaug | auucuucuag | gcaucauguc cuauaguuug | 1260 |
| ucaucccuga | ugaauguaaa | guuacacugu | ucacaaaggu | uugucuccu uuccacugcu | 1320 |
| auuagucaug | gucacucucc | ccaaaauauu | auauuuuuc | uauaaaaga aaaaauggaa | 1380 |
| aaaaaauuac | aaggcaaugg | aaacuauuau | aaggccauuu | ccuuuucaca uuagauaaau | 1440 |
| uacuauaaag | acuccuaaua | gcuuuuccug | uuaaggcaga | cccaguauga augggggauu | 1500 |
| auuauagcaa | ccauuuuggg | gcuauauuua | caugcuacua | aauuuuauua auaauugaaa | 1560 |
| agauuuuaac | aaguauaaaa | aauucucaua | ggaauuaaau | guagcuccc uguguucagac | 1620 |
| ugcucuuuca | uaguauaacu | uuaaaucuuu | ucuucaacuu | gagucuuuga agauaguuu | 1680 |
| aauucugcuu | gugacauuaa | aagauuauuu | gggccaguua | uagcuuauua ggguguugaag | 1740 |
| agaccaaggu | ugcaaggcca | ggcccugugu | gaaccuuuga | gcuuucauag agaguuucac | 1800 |
| agcauggacu | guguccccac | ggucauccag | uguguacaug | cauugguuag ucaaaauggg | 1860 |
| gagggacuag | ggcaguuugg | auagcucaac | aagaucaau | cucacucugu gguguccug | 1920 |
| cugacaaauc | aagagcauug | cuuuugyuuc | uuaagaaaac | aaacucuuu uuaaaaauua | 1980 |
| cuuuaaauua | uuaacucaaa | aguugagauu | uggggugyu | ggugugccaa gacauuaauu | 2040 |
| uuuuuuuaa | acaaugaagu | gaaaaaguuu | uacaaucucu | agguuuggcu aguucucuua | 2100 |
| acacugguua | aauuaacauu | gcauaaacac | uuucaaguc | ugaccauau uuauaaaugc | 2160 |
| uuuaaaauaa | aaauaaaaac | aauccuuuug | auaaauuuaa | auguuacuu auuuaaaau | 2220 |
| aaaugaagug | agauggcaug | gugaggugaa | aguaucacug | gacuaggaag aaggugaccuu | 2280 |
| agguucuaga | uaggugucuu | uuaggacucu | gauuugagg | acaucacuua cuauccauuu | 2340 |
| cuucauguua | aaagaaguca | ucucaaacuc | uuaguuuuuu | uuuuuuacaa cuauguaauu | 2400 |
| uauauuccau | uuacauaagg | auacacuauu | ugucaagcu | cagcacaauc uguaaauuuu | 2460 |
| uaaccuaugu | uacaccaucu | ucagugccag | ucuugggcaa | aauugugcaa gaggugaagu | 2520 |
| uuauauuuga | auaccauuc | ucguuuuagg | acuuucuuc | cauauuagug ucaucuugcc | 2580 |
| ucccuaccuu | ccacaugccc | caugacuuga | ugcaguuuua | auacuuguaa uuccccuaac | 2640 |

```
cauaagauuu acugcugcug uggauaucuc caugaaguuu ucccacugag ucacaucaga    2700
aaugcccuac aucuuauuuc cucagggcuc aagagaaucu gacagauacc auaaagggau    2760
uugaccuaau cacuaauuuu caggugguqg cugaugcuuu gaacaucucu uugcugccca    2820
auccauuagc gacaguagga uuuuucaaac cugguaugaa uagacagaac ccuauccagu    2880
ggaaggagaa uuuaauaaag auagugcuga aagaauuccu uagguaaucu auaacuagga    2940
cuacuccugg uaacaguaau acauuccauu guuuuaguaa ccagaaaucu ucaugcaaug    3000
aaaaauacuu uaauucauga agcuuacuuu uuuuuuugg ugucagaguc ucgcucuugu     3060
cacccaggcu ggaaugcagu ggcgccaucu cagcucacug caacuccau cucccagguu     3120 caagcgauuc ucgugccucg gccuccugag uagcugggau uacaggcgug ugccacuaca    3180
cucaacuaau uuuuguauuu uuaggagaga cggqguuuca cccuguuggc caggcugguc    3240
ucgaacuccu gaccucaagu gauucaccca ccuuggccuc auaaaccugu uugcagaac     3300 ucauuuauuc agcaaauauu uauugagugc cuaccagaug ccagucaccg cacaaggcac    3360
uggguauaug guaucccaa acaagagaca uaaucccggu ccuuagguag ugcuagugug     3420
gucuguaaua ucuuacuaag gccuuuggua uacgacccag agauaacacg augcguauuu    3480
uaguuuugca aagaaggggu uuggucucug ugccagcucu auaauuguuu ugcuacgauu    3540
ccacugaaac ucuucgauca agcuacuuua uguaaaucac ucauuguuu uaaaggaaua     3600 aacuugauua uauuguuuuu uuauuuggca uaacugugaa ucuuuuagga caauuacugu    3660
acacauuaag guguauguca gauuucauua uugacccaaa uguguaauau uccaguuuuc    3720
ucugcauaag uaauuaaaau uacuuuaaaa auuaauaguu uuaucggguu acaaauaaac    3780
aggugccuga acuaguucac agacaaggaa acuucuaugu aaaaaucacu augauuucug    3840
aauugcuaug ugaaacuaca gaucuuugga cacuguuuua gguagggugu uaagacuuac    3900
acaguaccuc guuucuacac agagaaagaa auggccauac ucaggaacu gcagugcuua     3960 ugaggggaua uuuaggccuc uugaauuuuu gauguagaug ggcauuuuuu uaagguagug    4020
guuaauuacc uuuaugugaa cuuugaaugg uuuaacaaaa gauuuguuuu uguagagauu    4080 uuaaagggg agaauucuag aaauaaaugu uaccuaauua uuuacagccuu aaagacaaaa    4140 auccuuguug aaguuuuuuu aaaaaaagcu aaauuacaua gacuuaggca uuaacauguu    4200
uguggaagaa uauagcagac guauauugua ucauuugagu gaauguuccc aaguaggcau    4260
ucuaggcucu auuuaacuga gucacacugc auaggaauuu agaaccuaac uuuuauaggu    4320
uaucaaaacu guugucacca uugcacaauu uguccuaau auauacauag aaacuuugug     4380
gggcauguua aguacaguu ugcacaaguu caucucauuu guauccauu gauuuuuuuu      4440 uucuucuaaa cauuuuucu ucaaacagua uauaacuuuu uuagggggau uuuuuuuag      4500 acagcaaaaa cuaucugaag auuuccauuu gucaaaaagu aaugauuucu ugauaauugu    4560
guaguaaugu uuuuuagaac ccagcaguua ccuaaagcu gaauuauau uuaguaacuu      4620 cuguguuaau acuggauagc augaauucug cauugagaaa cugaauagcu gucauaaaau    4680
gaaacuuucu uucuaaagaa agauacucac augaguucuu gaagaauagu cauaacuaga    4740
uuaagaucug uguuuaguu uaauaguuug aagugccugu ugggauaau gauagguaau      4800 uuagaugaau uaggggaaa aaaaguuau cugcagauau guugagggcc caucucuccc      4860
cccacacccc cacagagcua acugggguac aguguuuuau ccgaaaguuu ccaauuccac    4920
ugucuugugu uuucauguug aaauacuuu ugcauuuuc cuugagugc caauuccuua      4980 cuaguacuau uucuuaaugu aacauguuua ccuggaaugu auuuuaacua uuuuguaua     5040
```

```
guguaaacug aaacaugcac auuuuguaca uugugcuuuc uuuugggga cauaugcagu    5100 gugauccagu uguuuccau cauuugguug cgcugaccua ggaauguugg ucauaucaaa    5160
cauuaaaaau gaccacucuu uuaauugaaa uuaacuuuua aauguuuaua ggaguaugug    5220
cugugaagug aucuaaaauu uguaauauuu ugucaugaa cuguacuacu ccuaauuauu    5280
guaauguaau aaaaauaguu acagugacua ugagugugua uuuauucaug aaauuugaac    5340
uguuugcccc gaauggaua uggaauacuu auaagccau agacacuaua guauaccagu     5400
gaaucuuuua ugcagcuugu uagaaguauc cuuuauuucu aaaaggugcu guggauauua   5460
uguaaaggcg uguuugcuua aacuuaaaac cauauuuaga aguagaugca aaacaaaucu   5520
gccuuuauga caaaaaaaua ggauaacauu auuuauuuau uuccuuuuau caaagaaggu   5580
aauugauaca caacagguga cuugguuuua ggcccaaagg uagcagcagc aacauuaaua   5640
auggaaauaa uugaauaguu aguuauguau guuaaugcca gucaccagca ggcuauuuca   5700
aggucagaag uaaugacucc auacauauua uuuauuucua uaacuacauu uaaaucauua   5760
ccagg                                                              5765

<210> SEQ ID NO 5
<211> LENGTH: 19
<212> TYPE: RNA
<213> ORGANISM: Artificial
<220> FEATURE:
<223> OTHER INFORMATION: Chemically Synthesized

<400> SEQUENCE: 5
cgugcaaagu gguauccug                                               19

<210> SEQ ID NO 6
<211> LENGTH: 19
<212> TYPE: RNA
<213> ORGANISM: Artificial
<220> FEATURE:
<223> OTHER INFORMATION: Chemically Synthesized

<400> SEQUENCE: 6
caggauacca cuuugcacg                                               19

<210> SEQ ID NO 7
<211> LENGTH: 19
<212> TYPE: RNA
<213> ORGANISM: Artificial
<220> FEATURE:
<223> OTHER INFORMATION: Chemically Synthesized

<400> SEQUENCE: 7
agaagaugcu ucagacagu                                               19

<210> SEQ ID NO 8
```

```
<211> LENGTH: 19
<212> TYPE: RNA
<213> ORGANISM: Artificial
<220> FEATURE:
<223> OTHER INFORMATION: Chemically Synthesized

<400> SEQUENCE: 8
acugucugaa gcaucuucu                                                    19

<210> SEQ ID NO 9
<211> LENGTH: 19
<212> TYPE: RNA
<213> ORGANISM: Artificial
<220> FEATURE:
<223> OTHER INFORMATION: Chemically Synthesized

<400> SEQUENCE: 9
guaaggcaga cccaguaua                                                    19

<210> SEQ ID NO 10
<211> LENGTH: 19
<212> TYPE: RNA
<213> ORGANISM: Artificial
<220> FEATURE:
<223> OTHER INFORMATION: Chemically Synthesized

<400> SEQUENCE: 10
uauacugggu cugccuuac                                                    19

<210> SEQ ID NO 11
<211> LENGTH: 51
<212> TYPE: DNA
<213> ORGANISM: Artificial
<220> FEATURE:
<223> OTHER INFORMATION: Chemically Synthesized

<400> SEQUENCE: 11
gtcgtatcca gtgcagggtc cgaggtattc gcactggata cgaccgtgca a                51

<210> SEQ ID NO 12
<211> LENGTH: 21
<212> TYPE: DNA
<213> ORGANISM: Artificial
<220> FEATURE:
<223> OTHER INFORMATION: Chemically Synthesized

<400> SEQUENCE: 12
cggcggcagg ataccacttt g                                                 21

<210> SEQ ID NO 13
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 13
agtgcagggt ccgaggtatt                                                   20
```